United States Patent [19]
Bös et al.

[11] Patent Number: 5,646,173
[45] Date of Patent: Jul. 8, 1997

[54] TRICYCLIC PYRROLE DERIVATIVES USEFUL AS 5-HT SELECTIVE AGENTS

[75] Inventors: Michael Bös, Rheinfelden, Switzerland; Jürgen Wichmann, Lörrach, Germany; Ulrich Widmer, Rheinfelden, Switzerland

[73] Assignee: Hoffmann-La Roche Inc., Nutley, N.J.

[21] Appl. No.: 594,533

[22] Filed: Feb. 21, 1996

Related U.S. Application Data

[63] Continuation of Ser. No. 317,258, Oct. 3, 1994, abandoned.

[30] Foreign Application Priority Data

Oct. 22, 1993 [CH] Switzerland .............. 3202/93
Aug. 17, 1994 [CH] Switzerland .............. 2529/94

[51] Int. Cl.$^6$ .................. C07D 209/58; A61K 31/40
[52] U.S. Cl. .................. 514/411; 548/427; 548/430
[58] Field of Search .................. 514/411; 548/427

[56] References Cited

U.S. PATENT DOCUMENTS 3,997,557 12/1976 Helsley et al. .
5,244,888 9/1993 DeBernardis et al. .................. 514/183
5,292,732 3/1994 Rover .

FOREIGN PATENT DOCUMENTS 0521368 6/1992 European Pat. Off. .
94/14777 7/1994 WIPO .

OTHER PUBLICATIONS

S.J. Peroutka, Biol. Psychiatry, 20, 971–979 (1985).
A. Pazos et al., Europ. J. Pharmacol. 106, 539–546 (1984).
D. Hoyer, *J. Receptor Research* 8, 59–81 (1988).
J.E. Leysen, Molecular Pharmacology, 21, 301–314 (1981).
S. Havlic et al., Brain Research, 584, 191–196 (1992).
T. Branchek et al., Molecular Pharmacology 38, 604–609 (1990).
Berendsen & Broekkamp, Eur. J. Pharmacol. 135, 279–287 (1987).

*Primary Examiner*—Jacqueline Haley
*Attorney, Agent, or Firm*—George W. Johnston; Ellen Ciambrone Coletti; Robert A. Silverman

[57] ABSTRACT

The invention relates to tricyclic pyrrole derivatives useful as 5-HT selective agents of the formula

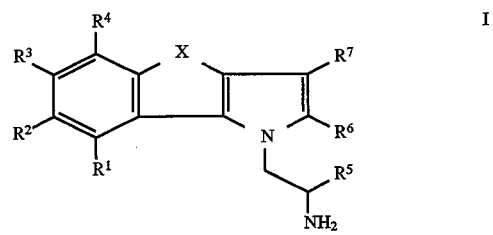

wherein
$R^1$ to $R^4$ are, independently, hydrogen, halogen, lower alkyl, phenyl, cycloalkyl or lower alkoxy and $R^2$ additionally is lower alkoxycarbonyl, acyloxy or mesyloxy;
$R^5$ to $R^7$ are, independently, hydrogen or lower alkyl;
X is $-CH_2CH(C_6H_5)-$, $-CH=C(C_6H_5)-$, $-YCH_2-$, $-CH=CH-$ or $-(CR^{11}R^{12})_n$;
$R^{11}$ and $R^{12}$ are, independently, hydrogen, phenyl, lower alkyl or halogen;
n is 1 to 3 and
y is O or S,
as well as pharmaceutically acceptable salts of basic compounds of formula I with pharmaceutically acceptable acids.

25 Claims, No Drawings

TRICYCLIC PYRROLE DERIVATIVES USEFUL AS 5-HT SELECTIVE AGENTS

This is a continuation of application Ser. No. 08/317,258, filed Oct. 3, 1994 now abandoned.

BRIEF SUMMARY OF THE INVENTION

The invention relates to tricyclic pyrrole derivatives of the formula

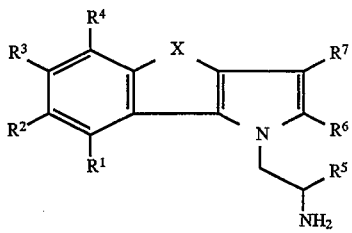

wherein $R^1$ to $R^4$ are, independently, hydrogen, halogen, lower alkyl, phenyl, cycloalkyl or lower alkoxy and $R^2$ additionally is lower alkoxycarbonyl, acyloxy or mesyloxy;

$R^5$ to $R^7$ are, independently, hydrogen or lower alkyl;

X is $-CH_2CH(C_6H_5)-$, $-CH=C(C_6H_5)-$, $-YCH_2-$, $-CH=CH-$ or $-(CR^{11}R^{12})_n$;

$R^{11}$ and $R^{12}$ are, independently, hydrogen, phenyl, lower alkyl or halogen;

n is 1 to 3 and

Y is O or S, as well as pharmaceutically acceptable acid addition salts of basic compounds of formula I with pharmaceutically acceptable acids.

The compounds of formula I and salts thereof are distinguished by their valuable pharmacological properties.

The compounds of formula I and the pharmaceutically acceptable salts thereof are useful in the control or prevention of illnesses or in the improvement of health, especially in the control or prevention of central nervous disorders, such as, depression. The compounds of formula I and their pharmaceutically acceptable salts can also be used for the treatment of bipolar disorders, anxiety states, sleep and sexual disorders, psychoses, schizophrenia, migraine and other conditions associated with cephalic pain or pain of a different kind, personality disorders or obsessive-compulsive disorders, social phobias or panic states, mental organic disorders, mental disorders in childhood, aggressivity, age-related memory disorders and behavioral disorders, addiction, obesity, bulimia, and the like; damages of the nervous system by trauma, stroke, neurodegenerative diseases, and the like; cardiovascular disorders such as hypertension, thrombosis, stroke and the like; and gastrointestinal disorders such as dysfunction of the gastrointestinal tract motility and, respectively, for the preparation of the corresponding medicaments.

In another aspect the invention relates to compounds of the formula

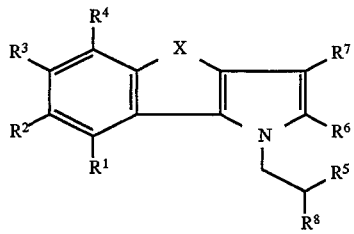

wherein $R^1$ to $R^7$ and X have the significances given above and $R^8$ is a residue convertible into an amino group or a hydroxy group.

DETAILED DESCRIPTION OF THE INVENTION

The invention relates to tricyclic pyrrole derivatives of the formula

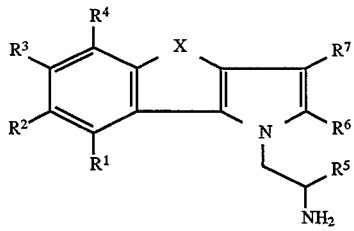

wherein $R^1$ to $R^4$ are, independently, hydrogen, halogen, lower alkyl, phenyl, cycloalkyl or lower alkoxy and $R^2$ additionally is lower alkoxycarbonyl, acyloxy or mesyloxy;

$R^5$ to $R^7$ are, independently, hydrogen or lower alkyl;

X is $-CH_2CH(C_6H_5)-$, $-CH=C(C_6H_5)-$, $-YCH_2-$, $-CH=CH-$ or $-(CR^{11}R^{12})_n$;

$R^{11}$ and $R^{12}$ are, independently, hydrogen, phenyl, lower alkyl or halogen;

n is 1 to 3 and

Y is O or S, as well as pharmaceutically acceptable acid addition salts of basic compounds of formula I with pharmaceutically acceptable acids.

The compounds of formula I and salts thereof are distinguished by their valuable pharmacological properties.

Objects of the invention are compounds of formula I and pharmaceutically acceptable salts thereof and as pharmaceutically active substances, the preparation of the compounds of formula I and their salts, medicaments which contain the compounds of formula I and their salts and the preparation of these medicaments, as well as the use of compounds of formula I and of pharmaceutically acceptable salts thereof in the control or prevention of illnesses or in the improvement of health, especially in the control or prevention of central nervous disorders, such as, depression. The compounds of formula I and their pharmaceutically acceptable salts can also be used for the treatment of bipolar disorders, anxiety states, sleep and sexual disorders, psychoses, schizophrenia, migraine and other conditions associated with cephalic pain or pain of a different kind, personality disorders or obsessive-compulsive disorders, social phobias or panic states, mental organic disorders, mental disorders in childhood, aggressivity, age-related memory disorders and behavioral disorders, addiction, obesity, bulimia, and the like; damages of the nervous system by trauma, stroke, neurodegenerative diseases, and the like; cardiovascular disorders such as hypertension, thrombosis, stroke and the like; and gastrointestinal disorders such as dysfunction of the gastrointestinal tract motility and, respectively, for the preparation of the corresponding medicaments.

Furthermore, the compounds of the formula

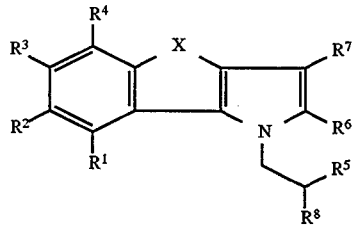

II wherein $R^1$ to $R^7$ and X have the significances given above and $R^8$ is a residue convertible into an amino group or a hydroxy group, are also objects of the invention.

The compounds of formula II are important intermediates for the preparation of the pharmaceutically valuable compounds of formula I.

As used herein, the term "lower" denotes residues with a maximum of 7, preferably up to 4, carbon atoms, "alkyl" denotes straight-chain or branched, saturated hydrocarbon residues, such as, methyl, ethyl, propyl, isopropyl or t-butyl, and "alkoxy" denotes an alkyl group attached via an oxygen atom, "halogen" is Cl, Br, F or I.

The term "pharmaceutically acceptable acid addition salts" denotes salts with inorganic and organic acids, such as, hydrochloric acid, hydrobromic acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

$R^5$ can conveniently be lower-alkyl, preferably methyl.

Compounds in which $R^5$ is hydrogen are also preferred.

When $R^5$ is methyl, compounds in which $R^1$, $R^3$ and $R^4$ are hydrogen and $R^2$ is halogen, lower alkyl or methoxy are especially preferred.

Some particularly preferred representatives of the class of compounds of formula I of the invention are:

(S)-2-(4,4,7-Trimethyl-1,4-dihydro-indeno[1,2-b]pyrrol-1-yl)-1-methyl-ethylamine;

(S)-2-(7-methoxy-4,4-dimethyl-1,4-dihydro-indeno[1,2-b]pyrrol-1-yl)-1-methyl-ethylamine;

(S)-2-(7-ethyl-4,4-dimethyl-1,4-dihydro-indeno[1,2-b]pyrrol-1-yl)-1-methyl-ethylamine;

(S)-2-(7-methyl-1,4-dihydro-indeno[1,2-b]pyrrol-1-yl)-1-methyl-ethylamine;

(S)-2-(7-brom-1,4-dihydro-indeno[1,2-b]pyrrol-1-yl)-1-methyl-ethylamine;

(S)-2-(7-methoxy-1,4-dihydro-indeno[1,2-b]pyrrol-1-yl)-1-methyl-ethylamine;

(S)-2-(7-chloro-1,4-dihydro-indeno[1,2-b]pyrrol-1-yl)-1-methyl-ethylamine; and (S)-2-(8-methoxy-1H-benz[g]indol-1-yl)-1-methyl-ethylamine.

The compound of formula I as well as their pharmaceutically acceptable salts can be prepared in accordance with the invention by a) converting a compound of the formula

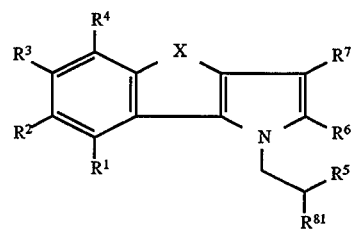

IIa wherein $R^1$ to $R^7$ and X have the significances given above and $R^{81}$ is a residue convertible into an amino group, into a corresponding amino compound and b) if desired, converting the resulting compound of formula I obtained into a pharmaceutically acceptable acid addition salt.

The compounds of formula IIa in which $R^{81}$ is a residue convertible into an amino group, preferably an azido group, an acetylamino group or another protected amino group, can be prepared according to known methods as described in more detail below. When the residue $R^{81}$ is an azido group, the preparation of the compounds of formula I is effected by reduction. This can be carried out, for example, with complex hydrides, such as, lithium aluminum hydride or by catalytic hydrogenation on metal catalysts, such as, platinum or palladium. When lithium aluminum hydride is used as the reducing agent, anhydrous ether or tetrahydrofuran is the most suitable solvent. Conveniently, the reduction can be carried out as follows: after the dropwise addition of a compound of formula IIa in which $R^{81}$ is an azido group to a solution consisting of the anhydrous solvent and the hydride. The resulting mixture is boiled at reflux, subsequently hydrolyzed with aqueous ether or THF solution and the aluminum hydroxide and lithium hydroxide. The precipitate is extracted with aqueous ether or THF solution.

The catalytic hydrogenation on metal catalysts, for example, platinum or palladium, is conveniently effected at room temperature. Especially suitable solvents for this purpose are water, alcohols, ethyl acetate, dioxan or mixtures of these solvents. The hydrogenation is effected under a hydrogen atmosphere, conveniently in an autoclave or in a shaking apparatus. When $R^{81}$ is an acetylamino group or another protected amino group, such as, trifluoromethylcarbonylamino, conversion into the corresponding amino compound is effected by hydrolysis.

The hydrolysis to the corresponding amino compounds of formula I is effected according to known methods. Metal hydroxides, for example, sodium hydroxide or potassium hydroxide, which hydrolyze to the compounds of formula I in the presence of water and a water-miscible organic solvent, such as, ethylene glycol or the like, are suitable for this purpose.

The conversion of the compounds of formula I into their corresponding acid addition salts is effected in the last operation, that is, after the hydrogenation or hydrolysis without isolating the resulting compound of formula I.

The fumaric acid salts are especially well suited for pharmaceutical use on stability grounds. However, all other acids mentioned in the description also form pharmacologically acceptable salts. The salt formation is effected at room temperature, alcohol-ether mixtures are especially suitable as the solvent.

The preparation of the intermediates of formula II, which are required for the synthesis of the compounds of formula I, is presented in Scheme 1. In this Scheme, all substituents $R^1$ to $R^4$ have the significances given in formula I. $R^{51}$, $R^{61}$ and $R^{71}$ are methyl. Me signifies methyl and Ac signifies acetyl. X likewise has the significance given in formula I, except —CH=CH—. The preparation of corresponding compounds in which X is —CH=CH— is shown in Scheme 2.
SCHEME 1
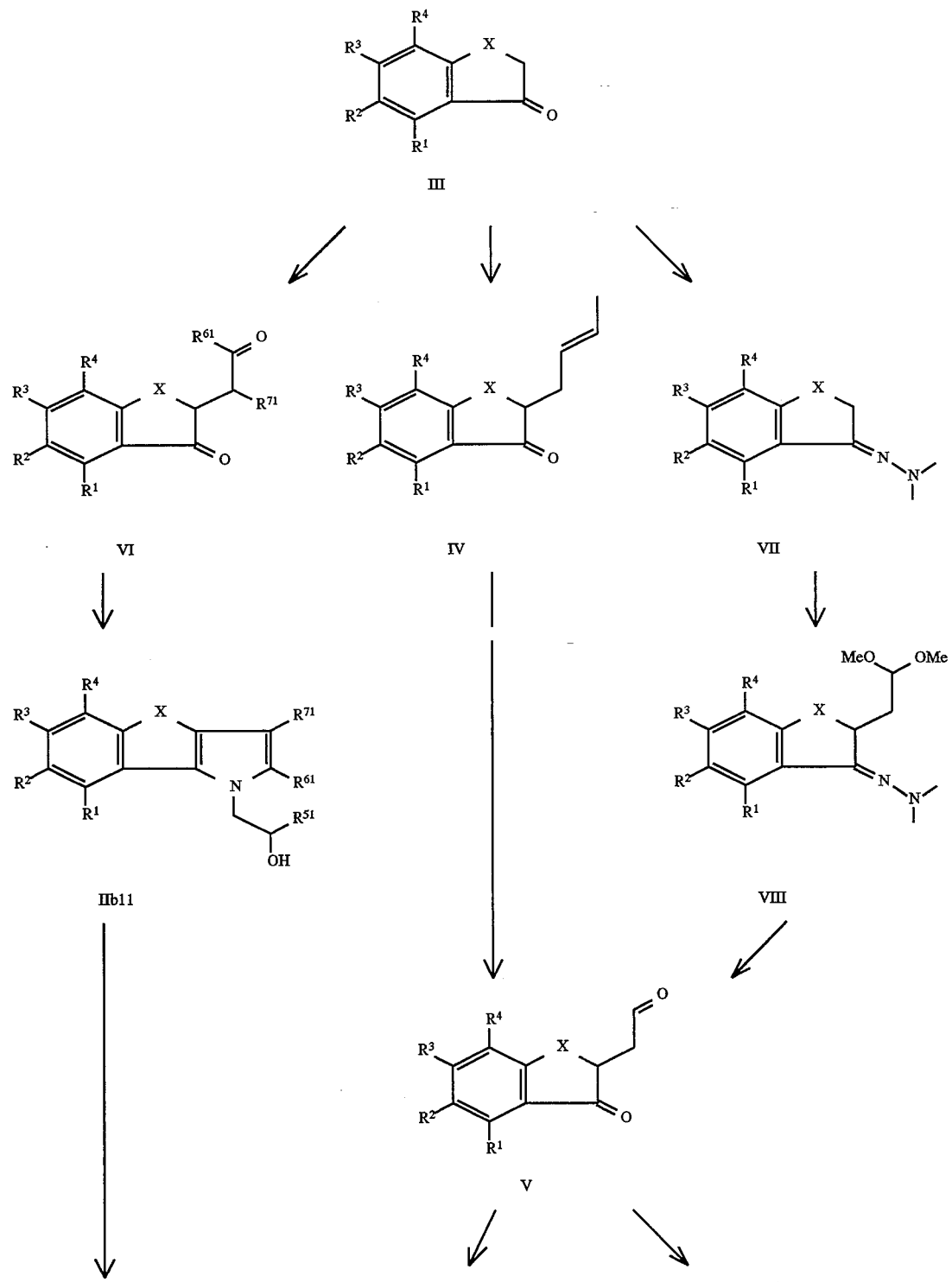

-continued
SCHEME 1

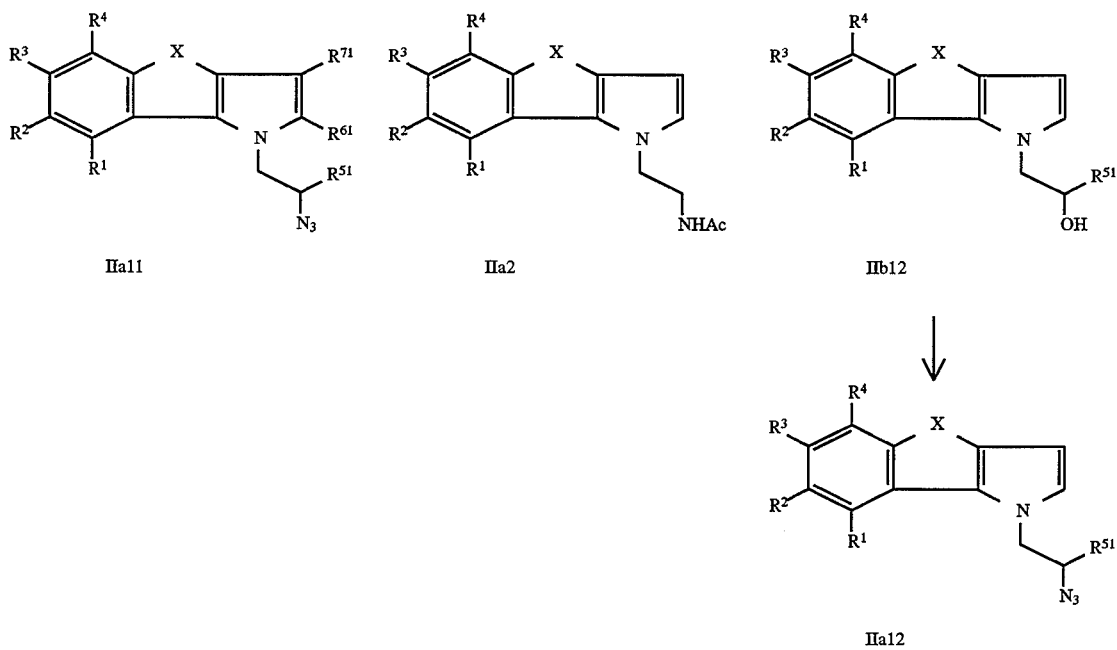

The preparation of the compounds of IIa2 starting from compound III is conveniently effected as follows:

A compound of formula III is heated under reflux with 3-buten-2-ol, 2,2-dimethoxypropane and catalytic amounts of p-toluenesulfonic acid in anhydrous toluene. In another variant, 2,2-dimethoxypropane replaces toluene as the solvent. In this case, the reaction mixture is heated at reflux on a water separator which is filled with molecular sieve. Subsequently, the thus-obtained compounds of formula IV are converted into the corresponding oxo-ethyl compounds. For this purpose, a compound IV is dissolved in an anhydrous solvent, for example, dichloromethane and methanol, and treated with a stream of ozone at about −70° C. The compound of formula V can then be cyclized to the pyrroleacetamino compounds. Conveniently, N-acetylethylenediamine is used and toluene or acetic acid is used as the solvent. After reaction and purification have been carried out, the acetyl group can be cleaved off as described and the compound of formula IIa2 can be converted into a compound of formula I.

A hydroxy compound of formula IIb12 conveniently results starting from the corresponding compound of formula V by cyclization with 1-amino-2-propanol in anhydrous toluene with catalytic amounts of p-toluenesulfonic acid by heating on a water separator. Subsequently, the hydroxy group can be converted into a leaving group according to known methods, for example, by conversion with a sulfonic acid chloride, preferably methanesulfonyl chloride, into the sulfonate. By treatment with an azide, preferably sodium azide, in a polar solvent, such as, DMF, a resulting compound of formula IIb12 can be converted into the corresponding azido compound of formula IIa12 which, as described, can be converted by reduction of the azido group into the compound of formula I.

The compounds of formula V can also be prepared by another route in accordance with Scheme 1.

A compound of formula III is conveniently heated with N,N-dimethylhydrazine under argon and then distilled over a Vigreux column. The compound of formula VII obtained is treated with DMPU (1,3-dimethyl-3,4,5,6-tetrahydro-2(1H)-pyrimidinone) and dissolved in anhydrous THF, cooled to about −75° C. and subsequently treated with n-butyllithium in hexane as well as bromoacetaldehyde dimethyl acetal.

The resulting compound of formula VIII is subsequently converted into the compound of formula V, after which an addition of phosphate buffer and copper(II) chloride dihydrate in THF is effected.

Compounds of formula IIb11 can also be prepared according to Scheme 1. These compounds can then be converted as described into the compounds of formula I. Conveniently, the following procedure can be followed: a compound of formula III dissolved in anhydrous THF is treated with diisopropylamine and n-butyllithium and subsequently treated with chloroacetone or 3-chloro-2-butanone. The resulting compounds VI are heated on a water separator in anhydrous toluene with catalytic amounts of p-toluenesulfonic acid. Treatment with 1-amino-2-propanol then leads to the compounds of formula IIb11.

Scheme 2 shows the preparation of compounds of formula IIa22 in which $R^1$ to $R^7$ have the significances given above and X signifies —CH=CH—. $R^{10}$ can be a methyl or trifluoromethyl group.

SCHEME 2

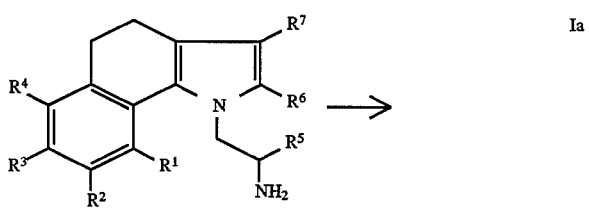

-continued
SCHEME 2

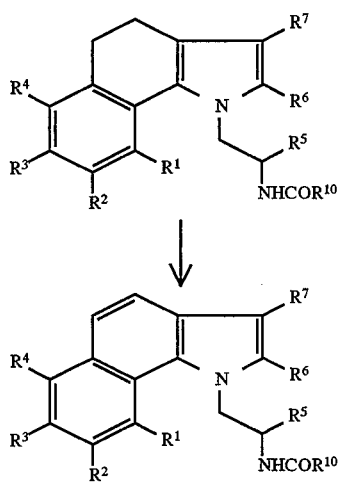

The following procedure is conveniently followed:

A compound of formula Ia is reacted in a solution consisting of triethylamine and ethyl trifluoroacetate in an anhydrous solvent, preferably methanol, and after drawing off the solvent the residue is taken up in dioxane and treated with DDQ (2,3-dichloro-5,6-dicyano-1,4-benzoquinone). Subsequently, the protecting group can be cleaved off from the amino group as described.

As mentioned earlier, the compounds of formula I and their pharmaceutically acceptable salts possess valuable pharmacological properties. They have the capacity to bind to serotonin receptors and are accordingly suitable for the treatment or prevention of illnesses or disorders of the kind referred to earlier and, respectively, for the manufacture of corresponding medicaments.

The binding of the compounds of formula I in accordance with the invention to serotonin receptors was determined in vitro by standard methods. The preparations were investigated in accordance with the assays given hereinafter:

Method I a) For the binding to the 5HT$_{1A}$ receptor in accordance with the $^3$H-8-OH-DPAT binding assay according to the method of S. J. Peroutka, Biol. Psychiatry 20, 971–979 (1985).

b) For the binding to the 5HT$_{2C}$ receptor in accordance with the $^3$H-mesulergine binding assay according to the method of A. Pazos et al., Europ. J. Pharmacol. 106, 539–546 or. D. Hoyer, Receptor Research 8, 59–81 (1988).

c) For the binding to the 5HT$_{2A}$ receptor in accordance with the $^3$H-ketanserine binding assay according to the method of J. E. Leysen, Molecular Pharmacology 21, 301–304 (1981).

The IC$_{50}$ values of the test substances were determined, that is, the concentration in nm by which 50% of the receptor-bound ligands are displaced.

The thus-determined activity of some compounds of formula I of the invention as well as those of some comparative compounds will be evident from the following Table:

| | Test methods | | |
|---|---|---|---|
| | a | b | c |
| Buspirone | 19.50 | 3700.0 | 990.0 |
| NAN-190 | 0.56 | 1800.0 | 581.0 |
| 5HT | 1.50 | 9.5 | 1730.0 |
| Metergoline | 4.80 | 5.5 | 64.9 |
| mCPP | 227.00 | 53.0 | 319.0 |
| RU 24969 | 8.0 | 159.0 | 2500.0 |
| CP 93129 | 1620.00 | 2780.0 | 29200.0 |
| Ritanserine | 5750.00 | 37.0 | 3.1 |
| Pirenperone | 2879.00 | 37.0 | 2.9 |
| 3 | 2830 | 11.4 | 2160 |
| 4 | 3230 | 49.3 | 2170 |
| 5 | 2560 | 20.2 | 591 |
| 7 | 2160 | 24.0 | 1200 |
| 21 | 1350 | 56.6 | 2540 |
| 22 | 1590 | 30.4 | 1400 |
| 23 | 347 | 45.2 | 3340 |
| 28 | 1070 | 78.7 | 1630 |
| 30 | 298 | 58.1 | 479 |
| 31 | 337 | 28.1 | 874 |
| 32 | 139 | 18.0 | 1666 |
| 34 | 1620 | 107.0 | 2640 |
| 53 | 1100 | 308.0 | 11300 |
| 54 | 825 | 116.0 | 2590 |
| 55 | 1260 | 371.0 | 8350 |
| 59 | 97 | 23.8 | 1510 |
| 64 | 384 | 85.4 | 773 |
| 67 | 1750 | 146.0 | 1070 |
| 69 | 3460 | 143.0 | 854 |

3 = (S)-2-(7-methoxy-1,4-dihydro-indeno[1,2-b]pyrrol-1-yl)-1-methyl-ethylamine.
4 = (S)-2-(7-chloro-1,4-dihydro-iindeno[1,2-b]pyrrol-1-yl)-1-methyl-ethylamine.
5 = (S)-2-(8-methoxy-4,5-dihydro-1H-benz[g]indol-1-yl)-1-methyl-ethylamine.
7 = (S)-2-(8-methoxy-1H-benz[g]indol-1-yl)-1-methyl-ethylamine.
21 = (RS)-2-(7-chloro-1,4-dihydro-indeno[1,2-b]pyrrol-1-yl)-1-methyl-ethylamine.
22 = (RS)-2-(7-methoxy-1,4-dihydro-indeno[1,2-b]pyrrol-1-yl)-1-methyl-ethylamine.
23 = 2-(7-methoxy1,4-dihydro-indeno[1,2-b]pyrrol-1-yl)-ethylamine.
28 = (R)-2-(7-methoxy-1,4-dihydro-indeno[1,2-b]pyrrol-1-yl)-1-methyl-ethylamine.
30 = (R)-2-(8-methoxy-4,5-dihydro-1H-benz[g]indol-1-yl)-1-methyl-ethylamine.
31 = (R)-2-(8-methoxy-1H-benz[g]indol-1-yl)-1-methyl-ethylamine.
32 = 2-(8-methoxy-1H-benz[g]indol-1-yl)-ethylamine.
34 = (RS)-1-(1,4-dihydro[1]benzopyrano[4,3-b]pyrrol-1-yl)-1-methyl-ethylamine.
53 = (RS)-2-(6-chloro-1,4-dihydro-indeno[1,2-b]pyrrol-1-yl)-1-methyl-ethylamine.
54 = (RS)-1-(8-methoxy-1,4-dihydro[1]benzopyrano[4,3-b]pyrrol-1-yl)-1-methyl-ethylamine.
55 = (RS)-2-(6-methoxy-1,4-dihydro-indeno[1,2-b]pyrrol-1-yl)-1-methyl-ethylamine.
59 = 2-(8-methoxy-4,5-dihydro-1H-benz[g]indol-1-yl)-ethylamine.
64 = (RS)-1-(1,4-dihydro[1]benzothiopyrano[4,3-b]pyrrol-1-yl)-1-methyl-ethylamine.
67 = (RS)-2-(8-methoxy,1,4-dihydro-indeno[1,2-b]pyrrol-1-yl)-1-methyl-ethylamine.
69 = (2RS/4RS)-2-(4-phenyl-1,4-dihydro-indeno[1,2-b]pyrrol-1-yl)-1-methyl-ethylamine.

Method II a) Displacement tests with [3H]-5-HT(1 nM) as the radioligand on recombinant human-5HT$_{1A}$ receptors expressed in 3T3 cells of mice were carried out in order to determine the affinity of a compound to the 5HT$_{1A}$ receptor. Membranes which had been obtained from 2×10$^5$ cells were used as were various concentrations of the respective test compound.

b) For the binding to the 5HT$_{2C}$ receptor in accordance with the [3H]-5-HT binding assay according to the method of S. J. Peroutka et al., Brain Research 584, 191–196 (1992).

c) For the binding to the $5HT_{2A}$ receptor in accordance with the [3H]-DOB binding assay according to the method of T. Branchek et al., Molecular Pharmacology 38, 604–609 (1990).

The $p_{ki}$ values ($p_{ki}=-\log^{10} Ki$) of the test substances are given. The ki value is defined by the following formula:

$$Ki = \frac{IC_{50}}{1+\frac{[L]}{K_D}}$$

in which the $IC_{50}$ values are those concentrations of test compounds in nm by which 50% of the receptor-bound ligands are displaced. [L] is the concentration of ligand and the KD value is the dissociation constant of the ligand.

The thus-determined activity of some compounds in accordance with the invention will be evident from the following Table:

|    | Test method | | |
| --- | --- | --- | --- |
|    | a | b | c |
| 1  | 5.66 | 8.49 | 7.27 |
| 2  | 5.39 | 9.44 | 8.03 |
| 3  |      | 8.16 | 7.12 |
| 8  | 5.34 | 8.63 | 7.18 |
| 9  | 5.56 | 8.29 | 7.46 |
| 12 | 5.00 | 8.00 | 6.94 |
| 14 | 5.00 | 7.78 | 7.62 |
| 17 | 5.00 | 7.74 | 6.25 |
| 25 | 5.00 | 7.38 | 6.26 |
| 26 | 5.25 | 7.58 | 7.17 |
| 37 | 5.32 | 7.45 | 6.51 |
| 44 | 5.73 | 7.10 | 6.57 |
| 50 | 5.62 | 6.97 | 6.35 |

1 = (S)-2-(4,4,7-Trimethyl-1,4-dihydro-indeno[1,2-b]pyrrol-1-yl)-1-methyl-ethylamine fumarate (1:1).
2 = (S)-2-(7-Methoxy-4,4-dimethyl-1,4-dihydro-indeno-[1,2-b]pyrrol-1-yl)-1-methyl-ethylamine fumarate (1:1).
8 = (S)-2-(7-Ethyl-4,4-dimethyl-1,4-dihydro-indeno-[1,2-b]pyrrol-1-yl)-1-methyl-ethylamine fumarate (1:1).
9 = (S)-2-(7-FLuor-4,4-dimethyl-1,4-dihydro-indeno[1,2-b]pyrrol-1-yl)-1-methyl-ethylamine fumarate (1:1).
12 = (S)-2-(7-Methoxy-4,4-diethyl-1,4-dihydro-indeno-[1,2-b]pyrrol-1-yl)-1-methyl-ethylamine fumarate (1:0.5).
14 = (S)-2-(7-Phenyl-1,4-dihydro-indeno[1,2-b]pyrrol-1-yl)-1-methyl-ethylamine fumarate (1:0.5).
17 = (S)-2-(7-Ethyl-1,4-dihydro-indeno[1,2-b]pyrrol-1-yl)-1-methyl-ethylamine fumarate (1:0.5).
25 = (S)-2-(6,7-Difluoro-1,4-dihydro-indeno[1,2-b]pyrrol-1-yl)-1-methyl-ethylamine fumarate (1:0.5).
26 = (S)-2-(6-chloro-7-methoxy-4,4-dimethyl-1,4-dihydro-indeno[1,2-b]pyrrol-1-yl)-1-methyl-ethylamine-fumarate (1:0.5).
37 = (RS)-2-(5-chloro-1,4-dihydro-indeno[1,2-b]pyrrol-1-yl)-1-methyl-ethylamine fumarat (1:0.5).
44 = (S)-1-Methyl-2-(7'-methyl-1',4'-dihydro-spiro[cyclo-pentane-1,4'-indeno[1,2-b]pyrrol]-1-yl)-ethylamine fumarate (1:1).
50 = (RS)-2-(5-Methyl-1,4-dihydro-indeno[1,2-b]pyrrol-1-yl)-1-methyl-ethylamine fumarate (1:0.5).

Penile erection (rats)

It has been shown that penile erection is dependent on the stimulation of the $5HT_{2C}$ receptor (see Berendsen & Broekkamp, Eur. J. Pharmacol, 135, 179–184 (1987)).

The number of penile erections was determined within 45 minutes following administration of the test substance to the animal. The $ED_{50}$ is that dosage which brings about 50% of these erections.

| Example No. | $ED_{50}$ (mg/kg, s.c.) |
| --- | --- |
| 1 | 0.90 |
| 2 | 0.50 |
| 3 | 1.20 |
| 4 | 2.70 |
| 5 | 3.20 |

The compounds of formula I and the pharmaceutically acceptable acid addition salts of the compounds of formula I can be used as medicaments, for example, in the form of pharmaceutical preparations. The pharmaceutical preparations can be administered orally, for example, in the form of tablets, coated tablets, dragées, hard and soft gelatin capsules, solutions, emulsions or suspensions. The administration can, however, also be effected rectally, for example, in the form of suppositories, parenterally, for example, in the form of injection solutions, or nasally.

For the preparation of pharmaceutical preparations, the compounds of formula I and the pharmaceutically acceptable acid addition salts of the compounds of formula I can be processed with pharmaceutically inert, inorganic or organic carriers. Lactose, corn starch or derivatives thereof, talc, stearic acid or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are, however, usually required in the case of soft gelatin capsules. Suitable carriers for the preparation of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances.

Medicaments containing a compound of formula I or a pharmaceutically acceptable acid addition salt thereof and a therapeutically inert carrier are also an object of the invention, as is a process for their preparation which comprises bringing one or more compounds of formula I and/or pharmaceutically acceptable acid addition salts thereof into a galenical administration form together with one or more therapeutically inert carriers.

The compounds of formula I and the pharmaceutically acceptable salts thereof are useful in the control or prevention of illnesses or in the improvement of health, especially in the control or prevention of central nervous disorders, such as, depression. The compounds of formula I and their pharmaceutically acceptable salts can also be used for the treatment of bipolar disorders, anxiety states, sleep and sexual disorders, psychoses, schizophrenia, migraine and other conditions associated with cephalic pain or pain of a different kind, personality disorders or obsessive-compulsive disorders, social phobias or panic states, mental organic disorders, mental disorders in childhood, aggressivity, age-related memory disorders and behavioral disorders, addiction, obesity, bulimia and the like; damages of the nervous system by trauma, stroke, neurodegenerative diseases and the like; cardiovascular disorders, such as, hypertension, thrombosis, stroke and the like; and gastrointestinal disorders, such as, dysfunction of the gastrointestinal tract motility and, respectively, for the preparation of the corresponding medicaments. The dosage can vary within wide limits and will, of course, be fitted to the individual requirements in each particular case. In the case of oral administration, the dosage lies in a range of about 0.01 mg per dose to about 500 mg per day of a compound of formula I or the corresponding amount of a pharmaceutically acceptable acid addition salt thereof, although the upper limit can also be exceeded when this is found to be indicated.

The following Examples further illustrate the invention. All temperatures are given in degrees celsius

EXAMPLE 1 a) A solution of 18.9 g of 3,3,6-trimethyl-1-indanone, 22.4 ml of 3-buten-2-ol and 300 mg of p-toluenesulfonic acid in 200 ml of 2,2-dimethoxy-propane was boiled under reflux for 64 hours on a water separator filled with molecular sieve (0.4 nm, 2 mm pearl shaped). The reaction mixture was subsequently concentrated in a vacuum and purified by column chromatography on silica gel (hexane/ethyl acetate 6:1). In addition to 4.5 g of educt, there were obtained 12.7 g (51%) of (RS)-2-(2-buten-1-yl)-3,3,6-trimethyl-1-indanone as a yellow oil b) An ozone stream (2.5 g ozone/hour) was conducted for 60 minutes while stirring through a solution, cooled to −70° of 12.7 g (RS)-2-(2-buten-1-yl)-3,3,6-trimethyl-1-indanone in 200 ml of anhydrous dichloromethane and 40 ml of anhydrous methanol. Subsequently, the solution was flushed with oxygen for 5 minutes and with argon for 10 minutes. After the addition of 6.12 ml of dimethyl sulfide, the mixture was stirred at room temperature for 18 hours. The reaction mixture was evaporated in a vacuum, the residue was treated with 150 ml of dichloromethane and, after the addition of 25 ml of water and 25 ml of trifluoroacetic acid, stirred at room temperature for 2.5 hours. The mixture was subsequently poured into 150 ml of water and neutralized by the spatula-wise addition of sodium hydrogen carbonate while stirring. An additional 100 ml of water were added. The phases were separated and the aqueous phase was extracted twice with 150 ml of dichloromethane each time. The combined organic phases were dried over magnesium sulfate and concentrated in a vacuum. 11.3 g (94%) of (RS)-2-(2-oxoethyl)-3,3,6-trimethyl-1-indanone were obtained as a light yellow oil.

c) A solution of 2.16 g of (RS)-2-(2-oxoethyl)-3,3,6-trimethyl-1-indanone and 80 ml of p-toluenesulfonic acid in 90 ml of anhydrous toluene was heated on a water separator. A solution of 3.0 g of (R)-1-amino-2-propanol in 20 ml of anhydrous toluene was added dropwise to the boiling solution over a period of 5 minutes. Subsequently, the mixture was boiled for an additional 45 minutes, during which the solvent was reduced to a volume of 20 ml. The cooled reaction mixture was purified by column chromatography on silica gel (ethyl acetate/hexane 1:2). 1.5 g (59%) of (R)-1-(4,4,7-trimethyl-1,4-dihydro-indeno[1,2-b]pyrrol-1-yl)-propano2-ol were obtained as a brown oil.

d) 0.91 ml of methanesulfonyl chloride was added dropwise while stirring to a solution, cooled to 0°, of 1.5 g of (R)-1-(4,4,7-trimethyl-1,4-dihydro-indeno[1,2-b]pyrrol-1-yl)-propan-2-ol and 3.27 ml of triethylamine in 50 ml of dichloromethane and the mixture was stirred at this temperature for an additional 1.5 hours. The reaction mixture was subsequently diluted with 150 ml of dichloromethane, washed twice with 70 ml of saturated sodium hydrogen carbonate solution each time and the combined aqueous phases were extracted once with 70 ml of dichloromethane. The combined organic phases were washed with 70 ml of saturated sodium chloride solution, dried over magnesium sulfate and evaporated in a vacuum. The green solid obtained was dissolved in 50 ml of anhydrous dimethylformamide, treated with 0.76 g of sodium azide and the reaction mixture was heated to 60° for 15 hours while stirring. After cooling the solution was poured into 100 ml of water and extracted twice with 100 ml of ethyl acetate each time. The combined organic phases were washed once with 100 ml of water and once with 100 ml of saturated sodium chloride solution, dried over magnesium sulfate and the solution was concentrated in a vacuum. The brown oil obtained was purified by column chromatography on silica gel (hexane/ethyl acetate 4:1). 1.13 g (68%) of (S)-1-(2-azido-propyl)-4,4,7-trimethyl-1,4-dihydro-indeno[1,2-b]pyrrole were obtained as a reddish oil.

e) 1.1 g of (S)-1-(2-azido-propyl)-4,4,7-trimethyl-1,4-dihydro-indeno[1,2-b]pyrrole dissolved in 50 ml of anhydrous ethanol were hydrogenated on 110 mg of platinum oxide for 4 hours. The catalyst was subsequently filtered off, rinsed with ethanol and the solvent was drawn off in a vacuum. The colorless oil obtained was dissolved in 80 ml of anhydrous diethyl ether, filtered and treated while stirring with a solution of 455 mg of fumaric acid in 15 ml of methanol. The mixture was stirred at room temperature for 24 hours and the white crystals were subsequently filtered off. 805 mg (77%) of (S)-2-(4,4,7-trimethyl-1,4-dihydro-indeno[1,2-b]pyrrol-1-yl)-1-methyl-ethylamine fumarate (1:1) with m.p. 196° were obtained.

EXAMPLE 2 a) A solution of 12.1 g of 6-methoxy-3,3-dimethyl-1-indanone, 11.1 ml of 3-buten-2-ol and 110 mg of p-toluenesulfonic acid in 110 ml of 2,2-dimethoxy-propane was boiled under reflux for 67 hours on a water separator filled with molecular sieve (0.4 nm, 2 mm pearl shaped). The reaction mixture was subsequently concentrated in a vacuum and purified by column chromatography on silica gel (hexane/diethyl ether 4:1). In addition to 4.64 g of educt, there were obtained 5.86 g (38%) of (RS)-2-(2-buten-1-yl)-6-methoxy-3,3-dimethyl-1-indanone as a yellow oil.

b) An ozone stream (3 g ozone/hour) was conducted for 40 minutes while stirring through a solution, cooled to −70°, of 5.86 g of (RS)-2-(2-buten-1-yl)-6-methoxy-3,3-dimethyl-1-indanone in 100 ml of anhydrous dichloromethane and 20 ml of anhydrous methanol. Subsequently, the solution was flushed with oxygen for 5 minutes and with argon for 10 minutes. After the addition of 2.64 ml of dimethyl sulfide the mixture was stirred at room temperature for 4 hours. The reaction mixture was evaporated in a vacuum. The residue was treated with 60 ml of dichloromethane and, after the addition of 10 ml of water and 10 ml of trifluoroacetic acid, stirred at room temperature for 2 hours. The mixture was subsequently poured into 100 ml of water and neutralized by the spatula-wise addition of sodium hydrogen carbonate while stirring An additional 50 ml of water were added. The phases were separated and the aqueous phase was extracted twice with 150 ml of dichloro-methane each time. The combined organic phases were dried over magnesium sulfate and concentrated in a vacuum. 4.94 g (89%) of (RS)-2-(2-oxoethyl)-6-methoxy-3,3-dimethyl-1-indanone were obtained as a light yellow oil.

c) A solution of 4.94 g of (RS)-2-(2-oxoethyl)-6-methoxy-3,3-dimethyl-1-indanone and 220 ml of p-toluenesulfonic acid in 200 ml of anhydrous toluene was heated on a water separator. A solution of 6.39 g of (R)-1-amino-2-propanol in 40 ml of anhydrous toluene was added dropwise to the boiling solution over a period of 5 minutes, during which the solvent was reduced to a volume of 40 ml. The cooled reaction mixture was purified by column chromatography on silica gel (diethyl ether/hexane 7:3). 3.42 g (60%) of (R)-1-(7-methoxy-4,4-dimethyl-1,4-dihydro-indeno[1,2-b]pyrrol-1-yl)-propan-2-ol were obtained as a brown oil.

d) 2.0 ml of methanesulfonyl chloride were added dropwise while stirring to a solution, cooled to 0°, of 3.42 g of (R)-1-(7-methoxy-4,4-dimethyl-1,4-dihydro-indeno[1,2-b]pyrrol-1-yl)-propan-2-ol and 7.3 ml of triethylamine in 70 ml of dichloromethane, and the mixture was stirred at this temperature for an additional 1.5 hours. The reaction mixture was subsequently diluted with 170 ml of dichloromethane, washed twice with 90 ml of saturated sodium hydrogen carbonate solution each time and the combined aqueous phases were extracted once with 70 ml of dichloromethane. The combined organic phases were washed with 90 ml of saturated sodium chloride solution, dried over magnesium sulfate and evaporated in a vacuum. The green oil obtained was dissolved in 70 ml of anhydrous dimethylformamide, treated with 1.35 g of sodium azide and the reaction mixture was heated to 60° for 20 hours while stirring. After cooling, the solution was poured into 100 ml of water and extracted three times with 100 ml of ethyl acetate each time. The combined organic phases were washed once with 100 ml of water and once with 100 ml of saturated sodium chloride solution, dried over magnesium sulfate and the solution was concentrated in a vacuum. The brown oil obtained was purified by column chromatography on silica gel (hexane/ethyl acetate 4:1). 1.89 g (50%) of (S)-1-(2-azido-propyl)-7-methoxy-4,4-dimethyl-1,4-dihydro-indeno[1,2-b]pyrrole were obtained as a yellow oil.

e) 1.89 g of (S)-1-(2-azido-propyl)-7-methoxy-4,4-dimethyl-1,4-dihydro-indeno[1,2-b]pyrrole dissolved in 100 ml of anhydrous ethanol were hydrogenated on 190 mg of platinum oxide for 2 hours. The catalyst was subsequently filtered off, rinsed with ethanol and the solvent was drawn off in a vacuum. The colorless oil obtained was dissolved in 100 ml of anhydrous diethyl ether, filtered and treated with a solution of 740 mg of fumaric acid in 15 ml of methanol. The mixture was stirred at room temperature for 15 hours and the white crystals were subsequently filtered off. 1.46 g (60%) of (S)-2-(7-methoxy-4,4-dimethyl-1,4-dihydro-indeno[1,2-b]pyrrol-1-yl)-1-methyl-ethylamine fumarate (1:1) with m.p. 181° were obtained.

EXAMPLE 3 a) A solution of 9.3 g of 6-methoxy-1-indanone, 11.8 ml of 3-buten-2-ol and 100 mg of p-toluenesulfonic acid in 100 ml of 2,2-dimethoxypropane was boiled under reflux for 64 hours on a water separator filled with molecular sieve (0.4 nm, 2 mm pearl shaped). The reaction mixture was subsequently concentrated in a vacuum and purified by column chromatography on silica gel (hexane/diethyl ether 4:1). 9.2 g (74%) of (RS)-2-(2-buten-1-yl)-6-methoxy-1-indanone were obtained as a yellow oil.

b) An ozone stream (3 g ozone/hour) was conducted for 80 minutes while stirring through a solution, cooled to −70°, of 15.2 g of (RS)-2-(2-buten-1-yl)-6-methoxy-1-indanone in 250 ml of anhydrous dichloromethane and 50 ml of anhydrous methanol. Subsequently, the solution was flushed with oxygen for 5 minutes and with argon for 10 minutes. After the addition of 7.75 ml of dimethyl sulfide, the mixture was stirred at room temperature for 15 hours. The reaction mixture was evaporated in a vacuum, the residue was treated with 250 ml of dichloromethane and, after the addition of 25 ml of water and 25 ml of trifluoroacetic acid, stirred at room temperature for 3 hours. The mixture was subsequently poured into 150 ml of water and neutralized while stirring by the spatula-wise addition of sodium hydrogen carbonate. An additional 100 ml of water were added, the phases were separated and the aqueous phase was extracted twice with 150 ml of dichloromethane each time. The combined organic phases were dried over magnesium sulfate, concentrated in a vacuum and the crude product obtained was crystallized from diethyl ether/hexane. 12 g (83%) of (RS)-2-(2-oxoethyl)-6-methoxy-1-indanone were obtained as a light yellow solid with m.p. 59°.

c) A solution of 2 g of (RS)-2-(2-oxoethyl)-6-methoxy-1-indanone and 80 mg of p-toluenesulfonic acid in 70 ml of anhydrous toluene was heated on a water separator. A solution of 2.94 g of (R)-1-amino-2-propanol in 20 ml of anhydrous toluene was added dropwise to the boiling solution over a period of 5 minutes. Subsequently, the mixture was boiled for an additional 30 minutes, during which the solvent was reduced to a volume of 20 ml. The cooled reaction mixture was purified by column chromatography on silica gel (ethyl acetate/toluene 1:1). 1.5 g (63%) of (R)-1-(7-methoxy-1,4-dihydro-indeno[1,2-b]pyrrol-1-yl)-propan-2-ol were obtained as a solid with m.p. 75°.

d) 0.96 ml of methanesulfonyl chloride was added dropwise while stirring to a solution, cooled to 0°, of 1.5 g of (R)-1-(7-methoxy-1,4-dihydro-indeno[1,2-b]pyrrol-1-yl)-propan-2-ol and 3.45 ml of triethylamine in 50 ml of dichloromethane and the mixture was stirred at this temperature for an additional 1.5 hours. The reaction mixture was subsequently diluted with 200 ml of diethyl ether, washed twice with 70 ml of saturated sodium hydrogen carbonate solution each time and the combined aqueous phases were extracted once with 70 ml of diethyl ether. The combined organic phases were washed with 70 ml of saturated sodium chloride solution, dried over magnesium sulfate and evaporated in a vacuum. The brown oil obtained was dissolved in 60 ml of anhydrous dimethylformamide, treated with 0.77 g of sodium azide and the reaction mixture was heated to 60° for 15 hours while stirring. After cooling, the solution was poured into 140 ml of water and extracted twice with 140 ml of diethyl ether each time. The combined organic phases were washed once with 100 ml of water and once with 100 ml of saturated sodium chloride solution, dried over magnesium sulfate and the solution was concentrated in a vacuum. The brown oil obtained was purified by column chromatography on silica gel (toluene). 1.0 g (60%) of (S)-1-(2-azido-propyl)-7-methoxy-1,4-dihydro-indeno[1,2-b]pyrrole was obtained as a colorless oil.

e) 1 g of (S)-1-(2-azido-propyl)-7-methoxy-1,4-dihydro-indeno[1,2-b]pyrrole dissolved in 50 ml of anhydrous ethanol was hydrogenated on 100 mg of platinum oxide for 4 hours. The catalyst was subsequently filtered off, rinsed with ethanol and the solvent was drawn off in a vacuum. The colorless oil obtained was dissolved in 100 ml of anhydrous ether, filtered and treated while stirring with a solution of 240 mg of fumaric acid in 20 ml of methanol. The mixture was stirred at room temperature for 18 hours and the white crystals were subsequently filtered off. 870 mg (77%) of (S)-2-(7-methoxy-1,4-dihydro-indeno[1,2-b]pyrrol-1-yl)-1-methyl-ethylamine fumarate (1:0.5) with m.p. 206° were obtained.

EXAMPLE 4 a) A solution of 20.2 g of 6-chloro-1-indanone, 25 ml of 3-buten-2-ol and 200 mg of p-toluenesulfonic acid in 25 ml of 2,2-dimethoxypropane and 200 ml of anhydrous toluene was boiled under reflux for 16 hours. The reaction mixture was subsequently concentrated in a vacuum and purified by column chromatography on silica gel (hexane/diethyl ether 5:1). 10.3 g (39%) of (RS)-2-(2-buten-1-yl)-6-chloro-1-indanone were obtained as a yellow oil.

b) An ozone stream (3 g ozone/hour) was conducted for 45 minutes while stirring through a solution, cooled to −70°, of 10.3 g of (RS)-2-(2-buten-1-yl)-6-chloro-1-indanone in 200 ml of anhydrous dichloro-methane and 100 ml of anhydrous methanol. Subsequently, the mixture was flushed with oxygen for 5 minutes and with argon for 10 minutes. After the addition of 5.13 ml of dimethyl sulfide, the mixture was stirred at room temperature for 16 hours. The reaction mixture was evaporated in a vacuum. The residue was treated with 60 ml of dichoromethane and, after the addition of 15 ml of water and 15 ml of trifluoroacetic acid, stirred at room temperature for 3 hours. The mixture was subsequently poured into 150 ml of water and neutralized by the spatula-wise addition of sodium hydrogen carbonate while stirring. An additional 100 ml of water were added, the phases were separated and the aqueous phase was extracted twice with 150 ml of dichloromethane each time. The combined organic phases were dried over magnesium sulfate, concentrated in a vacuum and the crude product obtained was recrystallized from ethyl acetate/hexane. 8.29 g (85%) of (RS)-2-(2-oxoethyl)-6-chloro-1-indanone were obtained as a white solid with m.p. 80°.

c) A solution of 2.5 g of (RS)-2-(2-oxoethyl)-6-chloro-1-indanone and 100 mg of p-toluenesulfonic acid in 120 ml of anhydrous toluene was heated on a water separator. A solution of 3.6 g of (R)-1-amino-2-propanol in 20 ml of anhydrous toluene was added dropwise to the boiling solution over a period of 5 minutes. Subsequently, the mixture was boiled for an additional 30 minutes, during which the solvent was reduced to a volume of 20 ml. The cooled reaction mixture was purified by column chromatography on silica gel (ethyl acetate/toluene 1:1). 2.42 g (81%) of (R)-1-(7-chloro-1,4-dihydro-indeno[1,2-b]pyrrol-1-yl)-propano2-ol were obtained, as a brown oil which was used directly in the next reaction.

d) 1.53 ml of methanesulfonyl chloride were added dropwise while stirring to a solution, cooled to 0°, of 2.42 g of (R)-1-(7-chloro-1,4-dihydro-indeno[1,2-b]pyrrol-1-yl)-propan-2-ol and 5.48 ml of triethylamine in 70 ml of dichloromethane and the mixture was stirred at this temperature for an additional 1.5 hours. The reaction mixture was subsequently diluted with 200 ml of diethyl ether, washed twice with 70 ml of saturated sodium hydrogen carbonate solution each time and the combined aqueous phases were extracted once with 70 ml of diethyl ether. The combined organic phases were washed with 70 ml of saturated sodium chloride solution, dried over magnesium sulfate and evaporated in a vacuum. The brown oil obtained was dissolved in 50 ml of anhydrous dimethylformamide, treated with 1.27 g of sodium azide and the reaction mixture was heated to 60° for 15 hours while stirring. After cooling, the solution was poured into 140 ml of water and extracted twice with 140 ml of diethyl ether each time and once with 70 ml of ethyl acetate. The combined organic phases were washed once with 100 ml of water and once with 100 ml of saturated sodium chloride solution, dried over magnesium sulfate and the solution was concentrated in a vacuum. The brown oil obtained was purified by column chromatography on silica gel (toluene). 1.5 g (56%) of (S)-1-(2-azido-propyl)-7-chloro-1,4-dihydro-indeno[1,2-b]pyrrole were obtained as an oil.

e) 1.5 g of (S)-1-(2-azido-propyl)-7-chloro-1,4-dihydro-indeno[1,2-b]pyrrole dissolved in 50 ml of anhydrous ethanol were hydrogenated on 150 mg of platinum oxide for 14 hours. The catalyst was subsequently filtered off, rinsed with ethanol and the solvent was drawn off in a vacuum. The colorless oil obtained was dissolved in 100 ml of anhydrous diethyl ether, filtered and treated while stirring with a solution of 306 mg of methanol. The mixture was stirred at room temperature for 3 hours and the white crystals were subsequently filtered off. 1.12 g (67%) of (S)-2-(7-chloro-1,4-dihydro-indeno[1,2-b]pyrrol-1-yl)-1-methyl-ethylamine fumarate (1:0.5) with m.p. 197° were obtained.

EXAMPLE 5 a) A solution of 2 g of (RS)-2-(2-oxoethyl)-7-methoxy-1-tetralone and 100 mg of p-toluenesulfonic acid in 90 ml of anhydrous toluene was heated on a water separator. A solution of 2.78 g of (R)-1-amino-2-propanol in 20 ml of anhydrous toluene was added dropwise to the boiling solution over a period of 5 minutes. Subsequently, the mixture was boiled for an additional 30 minutes, during which the solvent was reduced to a volume of 25 ml. The cooled reaction mixture was purified by column chromatography on silica gel (ethyl acetate/toluene 1:1). 2.25 g (94%) of (R)-1-(4,5-dihydro-8-methoxy-1H-benz[g]indol-1-yl)-propan-2-ol were obtained as a brown oil which was used directly in the next reaction.

b) 1.4 ml of methanesulfonyl chloride were added dropwise while stirring to a solution, cooled to 0° C., of 2.25 g of (R)-1-(4,5-dihydro-8-methoxy-1H-benz[g]indol-1-yl)-propan-2-ol and 5 ml of triethyl-amine in 60 ml of dichloromethane and the mixture was stirred at this temperature for an additional 1.5 hours. The reaction mixture was subsequently diluted with 300 ml of diethyl ether, washed twice with 100 ml of saturated sodium hydrogen carbonate solution and the combined aqueous phases were extracted once with 100 ml of diethyl ether. The combined organic phases were washed with 100 ml of saturated sodium chloride solution, dried over magnesium sulfate and evaporated in a vacuum. The brown oil obtained was dissolved in 50 ml of anhydrous dimethyl formamide, treated with 1.17 g of sodium azide and the reaction mixture was heated to 60° for 15 hours while stirring. After cooling, the solution was poured into 140 ml of water and extracted twice with 140 ml of diethyl ether each time. The combined organic phases were washed once with 100 ml of water and once with 100 ml of saturated sodium chloride solution, dried over magnesium sulfate and the solution was concentrated in a vacuum. The brown oil obtained was purified by column chromatography on silica gel (toluene). 1.78 g (71%) of (S)-1-(2-azido-propyl)-4,5-dihydro-8-methoxy-1H-benz[g]indole were obtained as a colorless oil.

c) 2.78 g of (S)-1-(2-azido-propyl)-4,5-dihydro-8-methoxy-1H-benz[g]indole dissolved in 100 ml of anhydrous ethanol were hydrogenated on 280 mg of platinum oxide for 16 hours. The catalyst was subsequently filtered off, rinsed with ethanol and the solvent was drawn off in a vacuum. 700 mg of the colorless oil obtained were dissolved in 100 ml of anhydrous diethyl ether, filtered and treated while stirring with a solution of 317 mg of fumaric acid in 20 ml of methanol. The mixture was stirred at room temperature for 2 hours and the white crystals were subsequently filtered off. 820 mg (81%) of (S)-2-(4,5-dihydro-8-methoxy-1H-benz[g]indol-1-yl)-1-methyl-ethylamine fumarate (1:1) with m.p. 193° were obtained.

EXAMPLE 6 a) A solution of 19.7 g of 6-fluoro-1-indanone, 27.0 ml of 3-buten-2-ol and 200 mg of p-toluenesulfonic acid in 200 ml of 2,2-dimethoxypropane was boiled under reflux for 67 hours on a water separator filled with molecular sieve (0.4 nm, 2 mm pearl shaped). The reaction mixture was subsequently concentrated in a vacuum and purified by column chromatography on silica gel (hexane/diethyl ether 4:1). 18.9 g (71%) of (RS)-2-(2-buten-1-yl)-6-fluoro-1-indanone were obtained as a yellow oil.

b) An ozone stream (3 g ozone/hour) was conducted for 100 minutes while stirring through a solution, cooled to −70°, of 18.9 g of (RS)-2-(2-buten-1-yl)-6-fluoro-1-indanone in 300 ml of anhydrous dichloro-methane and 60 ml of anhydrous methanol. Subsequently, the solution was flushed with oxygen for 5 minutes and with argon for 10 minutes. After the addition of 102 ml of dimethyl sulfide, the mixture was stirred at room temperature for 16 hours. The reaction mixture was evaporated in a vacuum, the residue was treated with 300 ml of dichloromethane and, after the addition of 43 ml of water and 43 ml of trifluoroacetic acid, stirred at room temperature for 3 hours. The mixture was subsequently poured into 200 ml of water and neutralized by the spatula-wise addition of sodium hydrogen carbonate while stirring. An additional 100 ml of water were added. The phases were separated and the aqueous phase was extracted twice with 200 ml of dichloromethane each time. The combined organic phases were dried over magnesium sulfate, concentrated in a vacuum and the crude product obtained was crystallized from diethyl ether/hexane. 16.5 g (92%) of (RS)-2-(2-oxo-ethyl)-6-fluoro-1-indanone were obtained as a white solid with m.p. 62°.

c) A solution of 1.92 g of (RS)-2-(2-oxo-ethyl)-6-fluoro-1-indanone and 80 mg of p-toluenesulfonic acid in 90 ml of anhydrous toluene was heated on a water separator. A solution of 3.0 g of (R)-1-amino-2-propanol in 20 ml of anhydrous toluene was added dropwise to the boiling solution over a period of 5 minutes. Subsequently, the mixture was boiled for an additional 30 minutes, during which the solvent was reduced to a volume of 20 ml. The cooled reaction mixture was purified by column chromatography on silica gel (ethyl acetate/toluene 1:1). 1.73 g (75%) of (R)-1-(7-fluoro-1,4-dihydro-indeno[1,2-b]pyrrol-1-yl)-propan-2-ol were obtained as a brown oil which was used without further purification in the next reaction.

d) 1.17 ml of methanesulfonyl chloride were added dropwise while stirring to a solution, cooled to 0°, of 1.73 g of (R)-1-(7-fluoro-1,4-dihydro-indeno[1,2-b]pyrrol-1-yl)-propan-2-ol and 4.2 ml of triethyl-amine in 60 ml of dichloromethane and the mixture was stirred at this temperature for an additional 1.5 hours. The reaction mixture was subsequently diluted with 150 ml of diethyl ether, washed twice with 60 ml of saturated sodium hydrogen carbonate solution each time and the combined aqueous phases were extracted once with 70 ml of diethyl ether. The combined organic phases were washed with 70 ml of saturated sodium chloride solution, dried over magnesium sulfate and evaporated in a vacuum. The brown oil obtained was dissolved in 50 ml of anhydrous dimethylformamide, treated with 973 mg of sodium azide and the reaction mixture was heated to 50° for 15 hours while stirring. After cooling, the solution was poured into 110 ml of water and extracted twice with 110 ml of diethyl ether each time and once with 60 ml of ethyl acetate. The combined organic phases were washed once with 80 ml of water and once with 80 ml of saturated sodium chloride solution, dried over magnesium sulfate and the solution was concentrated in a vacuum. The brown oil obtained was purified by column chromatography on silica gel (toluene). 750 mg (39%) of (S)-1-(2-azido-propyl)-7-fluoro-1,4-dihydro-indeno[1,2-b]pyrrole were obtained as a colorless oil.

e) 750 mg of (S)-1-(2-azido-propyl)-7-fluoro-1,4-dihydro-indeno[1,2-b]pyrrole dissolved in 40 ml of anhydrous ethanol were hydrogenated on 75 mg of platinum oxide for 15 hours. The catalyst was subsequently filtered off, rinsed with ethanol and the solvent was drawn off in a vacuum. The colorless oil obtained was dissolved in 100 ml of anhydrous diethyl ether, filtered and treated while stirring with a solution of 370 mg of fumaric acid in 20 ml of methanol. The mixture was stirred at room temperature for 3 hours and the white crystals were subsequently filtered off. 460 mg (54%) of (S)-2-(7-fluoro-1,4-dihydro-indeno[1,2-b] pyrrol-1-yl)-1-methyl-ethylamine fumarate (1:0.5) m.p. 194° were obtained.

EXAMPLE 7 a) A solution of 1.5 g of (S)-2-(4,5-dihydro-8-methoxy-1H-benz[g]indol-1-yl)-1-methyl-ethylamine, 0.74 g of triethylamine and 1.04 g of ethyl trifluoroacetate in 100 ml of anhydrous methanol was stirred at room temperature for 27 hours. After the solvent had been drawn off in a vacuum, the residue was taken up with 100 ml of ahydrous dioxane, 1.56 g of DDQ were added and the mixture was boiled under reflux for 1.5 hours. Subsequently, the reaction mixture was concentrated in a vacuum and the residue was purified by column chromatography on silica gel (dichloromethane/ acetone 4:1). 1.2 g (59%) of (S)-N-[2-(8-methoxy-1H-benz [g]indol-1-yl)-1-methyl-ethyl]-trifluoracetamide were obtained as a pale brown solid which was used in the next reaction without additional recrystallization.

b) A mixture of 1.2 g of (S)-N-[2-(8-methoxy-1H-benz [g]indol-1-yl)-1-methyl-ethyl]-trifluoracetamide, 1.2 g of potassium hydroxide in 3 ml of water and 50 ml of methanol was boiled under reflux for 3 hours. The reaction mixture was subsequently poured into 100 ml of 1N sodium hydroxide solution, extracted twice with 100 ml of diethyl ether each time and once with 100 ml of ethyl acetate, the combined organic phases were washed once with 150 ml and dried over magnesium sulfate. After concentration in a vacuum, the residue was dissolved in 100 ml of anhydrous diethyl ether, filtered and treated while stirring with a solution of 398 mg of fumaric acid in 30 ml of methanol. The mixture was stirred at room temperature for 16 hours and the white crystals were subsequently filtered off. 780 mg (73%) of (S)-2-(8-methoxy-1H-benz[g]indol-1-yl)-1-methyl-ethylamine fumarate (1:0.5) with m.p. 208° were obtained.

EXAMPLE 8 a) A solution of 9.1 g of 6-ethyl-3,3-dimethyl-1-indanone, 9.98 ml of 3-buten-2-ol and 250 mg of p-toluenesulfonic acid in 100 ml of 2,2-dimethoxypropane was boiled under reflux for 88 hours on a water separator filled with molecular sieve (0.4 nm, 2 mm pearl shaped). The reaction mixture was subsequently concentrated in a vacuum and purified by column chromatography on silica gel (hexane/diethyl ether 6:1). In addition to 2.0 g of educt, there were obtained 8.2 g (70%) of (RS)-2-(2-buten-1-yl)-6-ethyl-3,3-dimethyl-1-indanone as a yellow oil.

b) An ozone stream (3 g ozone/hour) was conducted for 40 minutes while stirring through a solution, cooled to −70°, of 8.2 g of (RS)-2-(2-buten-1-yl)-6-ethyl-3,3-dimethyl-1-indanone in 120 ml of anhydrous dichloromethane and 30 ml of anhydrous methanol. Subsequently, the mixture was flushed with oxygen for 5 minutes and with argon for 10 minutes. After the addition of 3.72 ml of dimethyl sulfide, the mixture was stirred at room temperature for 16 hours.

The reaction mixture was evaporated in a vacuum. The residue was treated with 100 ml of dichoromethane and, after the addition of 15 ml of water and 15 ml of trifluoroacetic acid, stirred at room temperature for 2 hours. The mixture was subsequently poured into 100 ml of water and neutralized by the spatula-wise addition of sodium hydrogen carbonate while stirring. An additional 50 ml of water were added. The phases were separated and the aqueous phase was extracted twice with 100 ml of dichloromethane each time. The combined organic phases were dried over magnesium sulfate and concentrated in a vacuum. 7.55 g (97%) of (RS)-2-(2-oxoethyl)-6-ethyl-3,3-dimethyl1-indanone were obtained as a light yellow oil.

c) A solution of 2.3 g of (RS)-2-(2-oxoethyl)-6-ethyl-3,3-dimethyl-1-indanone and 80 mg of p-toluenesulfonic acid in 90 ml of anhydrous toluene was heated on a water separator. A solution of 3.0 g of (R)-1-amino-2-propanol in 40 ml of anhydrous toluene was added dropwise to the boiling solution over a period of 5 minutes. Subsequently, the mixture was boiled for an additional 45 minutes, during which the solvent was reduced to a volume of 20 ml. The cooled reaction mixture was purified by column chromatography on silica gel (diethyl ether/hexane 3:2). 2.45 g (91%) of (R)-1-(7-ethyl-4,4-dimethyl-1,4-dihydro-indeno[1,2-b]pyrrol-1-yl)-propan-2-ol were obtained as a red oil.

d) 1.39 ml of methanesulfonyl chloride were added dropwise while stirring to a solution, cooled to 0°, of 2.4 g of (R)-1-(7-ethyl-4,4-dimethyl-1,4-dihydro-indeno[1,2-b]pyrrol-1-yl)-propan-2-ol and 4.97 ml of triethylamine in 50 ml of dichloromethane and the mixture was stirred at this temperature for an additional 1.5 hours. The reaction mixture was subsequently diluted with 100 ml of dichloromethane, washed twice with 70 ml of saturated sodium hydrogen carbonate solution each time and the combined aqueous phases were extracted once with 70 ml of dichloromethane. The combined organic phases were washed with 90 ml of saturated sodium chloride solution, dried over magnesium sulfate and evaporated in a vacuum. The green oil obtained was dissolved in 50 ml of anhydrous dimethylformamide, treated with 1.16 g of sodium azide and the reaction mixture was heated to 60° for 17 hours while stirring. After cooling, the solution was poured into 70 ml of water and extracted three times with 100 ml of ethyl acetate each time. The combined organic phases were washed once with 70 ml of water and once with 70 ml of saturated sodium chloride solution, dried over magnesium sulfate and the solution was concentrated in a vacuum. The brown oil obtained was purified by column chromatography on silica gel (hexane/diethyl ether 4:1). 1.44 g (55%) of (S)-1-(2-azido-propyl)-7-ethyl-4,4-dimethyl-1,4-dihydro-indeno[1,2-b]pyrrole were obtained as a red oil.

e) 1.44 g of (S)-1-(2-azido-propyl)-7-ethyl-4,4-dimethyl-1,4-dihydro-indeno[1,2-b]pyrrole dissolved in 50 ml of anhydrous ethanol were hydrogenated on 140 mg of platinum oxide for 1.5 hours. The catalyst was subsequently filtered off, rinsed with ethanol and the solvent was drawn off in a vacuum. The colorless oil obtained was dissolved in 120 ml of anhydrous diethyl ether, filtered and treated while stirring with a solution of 568 mg of fumaric acid in 15 ml of methanol. The mixture was stirred at room temperature for 15 hours and the white crystals were subsequently filtered off. 1.04 g (55%) of (S)-2-(7-ethyl-4,4-dimethyl-1,4-dihydro-indeno[1,2-b]pyrrol-1-yl)-1-methyl-ethylamine fumarate (1:1) with m.p. 178° were obtained.

EXAMPLE 9 a) A solution of 10.0 g of 6-fluoro-3,3-dimethyl-1-indanone, 11.1 ml of 3-buten-2-ol and 200 mg of p-toluenesulfonic acid in 200 ml of 2,2-dimethoxypropane was boiled under reflux for 96 hours on a water separator filled with molecular sieve (0.4 nm, 2 mm pearl shaped). The reaction mixture was subsequently concentrated in a vacuum and purified by column chromatography on silica gel (hexane/ethyl acetate 8:1). In addition to 11.9 g of educt, there were obtained 3.38 g (26%) of (RS)-2-(2-buten-1-yl)-6-fluoro-3,3-dimethyl-1-indanone as a yellow oil.

b) An ozone stream (1.5 g ozone/hour) was conducted for 30 minutes while stirring through a solution, cooled to −70°, of 3.38 g of (RS)-2-(2-buten-1-yl)-6-fluoro-3,3-dimethyl-1-indanone in 75 ml of anhydrous dichloromethane and 15 ml of anhydrous methanol. Subsequently, the mixture was flushed with oxygen for 5 minutes and with argon for 10 minutes. After the addition of 1.6 ml of dimethyl sulfide, the mixture was stirred at room temperature for 17 hours. The reaction mixture was evaporated in a vacuum. The residue was treated with 40 ml of dichoromethane and, after the addition of 5 ml of water and 5 ml of trifluoroacetic acid, stirred at room temperature for 2 hours. The mixture was subsequently poured into 90 ml of water and neutralized by the spatula-wise addition of sodium hydrogen carbonate while stirring. An additional 50 ml of water were added, the phases were separated and the aqueous phase was extracted twice with 100 ml of dichloromethane each time. The combined organic phases were dried over magnesium sulfate and concentrated in a vacuum. 3.04 g (95%) of (RS)-2-(2-oxoethyl)-6-fluoro-3,3-dimethyl-1-indanone were obtained as a light yellow oil.

c) A solution of 3.04 g of (RS)-2-(2-oxoethyl)-6-fluoro-3,3-dimethyl-1-indanone and 110 mg of p-toluenesulfonic acid in 100 ml of anhydrous toluene was heated on a water separator. A solution of 4.14 g of (R)-1-amino-2-propanol in 40 ml of anhydrous toluene was added dropwise to the boiling solution over a period of 5 minutes. Subsequently, the mixture was boiled for an additional 45 minutes, during which the solvent was reduced to a volume of 20 ml. The cooled reaction mixture was purified by column chromatography on silica gel (ethyl acetate/toluene 1:1). 2.0 g (56%) of (R)-1-(7-fluoro-4,4-dimethyl-1,4-dihydro-indeno[1,2-b]pyrrol-1-yl)-propan-2-ol were obtained as a brown oil.

d) 1.27 ml of methanesulfonyl chloride were added dropwise while stirring to a solution, cooled to 0°, of 2.0 g of (R)-1-(7-fluoro-4,4-dimethyl-1,4-dihydro-indeno[1,2-b]pyrrol-1-yl)-propan-2-ol and 4.52 ml of triethylamine in 60 ml of dichloromethane and the mixture was stirred at this temperature for an additional 1.5 hours. The reaction mixture was subsequently diluted with 100 ml of dichloromethane, washed twice with 60 ml of saturated sodium hydrogen carbonate solution each time and the combined aqueous phases were extracted once with 60 ml of dichloromethane. The combined organic phases were washed with 70 ml of saturated sodium chloride solution, dried over magnesium sulfate and evaporated in a vacuum. The brown oil obtained was dissolved in 50 ml of anhydrous dimethylformamide, treated with 1.07 g of sodium azide and the reaction mixture was heated to 60° for 16 hours while stirring. After cooling, the solution was poured into 80 ml of water and extracted three times with 70 ml of ethyl acetate each time. The combined organic phases were washed once with 70 ml of water and once with 70 ml of saturated sodium chloride solution, dried over magnesium sulfate and the solution was concentrated in a vacuum. The brown oil obtained was purified by column chromatography on silica gel (toluene). 1.22 g (54%) of (S)-1-(2-azido-propyl)-7-fluoro-4,4-dimethyl-1,4-dihydro-indeno[1,2-b]pyrrole were obtained as a yellow oil.

e) 1.22 g of (S)-1-(2-azido-propyl)-7-fluoro-4,4-dimethyl-1,4-dihydro-indeno[1,2-b]pyrrole dissolved in 100 ml of anhydrous ethanol were hydrogenated on 120 mg of platinum oxide for 2 hours. The catalyst was subsequently filtered off, rinsed with ethanol and the solvent was drawn off in a vacuum. The colorless oil obtained was dissolved in 150 ml of anhydrous diethyl ether, filtered and treated while stirring with a solution of 498 mg of fumaric acid in 20 ml of methanol. The mixture was stirred at room temperature for 15 hours and the white crystals were subsequently filtered off. 1.12 g (70%) of (S)-2-(7-fluoro-4,4-dimethyl-1,4-dihydro-indeno[1,2-b]pyrrol-1-yl)-1-methyl-ethylamine fumarate (1:1) with m.p. 211° were obtained.

EXAMPLE 10 a) A solution of 14.2 g of 6-methyl-1-indanone, 20.1 ml of 3-buten-2-ol and 140 mg of p-toluenesulfonic acid in 140 ml of 2,2-dimethoxypropane was boiled under reflux for 69 hours on a water separator filled with molecular sieve (0.4 nm, 2 mm pearl shaped). The reaction mixture was subsequently concentrated in a vacuum and purified by column chromatography on silica gel (hexane/diethyl ether 5:1). 16.3 g (83%) of (RS)-2-(2-buten-1-yl)-6-methyl-1-indanone were obtained as a yellow oil.

b) An ozone stream (3 g ozone/hour) was conducted for 80 minutes while stirring through a solution, cooled to −70°, of 16.3 g of (RS)-2-(2-buten-1-yl)-6-methyl-1-indanone in 300 ml of anhydrous dichloromethane and 60 ml of anhydrous methanol. Subsequently, the mixture was flushed with oxygen for 5 minutes and with argon for 10 minutes. After the addition of 8.95 ml of dimethyl sulfide, the mixture was stirred at room temperature for 15 hours. The reaction mixture was evaporated in a vacuum, the residue was treated with 300 ml of dichoromethane and, after the addition of 40 ml of water and 40 ml of trifluoroacetic acid, stirred at room temperature for 3 hours. The mixture was subsequently poured into 200 ml of water and neutralized by the spatula-wise addition of sodium hydrogen carbonate while stirring. An additional 100 ml of water were added. The phases were separated and the aqueous phase was extracted twice with 200 ml of dichloromethane each time. The combined organic phases were dried over magnesium sulfate and concentrated in a vacuum. The crude product obtained was recrystallized from diethyl ether/hexane. 12.7 g (82%) of (RS)-2-(2-oxoethyl)-6-methyl-1-indanone were obtained as a light yellow solid with m.p. 53°–54°.

c) A solution of 2.82 g of (RS)-2-(2-oxoethyl)-6-methyl-1-indanone and 100 mg of p-toluenesulfonic acid in 100 ml of anhydrous toluene was heated on a water separator. A solution of 4.51 g of (R)-1-amino-2-propanol in 20 ml of anhydrous toluene was added dropwise to the boiling solution over a period of 5 minutes. Subsequently, the mixture was boiled for an additional 45 minutes, during which the solvent was reduced to a volume of 20 ml. The cooled reaction mixture was purified by column chromatography on silica gel (ethyl acetate/toluene 1:1). 2.7 g (79%) of (R)-1-(7-methyl-1,4-dihydro-indeno[1,2-b]pyrrol-1-yl)-propan-2-ol were obtained as a brown-green oil.

d) 1.8 ml of methanesulfonyl chloride were added dropwise while stirring to a solution, cooled to 0°, of 2.7 g of (R)-1-(7-methyl-1,4-dihydro-indeno[1,2-b]pyrrol-1-yl)-propan-2-ol and 6.7 ml of triethyl-amine in 75 ml of dichloromethane and the mixture was stirred at this temperature for an additional 1.5 hours. The reaction mixture was subsequently diluted with 200 ml of dichloromethane, washed twice with 90 ml of saturated sodium hydrogen carbonate solution each time and the combined aqueous phases were extracted once with 90 ml of dichloromethane. The combined organic phases were washed with 100 ml of saturated sodium chloride solution, dried over magnesium sulfate and evaporated in a vacuum. The brown oil obtained was dissolved in 70 ml of anhydrous dimethylformamide, treated with 1.55 g of sodium azide and the reaction mixture was heated to 60° for 15 hours while stirring. After cooling, the solution was poured into 150 ml of water and extracted twice with 150 ml of ethyl acetate each time. The combined organic phases were washed once with 120 ml of water and once with 120 ml of saturated sodium chloride solution, dried over magnesium sulfate and the solution was concentrated in a vacuum. The brown oil obtained was purified by column chromatography on silica gel (toluene). 1.5 g (50%) of (S)-1-(2-azido-propyl)-7-methyl-1,4-dihydro-indeno[1,2-b]pyrrole were obtained as a light yellow oil.

e) 1.5 g of (S)-1-(2-azido-propyl)-7-methyl-1,4-dihydro-indeno[1,2-b]pyrrole dissolved in 50 ml of anhydrous ethanol were hydrogenated on 150 mg of platinum oxide for 4 hours. The catalyst was subsequently filtered off, rinsed with ethanol and the solvent was drawn off in a vacuum. The colorless oil obtained was dissolved in 150 ml of anhydrous diethyl ether, filtered and treated white stirring with a solution of 345 mg of fumaric acid in 25 ml of methanol. The mixture was stirred at room temperature for 17 hours and the white crystals were subsequently filtered off. 1.11 g (65%) of (S)-2-(7-methyl-1,4-dihydro-indeno[1,2-b]pyrrol-1-yl)-1-methyl-ethylamine fumarate (1:0.5) with m.p. 194° were obtained.

EXAMPLE 11 a) A solution of 10.0 g of 6-bromo-1-indanone, 9.79 ml of 3-buten-2-ol and 100 mg of p-toluenesulfonic acid in 100 ml of 2,2-dimethoxypropane was boiled under reflux for 71 hours on a water separator filled with molecular sieve (0.4 nm, 2 mm pearl shaped). The reaction mixture was subsequently concentrated in a vacuum and purified by column chromatography on silica gel (hexane/diethyl ether 1:1). In addition to 3.07 g of educt, there were obtained 9.86 g (78%) of (RS)-2-(2-buten-1-yl)-6-bromo-1-indanone as a yellow oil.

b) An ozone stream (2 g ozone/hour) was conducted for 60 minutes while stirring through a solution, cooled to −70°, of 9.86 g of (RS)-2-(2-buten-1-yl)-6-bromo-1-indanone in 150 ml of anhydrous dichloro-methane and 30 ml of anhydrous methanol. Subsequently, the mixture was flushed with oxygen for 5 minutes and with argon for 10 minutes. After the addition of 4.09 ml of dimethyl sulfide, the mixture was stirred at room temperature for 15 hours. The reaction mixture was evaporated in a vacuum. The residue was treated with 1 50 ml of dichoromethane and, after the addition of 20 ml of water and 20 ml of trifluoroacetic acid, stirred at room temperature for 2 hours. The mixture was subsequently poured into 100 ml of water and neutralized by the spatula-wise addition of sodium hydrogen carbonate while stirring. An additional 50 ml of water were added. The phases were separated and the aqueous phase was extracted twice with 100 ml of dichloromethane each time. The combined organic phases were dried over magnesium sulfate and concentrated in a vacuum. The crude product obtained was recrystallized from ethyl acetate/hexane. 7.5 g (80%) of (RS)-2-(2-oxoethyl)-6-bromo-1-indanone were obtained as a light yellow solid with m.p. 84°.

c) A solution of 2.0 g of (RS)-2-(2-oxoethyl)-6-bromo-1-indanone and 80 mg of p-toluenesulfonic acid in 90 ml of anhydrous toluene was heated on a water separator. A solution of 2.37 g of (R)-1-amino-2-propanol in 10 ml of anhydrous toluene was added dropwise to the boiling solution over a period of 5 minutes. Subsequently, the mixture was boiled for an additional 45 minutes, during which the solvent was reduced to a volume of 20 ml. The cooled reaction mixture was purified by column chromatography on silica gel (diethyl ether/hexane 4:1). 1.19 g (52%) of (R)-1-(7-bromo-1,4-dihydro-indeno[1,2-b]pyrrol-1-yl)-propan-2-ol were obtained as a brown oil.

d) 0.63 ml of methanesulfonyl chloride was added dropwise while stirring to a solution, cooled to 0°, of 1.19 g of (R)-1-(7-bromo-1,4-dihydro-indeno[1,2-b]pyrrol-1-yl)-propan-2-ol and 2.27 ml of triethylamine in 40 ml of dichloromethane and the mixture was stirred at this temperature for an additional 1.5 hours. The reaction mixture was subsequently diluted with 100 ml of dichloromethane, washed twice with 70 ml of saturated sodium hydrogen carbonate solution each time and the combined aqueous phases were extracted once with 70 ml of dichloromethane. The combined organic phases were washed with 100 ml of saturated sodium chloride solution, dried over magnesium sulfate and evaporated in a vacuum. The green oil obtained was dissolved in 40 ml of anhydrous dimethylformamide, treated with 0.53 g of sodium azide and the reaction mixture was heated to 60° for 15 hours while stirring. After cooling, the solution was poured into 100 ml of water and extracted twice with 100 ml of ethyl acetate each time. The combined organic phases were washed once with 100 ml of water and once with 100 ml of saturated sodium chloride solution, dried over magnesium sulfate and the solution was concentrated in a vacuum. The brown oil obtained was purified by column chromatography on silica gel (toluene). 0.95 g (74%) of (S)-1-(2-azido-propyl)-7-bromo-1,4-dihydro-indeno[1,2-b]pyrrole were obtained as a colorless oil.

e) 0.95 g of (S)-1-(2-azido-propyl)-7-bromo-1,4-dihydro-indeno[1,2-b]pyrrole dissolved in 40 ml of anhydrous ethanol were hydrogenated on 95 mg of platinum oxide for 4 hours. The catalyst was subsequently filtered off, rinsed with ethanol and the solvent was drawn off in a vacuum. The product mixture was separated on silica gel (methanol/dichloromethane 5:95). The colorless oil obtained (507 mg) was dissolved in 50 ml of anhydrous diethyl ether, filtered and treated while stirring with a solution of 101 mg of fumaric acid in 10 ml of methanol. The mixture was stirred at room temperature for 17 hours and the white crystals were subsequently filtered off. 503 mg (50%) of (S)-2-(7-bromo-1,4-dihydro-indeno[1,2-b]pyrrol-1-yl)-1-methyl-ethylamine fumarate (1:0.5) with m.p. 197° were obtained.

EXAMPLE 12 a) A solution of 22.0 g of 6-methoxy-3,3-diethyl-1-indanone, 20.8 ml of 3-buten-2-ol and 220 mg of p-toluenesulfonic acid in 220 ml of 2,2-dimethoxypropane was boiled under reflux for 87 hours on a water separator filled with molecular sieve (0.4 nm, 2 mm pearl shaped). The reaction mixture was subsequently concentrated in a vacuum and purified by column chromatography on silica gel (hexane/ethyl acetate 6:1). In addition to 15.7 g of educt, there were obtained 4.1 g (15%) of (RS)-2-(2-buten-1-yl)-6-methoxy-3,3-diethyl-1-indanone as a yellow oil.

b) An ozone stream (2 g ozone/hour) was conducted for 25 minutes while stirring through a solution, cooled to −70°, of 4.1 g of (RS)-2-(2-buten-1-yl)-6-methoxy-3,3-diethyl-1-indanone in 60 ml of anhydrous dichloromethane and 15 ml of anhydrous methanol. Subsequently, the mixture was flushed with oxygen for 5 minutes and with argon for 10 minutes. After the addition of 1.66 ml of dimethyl sulfide, the mixture was stirred at room temperature for 22 hours. The reaction mixture was evaporated in a vacuum. The residue was treated with 50 ml of dichoromethane and, after the addition of 8 ml of water and 8 ml of trifluoroacetic acid, stirred at room temperature for 2.5 hours. The mixture was subsequently poured into 70 ml of water and neutralized by the spatula-wise addition of sodium hydrogen carbonate while stirring. An additional 50 ml of water were added. The phases were separated and the aqueous phase was extracted twice with 100 ml of dichloromethane each time. The combined organic phases were dried over magnesium sulfate and concentrated in a vacuum. 3.9 g (99%) of (RS)-2-(2-oxoethyl)-6-methoxy-3,3-diethyl-1-indanone were obtained as a light yellow oil.

c) A solution of 3.9 g of (RS)-2-(2-oxoethyl)-6-methoxy-3,3-diethyl-1-indanone and 120 mg of p-toluenesulfonic acid in 100 ml of anhydrous toluene was heated on a water separator. A solution of 4.5 g of (R)-1-amino-2-propanol in 30 ml of anhydrous toluene was added dropwise to the boiling solution over a period of 5 minutes. Subsequently, the mixture was boiled for an additional 45 minutes, during which the solvent was reduced to a volume of 20 ml. The cooled reaction mixture was purified by column chromatography on silica gel (ethyl acetate/hexane 1:1). 2.73 g (61%) of (R)-1-(7-methoxy-4,4-diethyl-1,4-dihydro-indeno[1,2-b]pyrrol-1-yl)-propan-2-ol were obtained as a red-brown oil.

d) 1.42 ml of methanesulfonyl chloride were added dropwise while stirring to a solution, cooled to 0°, of 2.73 g of (R)-1-(7-methoxy-4,4-diethyl-1,4-dihydro-indeno[1,2-b]pyrrol-1-yl)-propan-2-ol and 5.08 ml of triethylamine in 70 ml of dichloromethane and the mixture was stirred at this temperature for an additional 1.5 hours. The reaction mixture was subsequently diluted with 100 ml of dichloromethane, washed twice with 70 ml of saturated sodium hydrogen carbonate solution each time and the combined aqueous phases were extracted once with 70 ml of dichloromethane. The combined organic phases were washed with 70 ml of saturated sodium chloride solution, dried over magnesium sulfate and evaporated in a vacuum. The brown oil obtained was dissolved in 50 ml of anhydrous dimethylformamide, treated with 1.18 g of sodium azide and the reaction mixture was heated to 60° for 15 hours while stirring. After cooling, the solution was poured into 70 ml of water and extracted three times with 80 ml of ethyl acetate each time. The combined organic phases were washed once with 70 ml of water and once with 80 ml of saturated sodium chloride solution, dried over magnesium sulfate and the solution was concentrated in a vacuum. The brown oil obtained was purified by column chromatography on silica gel (hexane/ethyl acetate 4:1). 2.33 g (79%) of (S)-1-(2-azido-propyl)-7-methoxy-4,4-diethyl-1,4-dihydro-indeno[1,2-b]pyrrole were obtained as a yellow oil.

e) 2.25 g of (S)-1-(2-azido-propyl)-7-methoxy-4,4-diethyl-1,4-dihydro-indeno[1,2-b]pyrrole dissolved in 100 ml of anhydrous ethanol were hydrogenated on 225 mg of platinum oxide for 2 hours. The catalyst was subsequently filtered off, rinsed with ethanol and the solvent was drawn off in a vacuum. The colorless oil obtained was dissolved in 100 ml of anhydrous diethyl ether, filtered and treated while stirring with a solution of 406 mg of fumaric acid in 10 ml of methanol. The mixture was stirred at room temperature for 17 hours and the white crystals were subsequently filtered off. 1.93 g (78%) of (S)-2-(7-methoxy-4,4-diethyl-1,4-dihydro-indeno[1,2-b]pyrrol-1-yl)-1-methyl-ethylamine fumarate (1:0.5) with m.p. 189° were obtained.

EXAMPLE 13 a) A solution of 20.0 g of 5-fluoro-1-indanone, 27.5 ml of 3-buten-2-ol and 200 mg of p-toluenesulfonic acid in 200 ml of 2,2-dimethoxy-propane was boiled under reflux for 63 hours on a water separator filled with molecular sieve (0.4 nm, 2 mm pearl shaped). The reaction mixture was subsequently concentrated in a vacuum and purified by column chromatography on silica gel (hexane/diethyl ether 4:1). 18.6 g (68%) of (RS)-2-(2-buten-1-yl)-5-fluoro-1-indanone were obtained as a yellow oil.

b) An ozone stream (3.5 g ozone/hour) was conducted for 85 minutes while stirring through a solution, cooled to −70°, of 18.5 g of (RS)-2-(2-buten-1-yl)-5-fluoro-1-indanone in 300 ml of anhydrous dichloromethane and 50 ml of anhydrous methanol. Subsequently, the mixture was flushed with oxygen for 5 minutes and with argon for 10 minutes. After the addition of 9.9 ml of dimethyl sulfide, the mixture was stirred at room temperature for 17 hours. The reaction mixture was evaporated in a vacuum. The residue was treated with 220 ml of dichloromethane and, after the addition of 40 ml of water and 40 ml of trifluoroacetic acid, stirred at room temperature for 4.5 hours. The mixture was subsequently poured into 170 ml of water and neutralized by the spatula-wise addition of sodium hydrogen carbonate while stirring. An additional 110 ml of water were added, the phases were separated and the aqueous phase was extracted twice with 170 ml of dichloromethane each time. The combined organic phases were dried over magnesium sulfate and concentrated in a vacuum. There was obtained a yellow oil which was crystallized from diethyl ether/hexane 13.6 g (78%) of (RS)-2-(2-oxoethyl)-5-fluoro-1-indanone were obtained as a light yellow solid with m.p. 56°.

c) A solution of 2.88 g of (RS)-2-(2-oxoethyl)-5-fluoro-1-indanone and 100 mg of p-toluenesulfonic acid in 90 ml of anhydrous toluene was heated on a water separator. A solution of 4.51 g of (R)-1-amino-2-propanol in 20 ml of anhydrous toluene was added dropwise to the boiling solution over a period of 5 minutes. Subsequently, the mixture was boiled for an additional 45 minutes, during which the solvent was reduced to a volume of 20 ml. The cooled reaction mixture was purified by column chromatography on silica gel (ethyl acetate/toluene 1:1). 2.75 g (79%) of (R)-1-(6-fluoro-1,4-dihydro-indeno[1,2-b]pyrrol-1-yl)-propan-2-ol were obtained as a brown oil.

d) 1.8 ml of methanesulfonyl chloride were added dropwise while stirring to a solution, cooled to 0°, of 2.75 g of (R)-1-(6-fluoro-1,4-dihydro-indeno[1,2-b]pyrrol-1-yl)-propan-2-ol and 6.7 ml of triethyl-amine in 70 ml of dichloromethane and the mixture was stirred at this temperature for an additional 1.5 hours. The reaction mixture was subsequently diluted with 100 ml of dichloromethane, washed twice with 90 ml of saturated sodium hydrogen carbonate solution each time and the combined aqueous phases were extracted once with 90 ml of dichloromethane. The combined organic phases were washed with 100 ml of saturated sodium chloride solution, dried over magnesium sulfate and evaporated in a vacuum. The brown oil obtained was dissolved in 60 ml of anhydrous dimethylformamide, treated with 1.55 g of sodium azide and the reaction mixture was heated to 60° for 17 hours while stirring. After cooling the solution was poured into 80 ml of water and extracted three times with 100 ml of ethyl acetate each time. The combined organic phases were washed once with 70 ml of water and once with 70 ml of saturated sodium chloride solution, dried over magnesium sulfate and the solution was concentrated in a vacuum. The brown oil obtained was purified by column chromatography on silica gel (toluene). 1.23 g (40%) of (S)-1-(2-azido-propyl)-6-fluoro-1,4-dihydro-indeno[1,2-b]pyrrole were obtained as a light yellow oil.

e) 1.23 g of (S)-1-(2-azido-propyl)-6-fluoro-1,4-dihydro-indeno[1,2-b]pyrrole dissolved in 60 ml of anhydrous ethanol were hydrogenated on 125 mg of platinum oxide for 6 hours. The catalyst was subsequently filtered off, rinsed with ethanol and the solvent was drawn off in a vacuum. The colorless oil obtained was dissolved in 130 ml of anhydrous diethyl ether, filtered and treated while stirring with a solution of 279 mg of fumaric acid in 25 ml of methanol. The mixture was stirred at room temperature for 15 hours and the white crystals were subsequently filtered off. 1.0 g (72%) of (S)-2-(6-fluoro-1,4-dihydro-indeno[1,2-b]pyrrol-1-yl)-1-methyl-ethylamine fumarate (1:0.5) with m.p. 200° were obtained.

EXAMPLE 14 a) A solution of 13.2 g of 6-phenyl-1-indanone, 11 ml of 3-buten-2-ol and 110 mg of p-toluenesulfonic acid in 110ml of 2,2-dimethoxy-propane was boiled under reflux for 48 hours on a water separator filled with molecular sieve (0.4 nm, 2 mm pearl shaped). The reaction mixture was subsequently concentrated in a vacuum and purified by column chromatography on silica gel (hexane/diethyl ether 5:1). 12.0 g (72%) of (RS)-2-(2-buten-1-yl)-6-phenyl-1-indanone was obtained as a light yellow solid which was used without further purification in the next reaction.

b) An ozone stream (3 g ozone/hour) was conducted for 75 minutes while stirring through a solution, cooled to −70°, of 12.0 g of (RS)-2-(2-buten-1-yl)-6-phenyl-1-indanone in 180 ml of anhydrous dichloromethane and 40 ml of anhydrous methanol. Subsequently, the mixture was flushed with oxygen for 5 minutes and with argon for 10 minutes. After the addition of 5.04 ml of dimethyl sulfide, the mixture was stirred at room temperature for 15 hours. The reaction mixture was evaporated in a vacuum. The residue was treated with 120 ml of dichoromethane and, after the addition of 30 ml of water and 30 ml of trifluoroacetic acid, stirred at room temperature for 2 hours. The mixture was subsequently poured into 150 ml of water and neutralized by the spatula-wise addition of sodium hydrogen carbonate while stirring. An additional 50 ml of water were added. The phases were separated and the aqueous phase was extracted twice with 200 ml of dichloromethane each time. The combined organic phases were dried over magnesium sulfate and concentrated in a vacuum. 1.2 g (97%) of (RS)-2-(2-oxoethyl)-6-phenyl-1-indanone were obtained as a light yellow oil.

c) A solution of 2.5 g of (RS)-2-(2-oxoethyl)-6-phenyl-1-indanone and 80 mg of p-toluenesulfonic acid in 70 ml of anhydrous toluene was heated on a water separator. A solution of 3.0 g of (R)-1-amino-2-propanol in 20 ml of anhydrous toluene was added dropwise to the boiling solution over a period of 5 minutes. Subsequently, the mixture was boiled for an additional 45 minutes, during which the solvent was reduced to a volume of 20 ml. The cooled reaction mixture was purified by column chromatography on silica gel (diethyl ether/hexane 7:3). 1.5 g (52%) of (R)-1-(7-phenyl-1,4-dihydro-indeno[1,2-b]pyrrol-1-yl)-propan-2-ol were obtained as a brown oil.

d) 0.82 ml of methanesulfonyl chloride was added dropwise while stirring to a solution, cooled to 0°, of 1.5 g of (R)-1-(7-phenyl-1,4-dihydro-indeno[1,2-b]pyrrol-1-yl)-propan-2-ol and 3 ml of triethyl-amine in 50 ml of dichloromethane and the mixture was stirred at this temperature for an additional 1.5 hours. The reaction mixture was subsequently diluted with 150 ml of dichloromethane, washed twice with 70 ml of saturated sodium hydrogen carbonate solution each time and the combined aqueous phases were extracted once with 70 ml of dichloromethane. The combined organic phases were washed with 100 ml of saturated sodium chloride solution, dried over magnesium sulfate and evaporated in a vacuum. The green solid obtained was dissolved in 50 ml of anhydrous dimethylformamide, treated with 0.53 g of sodium azide and the reaction mixture was heated to 60° for 15 hours while stirring. After cooling, the solution was poured into 100 ml of water and extracted twice with 100 ml of ethyl acetate each time. The combined organic phases were washed once with 80 ml of water and once with 100 ml of saturated sodium chloride solution, dried over magnesium sulfate and the solution was concentrated in a vacuum. The brown oil obtained was purified by column chromatography on silica gel (toluene). 0.64 g (39%) of (S)-1-(2-azido-propyl)-7-phenyl-1,4-dihydro-indeno[1,2-b]pyrrole was obtained as a brown oil.

e) 0.64 g of (S)-1-(2-azido-propyl)-7-phenyl-1,4-dihydro-indeno[1,2-b]pyrrole dissolved in 30 ml of anhydrous ethanol were hydrogenated on 65 mg of platinum oxide for 2 hours. The catalyst was subsequently filtered off, rinsed with ethanol and the solvent was drawn off in a vacuum. The greenish solid obtained was dissolved in 80 ml of anhydrous diethyl ether, filtered and treated while stirring with a solution of 118 mg of fumaric acid in 20 ml of methanol. The mixture was stirred at room temperature for 15 hours and the beige crystals were subsequently filtered off. 0.37 g (53%) of (S)-2-(7-phenyl-1,4-dihydro-indeno[1,2-b]pyrrol-1-yl)-1-methyl-ethylamine fumarate (1:0.5) with m.p. 202°–204° was obtained.

EXAMPLE 15 a) A solution of 16 g of 6-hydroxy-1-indanone, 22.3 ml of 3-buten-2-ol and 160 mg of p-toluenesulfonic acid in 170 ml of 2,2-dimethoxy-propane was boiled under reflux for 38 hours on a water separator filled with molecular sieve (0.4 nm, 2 mm pearl shaped). The reaction mixture was subsequently concentrated in a vacuum and purified by column chromatography on silica gel (hexane/ethyl acetate 4:1). In addition to 7.5 g of educt, there were obtained 6.21 g (28%) of (RS)-2-(2-buten-1-yl)-6-hydroxy-1-indanone as a yellow oil.

b) A solution of 5.0 g of (RS)-2-(2-buten-1-yl)-6-hydroxy-1-indanone, 4.1 ml of ethyl bromide, 6.83 g of potassium carbonate and 10 ml of N,N-dimethyl-formamide in 70 ml of acetone was heated to 35° for 35 hours. After cooling, the solution was poured into 100 ml of water and extracted twice with 100 ml of ethyl acetate each time. The combined organic phases were washed once with 70 ml of water and once with 70 ml of saturated sodium chloride solution, dried over magnesium sulfate and the solution was concentrated in a vacuum. 5.6 g (98%) of (RS)-2-(2-buten-1-yl)-6-ethoxy-1-indanone were obtained as a red-brown oil which was used directly in the next reaction.

c) An ozone stream (3 g ozone/hour) was conducted for 90 minutes while stirring through a solution, cooled to −70°, of 5.6 g of (RS)-2-(2-buten-1-yl)-6-ethoxy-1-indanone in 150 ml of anhydrous dichloromethane and 30 ml of anhydrous methanol. Subsequently, the mixture was flushed with oxygen for 5 minutes and with argon for 10 minutes. After the addition of 2.72 ml of dimethyl sulfide, the mixture was stirred at room temperature for 15 hours. The reaction mixture was evaporated in a vacuum. The residue was treated with 170 ml of dichoromethane and, after the addition of 25 ml of water and 25 ml of trifluoroacetic acid, stirred at room temperature for 3 hours. The mixture was subsequently poured into 150 ml of water and neutralized by the spatula-wise addition of sodium hydrogen carbonate while stirring. An additional 50 ml of water were added. The phases were separated and the aqueous phase was extracted twice with 100 ml of dichloromethane each time. The combined organic phases were dried over magnesium sulfate and concentrated in a vacuum. 3.4 g (64%) of (RS)-2-(2-oxoethyl)-6-ethoxy-1-indanone were obtained as a red-brown oil.

d) A solution of 1.6 g of (RS)-2-(2-oxoethyl)-6-ethoxy-1-indanone and 70 mg of p-toluenesulfonic acid in 70 ml of anhydrous toluene was heated on a water separator. A solution of 2.2 g of (R)-1-amino-2-propanol in 20 ml of anhydrous toluene was added dropwise to the boiling solution over a period of 5 minutes. Subsequently, the mixture was boiled for an additional 45 minutes, during which the solvent was reduced to a volume of 20 ml. The cooled reaction mixture was purified by column chromatography on silica gel (ethyl acetate/hexane 4:1). 1.03 g (52%) of (R)-1-(7-ethoxy-1,4-dihydro-indeno[1,2-b]pyrrol-1-yl)-propan-2-ol were obtained as a brown oil.

e) 0.59 ml of methanesulfonyl chloride was added dropwise while stirring to a solution, cooled to 0°, of 1.03 g of (R)-1-(7-ethoxy-1,4-dihydro-indeno[1,2-b]pyrrol-1-yl)-propan-2-ol and 2.1 ml of triethylamine in 50 ml of dichloromethane and the mixture was stirred at this temperature for an additional 1.5 hours. The reaction mixture was subsequently diluted with 100 ml of dichloromethane, washed twice with 70 ml of saturated sodium hydrogen carbonate solution each time and the combined aqueous phases were extracted once with 70 ml of dichloromethane. The combined organic phases were washed with 100 ml of saturated sodium chloride solution, dried over magnesium sulfate and evaporated in a vacuum. The green oil obtained was dissolved in 30 ml of anhydrous dimethylformamide, treated with 0.6 g of sodium azide and the reaction mixture was heated to 60° for 20 hours while stirring. After cooling, the solution was poured into 100 ml of water and extracted three times with 100 ml of ethyl acetate each time. The combined organic phases were washed once with 70 ml of water and once with 70 ml of saturated sodium chloride solution, dried over magnesium sulfate and the solution was concentrated in a vacuum. The brown oil obtained was purified by column chromatography on silica gel (ethyl acetate/hexane 1:10). 948 mg (72%) of (S)-1-(2-azido-propyl)-7-ethoxy-1,4-dihydro-indeno[1,2-b]pyrrole were obtained as a light yellowish oil.

f) 0.94 g of (S)-1-(2-azido-propyl)-7-ethoxy-1,4-dihydro-indeno[1,2-b]pyrrole dissolved in 80 ml of anhydrous ethanol were hydrogenated on 94 mg of platinum oxide for 3 hours. The catalyst was subsequently filtered off, rinsed with ethanol and the solvent was drawn off in a vacuum. The colorless oil obtained was dissolved in 100 ml of anhydrous diethyl ether, filtered and treated while stirring with a solution of 198 mg of fumaric acid in 20 ml of methanol. The mixture was stirred at room temperature for 17 hours and the white crystals were subsequently filtered off. 581 mg (56%) of (S)-2-(7-ethoxy-1,4-dihydro-indeno[1,2-b]pyrrol-1-yl)-1-methyl-ethylamine fumarate (1:0.5) with m.p. 212°–214° were obtained.

EXAMPLE 16 a) A solution of 4.74 g of (RS)-2-(2-buten-1-yl)-6-hydroxy-1-indanone, 5.18 ml of isobutyl bromide and 5.98 g of potassium carbonate in 40 ml of N,N-dimethylformamide was heated to 60° for 48 hours. After cooling, the solution was poured into 100 ml of water and extracted twice with 70 ml of ethyl acetate each time. The combined organic phases were washed once with 70 ml of water and once with 70 ml of saturated sodium chloride solution, dried over magnesium sulfate and the solution was concentrated in a vacuum. 5.2 g (93%) of (RS)-2-(2-buten-1-yl)-6-isobutoxy-1-indanone were obtained as a red-brown oil which was used directly in the next reaction.

b) An ozone stream (2 g ozone/hour) was conducted for 90 minutes while stirring through a solution, cooled to −70°, of 5.1 g of (RS)-2-(2-buten-1-yl)-6-isobutoxy-1-indanone in 150 ml of anhydrous dichloromethane and 30 ml of anhydrous methanol. Subsequently, the mixture was flushed with oxygen for 5 minutes and with argon for 10 minutes. After the addition of 2.16 ml of dimethyl sulfide, the mixture was stirred at room temperature for 15 hours. The reaction mixture was evaporated in a vacuum, the residue was treated with 170 ml of dichoromethane and, after the addition of 25 ml of water and 25 ml of trifluoroacetic acid, stirred at room temperature for 3 hours. The mixture was subsequently poured into 150 ml of water and neutralized by the spatula-wise addition of sodium hydrogen carbonate while stirring. An additional 50 ml of water were added. The phases were separated and the aqueous phase was extracted twice with 100 ml of dichloromethane each time. The combined organic phases were dried over magnesium sulfate and concentrated in a vacuum. 2.3 g (48%) of (RS)-2-(2-oxoethyl)-6-isobutoxy-1-indanone were obtained as a red-brown oil.

c) A solution of 2.3 g of (RS)-2-(2-oxoethyl)-6-isobutoxy-1-indanone and 70 mg of p-toluenesulfonic acid in 70 ml of anhydrous toluene was heated on a water separator. A solution of 2.93 g of (RS)-1-amino-2-propanol in 20 ml of anhydrous toluene was added dropwise to the boiling solution over a period of 5 minutes. Subsequently, the mixture was boiled for an additional 45 minutes, during which the solvent was reduced to a volume of 20 ml. The cooled reaction mixture was purified by column chromatography on silica gel (ethyl acetate/hexane 1:4). 1.52 g (57%) of (RS)-1-(7-isobutoxy-1,4-dihydro-indeno[1,2-b]pyrrol-1-yl)-propan-2-ol were obtained as a red oil.

d) 0.81 ml of methanesulfonyl chloride was added dropwise while stirring to a solution, cooled to 0°, of 1.5 g of (RS)-1-(7-isobutoxy-1,4-dihydro-indeno[1,2-b]pyrrol-1-yl)-propan-2-ol and 2.93 ml of triethylamine in 50 ml of dichloromethane and the mixture was stirred at this temperature for an additional 1.5 hours. The reaction mixture was subsequently diluted with 100 ml of dichloromethane, washed twice with 70 ml of saturated sodium hydrogen carbonate solution each time and the combined aqueous phases were extracted once with 70 ml of dichloromethane. The combined organic phases were washed with 100 ml of saturated sodium chloride solution, dried over magnesium sulfate and evaporated in a vacuum. The green oil obtained was dissolved in 30 ml of anhydrous dimethylformamide, treated with 0.68 g of sodium azide and the reaction mixture was heated to 60° for 15 hours while stirring. After cooling, the solution was poured into 100 ml of water and extracted twice with 100 ml of ethyl acetate each time. The combined organic phases were washed once with 70 ml of water and once with 70 ml of saturated sodium chloride solution, dried over magnesium sulfate and the solution was concentrated in a vacuum. The brown oil obtained was purified by column chromatography on silica gel (ethyl acetata/hexane 1:4). 0.43 g (26%) of (RS)-1-(2-azido-propyl)-7-ethyl-4,4-dimethyl-1,4-dihydro-indeno[1,2-b]pyrrole was obtained as a light yellowish oil.

e) 0.43 g of (RS)-1-(2-azido-propyl)-7-isobutoxy-1,4-dihydro-indeno[1,2-b]pyrrole dissolved in 50 ml of anhydrous ethanol were hydrogenated on 50 mg of platinum oxide for 4 hours. The catalyst was subsequently filtered off, rinsed with ethanol and the solvent was drawn off in a vacuum. The colorless oil obtained was dissolved in 70 ml of anhydrous diethyl ether, filtered and treated while stirring with a solution of 80 mg of fumaric acid in 10 ml of methanol. The mixture was stirred at room temperature for 17 hours and the white crystals were subsequently filtered off. 0.25 mg (53%) of (RS)-2-(7-isobutoxy-1,4-dihydro-indeno[1,2-b]pyrrol-1-yl)-1-methyl-ethylamine fumarate (1:0.5) with m.p. 178° were obtained.

EXAMPLE 17 a) A solution of 11.8 g of 6-ethyl-1-indanone, 15.4 ml of 3-buten-2-ol and 110 mg of p-toluenesulfonic acid in 110 ml of 2,2-dimethoxy-propane was boiled under reflux for 46 hours on a water separator filled with molecular sieve (0.4 nm, 2 mm pearl shaped). The reaction mixture was subsequently concentrated in a vacuum and purified by column chromatography on silica gel (hexane/diethyl ether 5:1). 7.92 g (50%) of (RS)-2-(2-buten-1-yl)-6-ethyl-1-indanone were obtained as a yellow oil.

b) An ozone stream (3 g ozone/hour) was conducted for 40 minutes while stirring through a solution, cooled to −70°, of 7.92 g of (RS)-2-(2-buten-1-yl)-6-ethyl-1-indanone in 150 ml of anhydrous dichloromethane and 30 ml of anhydrous methanol. Subsequently, the mixture was flushed with oxygen for 5 minutes and with argon for 10 minutes. After the addition of 3.36 ml of dimethyl sulfide, the mixture was stirred at room temperature for 15 hours. The reaction mixture was evaporated in a vacuum. The residue was treated with 150 ml of dichoromethane and, after the addition of 30 ml of water and 30 ml of trifluoroacetic acid, stirred at room temperature for 3 hours. The mixture was subsequently poured into 150 ml of water and neutralized by the spatula-wise addition of sodium hydrogen carbonate while stirring. An additional 50 ml of water were added. The phases were separated and the aqueous phase was extracted twice with 100 ml of dichloromethane each time. The combined organic phases were dried over magnesium sulfate and concentrated in a vacuum. 6.94 g (93%) of (RS)-2-(2-oxoethyl)-6-ethyl-indanone were obtained as a yellow oil.

c) A solution of 2.02 g of (RS)-2-(2-oxoethyl)-6-ethyl-1-indanone and 80 mg of p-toluenesulfonic acid in 70 ml of anhydrous toluene was heated on a water separator. A solution of 3.0 g of (R)-1-amino-2-propanol in 20 ml of anhydrous toluene was added dropwise to the boiling solution over a period of 5 minutes. Subsequently, the mixture was boiled for an additional 45 minutes, during which the solvent was reduced to a volume of 20 ml. The cooled reaction mixture was purified by column chromatography on silica gel (ethyl acetate/toluene 1:1). 1.7 g (71%) of (R)-1-(7-ethyl-1,4-dihydro-indeno[1,2-b]pyrrol-1-yl)-propan-2-ol were obtained as a brown oil.

d) 1.1 ml of methanesulfonyl chloride were added dropwise while stirring to a solution, cooled to 0°, of 1.7 g of (R)-1-(7-ethyl-1,4-dihydro-indeno[1,2-b]pyrrol-1-yl)-propan-2-ol and 3.9 ml of triethylamine in 55 ml of dichloromethane and the mixture was stirred at this temperature for an additional 1.5 hours. The reaction mixture was subsequently diluted with 100 ml of dichloromethane, washed twice with 70 ml of saturated sodium hydrogen carbonate solution each time and the combined aqueous phases were extracted once with 70 ml of dichloromethane. The combined organic phases were washed with 100 ml of saturated sodium chloride solution, dried over magnesium sulfate and evaporated in a vacuum. The green oil obtained was dissolved in 50 ml of anhydrous dimethylformamide, treated with 0.84 g of sodium azide and the reaction mixture was heated to 60° for 16 hours while stirring. After cooling, the solution was poured into 120 ml of water and extracted twice with 120 ml of ethyl acetate each time. The combined organic phases were washed once with 100 ml of water and once with 100 ml of saturated sodium chloride solution, dried over magnesium sulfate and the solution was concentrated in a vacuum. The brown oil obtained was purified by column chromatography on silica gel (toluene). 0.74 g (40%) of (S)-1-(2-azido-propyl)-7-ethyl-1,4-dihydro-indeno [1,2-b]pyrrole was obtained as a yellow oil.

e) 0.74 g of (S)-1-(2-azido-propyl)-7-ethyl-1,4-dihydro-indeno[1,2-b]pyrrole dissolved in 30 ml of anhydrous ethanol were hydrogenated on 80 mg of platinum oxide for 15 hours. The catalyst was subsequently filtered off, rinsed with ethanol and the solvent was drawn off in a vacuum. The colorless oil obtained was dissolved in 50 ml of anhydrous diethyl ether, filtered and treated while stirring with a solution of 345 mg of fumaric acid in 10 ml of methanol. The mixture was stirred at room temperature for 17 hours and the white crystals were subsequently filtered off. 0.45 g (56%) of (S)-2-(7-ethyl-1,4-dihydro-indeno[1,2-b]pyrrol-1-yl)-1-methyl-ethylamine fumarate (1:0.5) with m.p. 189°–190° was obtained.

EXAMPLE 18 a) A solution of 8 g of 6-methoxycarbonyl-1-indanone, 8 ml of 3-buten-2-ol and 100 mg of p-toluenesulfonic acid in 80 ml of 2,2-dimethoxy-propane was boiled under reflux for 28 hours on a water separator filled with molecular sieve (0.4 nm, 2 mm pearl shaped). The reaction mixture was subsequently concentrated in a vacuum and purified by column chromatography on silica gel (hexane/ethyl acetate 3:1). In addition to 1.3 g of educt, there were obtained 8.5 g (83%) of (RS)-2-(2-buten-1-yl)-6-methoxycarbonyl-1-indanone as a yellow oil.

b) An ozone stream (3 g ozone/hour) was conducted for 45 minutes while stirring through a solution, cooled to –70°, of 10.5 g of (RS)-2-(2-buten-1-yl)-6-methoxycarbonyl-1-indanone in 150 ml of anhydrous dichloromethane. Subsequently, the mixture was flushed with oxygen for 5 minutes and with argon for 10 minutes. After the addition of 4.74 ml of dimethyl sulfide, the mixture was stirred at room temperature for 18 hours. The reaction mixture was evaporated in a vacuum and purified by column chromatography on silica get (diethyl ether). By recrystallization of the resulting solid, there were obtained 4.5 g (45%) of (RS)-2-(2-oxoethyl)-6-methoxycarbonyl-1-indanone as a light yellow solid with m.p. 92°.

c) A solution of 2.32 g of (RS)-2-(2-oxoethyl)-6-methoxycarbonyl-1-indanone and 80 mg of p-toluenesulfonic acid in 70 ml of anhydrous toluene was heated on a water separator. A solution of 3 g of (RS)-1-amino-2-propanol in 20 ml of anhydrous toluene was added dropwise to the boiling solution over a period of 5 minutes. Subsequently, the mixture was boiled for an additional 45 minutes, during which the solvent was reduced to a volume of 20 ml. The cooled reaction mixture was purified by column chromatography on silica gel (ethyl acetate/toluene 1:1). 2.2 g (81%) of (RS)-1-(7-methoxycarbonyl-1,4-dihydro-indeno[1,2-b]pyrrol-1-yl)-propan-2-ol were obtained as a brown oil.

d) 1.26 ml of methanesulfonyl chloride were added dropwise while stirring to a solution, cooled to 0°, of 2.2 g of (RS)-1-(7-methoxycarbonyl-1,4-dihydro-indeno[1,2-b] pyrrol-1-yl)-propan-2-ol and 4.55 ml of triethylamine in 60 ml of dichloromethane and the mixture was stirred at this temperature for an additional 1.5 hours. The reaction mixture was subsequently diluted with 100 ml of dichloromethane, washed twice with 70 ml of saturated sodium hydrogen carbonate solution each time and the combined aqueous phases were extracted once with 70 ml of dichloromethane. The combined organic phases were washed with 100 ml of saturated sodium chloride solution, dried over magnesium sulfate and evaporated in a vacuum. The brown oil obtained was dissolved in 50 ml of anhydrous dimethylformamide, treated with 1.05 g of sodium azide and the reaction mixture was heated to 60° for 15 hours while stirring. After cooling, the solution was poured into 100 ml of water and extracted twice with 100 ml of ethyl acetate each time. The combined organic phases were washed once with 70 ml of water and once with 70 ml of saturated sodium chloride solution, dried over magnesium sulfate and the solution was concentrated in a vacuum. The brown oil obtained was purified by column chromatography on silica gel (toluene). 950 mg (40%) of (RS)-1-(2-azido-propyl)-7-methoxycarbonyl-1,4-dihydro-indeno[1,2-b]pyrrole were obtained as a light brown oil.

e) 0.95 g of (RS)-1-(2-azido-propyl)-7-methoxycarbonyl-1,4-dihydro-indeno[1,2-b]pyrrole dissolved in 70 ml of anhydrous methanol were hydrogenated on 95 mg of platinum oxide for 4 hours. The catalyst was subsequently filtered off, rinsed with methanol and the solvent was drawn off in a vacuum. The colorless oil obtained was dissolved in 110 ml of anhydrous diethyl ether, filtered and treated while stirring with a solution of 186 mg of fumaric acid in 20 ml of methanol. The mixture was stirred at room temperature for 3 hours and the white crystals were subsequently filtered off. 770 mg (73%) of (RS)-2-(7-methoxycarbonyl-1,4-dihydro-indeno[1,2-b]pyrrol-1-yl)-1-methyl-ethylamine fumarate (1:0.5) with m.p. 199°–200° were obtained.

EXAMPLE 19 a) A 2M phenyllithium solution was added dropwise over 5 minutes to a solution, cooled to 0°, of 3.55 g of (RS)-1-(2-azido-propyl)-7-mesyloxycarbonyl-1,4-dihydro-indeno [1,2-b]pyrrole, 90 ml of anhydrous diethyl ether and 90 ml of anhydrous tetrahydrofuran. After 15 minutes at this temperature, an additional 5.87 ml of the phenyllithium solution were added dropwise and the mixture was stirred for an additional 5 minutes. Subsequently, the reaction mixture was treated with 50 ml of a saturated ammonium chloride solution and 25 ml of water. The mixture was extracted once with 50 ml of ethyl acetate and the aqueous phase was made slightly acidic with 1N hydrochloric acid and extracted three times with 100 ml of ethyl acetate each time. The combined organic phases were washed once with 100 ml of saturated sodium chloride solution, dried over magnesium sulfate and concentrated in a vacuum. 2.7 g (99%) of (RS)-1-(2-azido-propyl)-7-hydroxy-1,4-dihydro-indeno[1,2-b]pyrrole were obtained as a brown oil.

b) 0.7 ml of acetic anhydride was added while stirring to a solution of 1.05 g of (RS)-1-(2-azido-propyl)-7-hydroxy-1,4-dihydro-indeno[1,2-b]pyrrol and 0.6 ml of pyridine in 30 ml of dichloromethane and the mixture was stirred for an additional 16 hours. Subsequently, the reaction mixture was treated with 50 ml of dichloromethane and 40 ml of water. The organic phase was separated and this was washed once with 50 ml of saturated sodium chloride solution. After drying over magnesium sulfate, the solution was concentrated in a vacuum and the crude product was purified by column chromatography on silica gel (ethyl acetate/hexane 1:2). 0.9 g (85%) of (RS)-1-(2-azido-propyl)-7-acetoxy-1,4-dihydro-indeno[1,2-b]pyrrole was obtained as a light orange oil.

c) 0.84 g of (RS)-1-(2-azido-propyl)-7-acetoxy-1,4-dihydro-indeno[1,2-b]pyrrole dissolved in 100 ml of anhydrous ethanol was hydrogenated on 85 mg of platinum oxide for 4 hours. The catalyst was subsequently filtered off, rinsed with ethanol and the solvent was drawn off in a vacuum. The colorless oil obtained was dissolved in 100 ml of anhydrous diethyl ether, filtered and treated while stirring with a solution of 178 mg of fumaric acid in 20 ml of methanol. The mixture was stirred at room temperature for 4 hours and the white crystals were subsequently filtered off. 400 mg (43%) of (RS)-2-(7-acetoxy-1,4-dihydro-indeno[1,2-b]pyrrol-1-yl)-1-methyl-ethylamine fumarate (1:0.5) with m.p. 187°–188° were obtained.

EXAMPLE 20 a) A solution of 1.88 g of (RS)-2-(2-oxoethyl)-6-methyl-1-indanone and 80 mg of p-toluenesulfonic acid in 70 ml of anhydrous toluene was heated on a water separator. A solution of 3.0 g of (RS)-1-amino-2-propanol in 20 ml of anhydrous toluene was added dropwise to the boiling solution over a period of 5 minutes. Subsequently, the mixture was boiled for an additional 45 minutes, during which the solvent was reduced to a volume of 20 ml. The cooled reaction mixture was purified by column chromatography on silica gel (diethyl ether/hexane 7:3). 0.99 g (44%) of (RS)-1-(7-methyl-1,4-dihydro-indeno[1,2-b]pyrrol-1-yl)-propan-2-ol were obtained as a brown oil.

b) 0.67 ml of methanesulfonyl chloride were added dropwise while stirring to a solution, cooled to 0°, of 0.98 g of (RS)-1-(7-methyl-1,4-dihydro-indeno[1,2-b]pyrrol-1-yl)-propan-2-ol and 2.4 ml of triethylamine in 50 ml of dichloromethane and the mixture was stirred at this temperature for an additional 1.5 hours. The reaction mixture was subsequently diluted with 100 ml of dichloromethane, washed twice with 70 ml of saturated sodium hydrogen carbonate solution each time and the combined aqueous phases were extracted once with 70 ml of dichloromethane. The combined organic phases were washed with 100 ml of saturated sodium chloride solution, dried over magnesium sulfate and evaporated in a vacuum. The green oil obtained was dissolved in 40 ml of anhydrous dimethylformamide, treated with 0.56 g of sodium azide and the reaction mixture was heated to 60° for 16 hours while stirring. After cooling, the solution was poured into 100 ml of water and extracted twice with 100 ml of ethyl acetate each time. The combined organic phases were washed once with 70 ml of water and once with 70 ml of saturated sodium chloride solution, dried over magnesium sulfate and the solution was concentrated in a vacuum. The brown oil obtained was purified by column chromatography on silica gel (toluene). 737 mg (68%) of (RS)-1-(2-azido-propyl)-7-methyl-1,4-dihydro-indeno[1,2-b]pyrrole were obtained as a colorless oil.

c) 0.73 g of (RS)-1-(2-azido-propyl)-7-methyl-1,4-dihydro-indeno[1,2-b]pyrrole dissolved in 40 ml of anhydrous ethanol were hydrogenated on 75 mg of platinum oxide for 3 hours. The catalyst was subsequently filtered off, rinsed with ethanol and the solvent was drawn off in a vacuum. The colorless oil obtained was dissolved in 50 ml of anhydrous diethyl ether, filtered and treated while stirring with a solution of 168 mg of fumaric acid in 10 ml of methanol. The mixture was stirred at room temperature for 17 hours and the white crystals were subsequently filtered off. 596 mg (73%) of (RS)-2-(7-methyl-1,4-dihydro-indeno[1,2-b]pyrrol-1-yl)-1-methyl-ethylamine fumarate (1:0.5) with m.p. 194° were obtained.

EXAMPLE 21 a) A solution of 2.08 g of (RS)-2-(2-oxoethyl)-6-chloro-1-indanone and 80 mg of p-toluenesulfonic acid in 70 ml of anhydrous toluene was heated on a water separator. A solution of 3.0 g of (RS)-1-amino-2-propanol in 20 ml of anhydrous toluene was added dropwise to the boiling solution over a period of 5 minutes. Subsequently, the mixture was boiled for an additional 45 minutes, during which the solvent was reduced to a volume of 30 ml. The cooled reaction mixture was purified by column chromatography on silica gel (ethyl acetate/toluene 3:7). 1.52 g (61%) of (RS)-1-(7-chloro-1,4-dihydro-indeno[1,2-b]pyrrol-1-yl)-propan-2-ol were obtained as a brown oil which was used directly in the next reaction.

b) 0.95 ml of methanesulfonyl chloride was added dropwise while stirring to a solution, cooled to 0° C., of 1.52 g of (RS)-1-(7-chloro-1,4-dihydro-indeno[1,2-b]pyrrol-1-yl)-propan-2-ol and 3.4 ml of triethylamine in 40 ml of dichoromethane and the mixture was stirred at this temperature for an additional 1.5 hours. The reaction mixture was subsequently diluted with 280 ml of diethyl ether, washed twice with 70 ml of saturated sodium hydrogen carbonate solution each time and the combined aqueous phases were washed once with 70 ml of diethyl ether. The combined organic phases were washed with 70 ml of saturated sodium chloride solution, dried over magnesium sulfate and evaporated in a vacuum. The brown oil obtained was dissolved in 30 ml of anhydrous dimethylformamide, treated with 718 mg of sodium azide and the reaction mixture was heated to 60° for 17 hours while stirring. After cooling the solution was poured into 140 ml of water and extracted twice with 140 ml of diethyl ether each time and once with 140 ml of ethyl acetate. The combined organic phases were washed once with 140 ml of water and once with 140 ml of saturated sodium chloride solution, dried over magnesium sulfate and the solution was concentrated in a vacuum. The brown oil obtained was purified by column chromatography on silica gel (toluene). 1.0 g (60%) of (RS)-1-(2-azido-propyl)-7-chloro-1,4-dihydro-indeno[1,2-b]-pyrrole was obtained as an oil.

c) 1.0 g of (RS)-1-(2-azido-propyl)-7-chloro-1,4-dihydro-indeno[1,2-b]-pyrrole dissolved in 40 ml of anhydrous ethanol was hydrogenated on 100 mg of platinum oxide for 17 hours. The catalyst was subsequently filtered off, rinsed with ethanol and the solvent was drawn off in a vacuum. The colorless oil obtained was dissolved in 75 ml of anhydrous diethyl ether, filtered and treated while stirring with a solution of 195 mg of fumaric acid in 15 ml of methanol. The mixture was stirred at room temperature for 19 hours and the white crystals were subsequently filtered off. 945 mg (85%) of (RS)-2-(7-chloro-1,4-dihydro-indeno[1,2-b]pyrrol-1-yl)-1-methyl-ethylamine fumarate (1:0.5) with m.p. 206° were obtained.

EXAMPLE 22 a) A solution of 2 g of (RS)-2-(2-oxoethyl)-6-methoxy-1-indanone and 80 mg of p-toluenesulfonic acid in 70 ml of anhydrous toluene was heated on a water separator. A solution of 2.94 g of (RS)-1-amino-2-propanol in 20 ml of anhydrous toluene was added dropwise to the boiling solution over a period of 5 minutes. Subsequently, the mixture was boiled for an additional 30 minutes, during which the solvent was reduced to a volume of 20 ml. The cooled reaction mixture was purified by column chromatography on silica gel (ethyl acetate/toluene 1:1). 1.7 g (71%) of (RS)-1-(7-methoxy-1,4-dihydro-indeno[1,2-b]pyrrol-1-yl)-propan-2-ol were obtained as a solid with m.p. 76°.

b) 0.64 ml of methanesulfonyl chloride was added dropwise while stirring to a solution, cooled to 0° C., of 1 g of (RS)-1-(7-methoxy-1,4-dihydro-indeno[1,2-b]pyrrol-1-yl)-propan-2-ol and 2.3 ml of triethylamine in 30 ml of dichloromethane and the mixture was stirred at this temperature for an additional 1.5 hours. The reaction mixture was subsequently diluted with 200 ml of diethyl ether, washed twice with 70 ml of saturated sodium hydrogen carbonate solution each time and the combined aqueous phases were extracted once with 70 ml of diethyl ether. The combined organic phases were washed with 70 ml of saturated sodium chloride solution, dried over magnesium sulfate and evaporated in a vacuum. The brown oil obtained was dissolved in 40 ml of anhydrous dimethylformamide, treated with 0.53 g of sodium azide and the reaction mixture was heated to 60° for 15 hours while stirring. After cooling, the solution was poured into 140 ml of water and extracted twice with 140 ml of diethyl ether each time. The combined organic phases were washed once with 100 ml of water and once with 100 ml of saturated sodium chloride solution, dried over magnesium sulfate and the solution was concentrated in a vacuum. The brown oil obtained was purified by column chromatography on silica gel (toluene). 750 mg (68%) of (RS)-1-(2-azido-propyl)-7-methoxy-1,4-dihydro-indeno[1,2-b]pyrrole as a colorless oil.

c) 1 g of (RS)-1-(2-azido-propyl)-7-methoxy-1,4-dihydro-indeno[1,2-b]pyrrole dissolved in 50 ml of anhydrous ethanol was hydrogenated on 100 mg of platinum oxide for 3 hours. The catalyst was subsequently filtered off, rinsed with ethanol and the solvent was drawn off in a vacuum. The colorless oil obtained was dissolved in 100 ml of anhydrous diethyl ether, filtered and treated while stirring with a solution of 216 mg of fumaric acid in 20 ml of methanol. The mixture was stirred at room temperature for 18 hours and the white crystals were subsequently filtered off. 882 mg (79%) of (RS)-2-(7-methoxy-1,4-dihydro-indeno[1,2-b]pyrrol-1-yl)-1-methyl-ethylamine fumarate (1:0.5) with m.p. 203° were obtained.

EXAMPLE 23 a) A solution of 20.0 g of 6-methoxy-1-indanone, 31.3 ml of 3-buten-2-ol, 53.5 ml of 2,2-dimethoxypropane and 200 mg of p-toluenesulfonic acid in 200 ml of toluene was brought to boiling. The resulting methanol/acetone mixture was distilled off and the reaction solution was subsequently boiled under reflux overnight. After cooling, the solution was washed with 50 ml of saturated sodium hydrogen carbonate solution. The aqueous washing was extracted with 50 ml of ethyl acetate, the organic phases were combined, dried with magnesium sulfate and evaporated in a vacuum. Purification on silica gel (hexane/diethyl ether 5:1) yielded 13.6 g (55%) of (RS)-2-(2-buten-1-yl)-6-methoxy-1-indanone as a pale yellow oil.

b) Ozone (3 g ozone/hour) was conducted for 60 minutes while stirring through a solution, cooled to −70°, of 13.6 g of (RS)-2-(2-buten-1-yl)-6-methoxy-1-indanone in 200 ml of anhydrous dichloromethane and 400 ml of anhydrous methanol. Subsequently, the solution was flushed with oxygen and then 6.4 ml of dimethyl sulfide were added to the cold solution. The solution came to room temperature overnight and was evaporated in a vacuum. The residue was dissolved in 1600 ml of dichloromethane. The solution was treated with 600 g of silica gel and 100 ml of 10% oxalic acid solution and stirred overnight. Then, the mixture was filtered and the filtrate was concentrated in a vacuum. 6.5 g (51%) of (RS)-2-(2-oxoethyl)-6-methoxy-1-indanone were obtained as a yellow oil.

c) A solution of 4.5 g of (RS)-2-(2-oxoethyl)-6-methoxy-1-indanone and 2.3 g of N-acetylethylenediamine in 100 ml of toluene was boiled under reflux for 10 minutes. The reaction mixture was evaporated in a vacuum, taken up in dichloromethane, dried with magnesium sulfate and again evaporated. After purification on silica gel (ethyl acetate), 0.9 g (15%) of N-[2-(7-methoxy-1,4-dihydro-indeno[1,2-b]pyrrol-1-yl)-ethyl]-acetamide was obtained as a yellowish solid.

d) 2.4 g of N-[2-(7-methoxy-1,4-dihydro-indeno[1,2-b]pyrrol-1-yl)-ethyl]-acetamide were heated to 140° for 17 hours under argon in 48 ml of ethylene glycol/water 2:1 in the presence of 2.5 g of potassium hydroxide. The mixture was left to cool and treated with 250 ml of semi-saturated sodium chloride solution. The mixture was extracted three times with diethyl ether and the combined extracts were dried over sodium sulfate, filtered and evaporated. The brown oil was dissolved in 30 ml of methanol and treated with 1.0 g of fumaric acid, following which pale brown crystals separated. These were dissolved in 120 ml of warm methanol. After cooling to room temperature the product was crystallized out by the slow addition of 120 ml of diethyl ether. 2.0 g (66%) of 2-(7-methoxy-1,4-dihydro-indeno[1,2-b]pyrrol-1-yl)-ethylamine fumarate (1:1) with m.p. 177°–180° were obtained.

EXAMPLE 24 a) A solution of 2.0 g of (RS)-2-(2-oxoethyl)-5-fluoro-1-indanone and 85 mg of p-toluenesulfonic acid in 70 ml of anhydrous toluene was heated on a water separator. A solution of 3.12 g of (RS)-1-amino-2-propanol in 20 ml of anhydrous toluene was added dropwise to the boiling solution over a period of 5 minutes. Subsequently, the mixture was boiled for an additional 45 minutes, during which the solvent was reduced to a volume of 20 ml. The cooled reaction mixture was purified by column chromatography on silica gel (ethyl acetate/toluene 2:3). 1.66 g (69%) of (RS)-1-(6-fluoro-1,4-dihydro-indeno[1,2-b]pyrrol-1-yl)-propan-2-ol were obtained as a brown oil.

b) 1.12 ml of methanesulfonyl chloride were added dropwise while stirring to a solution, cooled to 0°, of 1.66 g of (RS)-1-(6-fluoro-1,4-dihydro-indeno[1,2-b]pyrrol-1-yl)-propan-2-ol and 3.98 ml of triethylamine in 60 ml of dichloromethane and the mixture was stirred at this temperature for an additional 1.5 hours. The reaction mixture was subsequently diluted with 70 ml of dichloromethane, washed twice with 70 ml of saturated sodium hydrogen carbonate solution each time and the combined aqueous phases were extracted once with 70 ml of dichloromethane. The combined organic phases were washed with 70 ml of saturated sodium chloride solution, dried over magnesium sulfate and evaporated in a vacuum. The brown oil obtained was dissolved in 50 ml of anhydrous dimethylformamide, treated with 0.82 g of sodium azide and the reaction mixture was heated to 60° for 17 hours while stirring. After cooling, the solution was poured into 80 ml of water and extracted three times with 100 ml of ethyl acetate each time. The combined organic phases were washed once with 70 ml of water and once with 70 ml of saturated sodium chloride solution, dried over magnesium sulfate and the solution was concentrated in a vacuum. The brown oil obtained was purified by column chromatography on silica gel (toluene). 0.45 g (24%) of (RS)-1-(2-azido-propyl)-6-fluoro-1,4-dihydro-indeno[1,2-b]pyrrole was obtained as a yellow oil.

c) 0.44 g of (RS)-1-(2-azido-propyl)-6-fluoro-1,4-dihydro-indeno[1,2-b]pyrrole dissolved in 30 ml of anhydrous ethanol were hydrogenated on 45 mg of platinum oxide for 5 hours. The catalyst was subsequently filtered off, rinsed with ethanol and the solvent was drawn off in a vacuum. The colorless oil obtained was dissolved in 40 ml of anhydrous diethyl ether, filtered and treated while stirring with a solution of 100 mg of fumaric acid in 7 ml of methanol. The mixture was stirred at room temperature for 15 hours and the white crystals were subsequently filtered off. 0.39 g (80%) of (RS)-2-(6-fluoro-1,4-dihydro-indeno[1,2-b]pyrrol-1-yl)-1-methyl-ethylamine fumarate (1:0.5) with m.p. 202° was obtained.

EXAMPLE 25 a) A solution of 10.6 g of 5,6-difluoro-1-indanone, 13.1 ml of 3-buten-2-ol and 110 mg of p-toluenesulfonic acid in 110 ml of 2,2-dimethoxy-propane was boiled under reflux for 64 hours on a water separator filled with molecular sieve (0.4 nm, 2 mm pearl shaped). The reaction mixture was subsequently concentrated in a vacuum and purified by column chromatography on silica gel (hexane/diethyl ether 2:1). In addition to 3.6 g of educt there were obtained 5.32 g (38%) of (RS)-2-(2-buten-1-yl)-5,6-difluoro-1-indanone as a brown oil.

b) An ozone stream (2 g ozone/hour) was conducted for 40 minutes while stirring through a solution, cooled to −70°, of 5.3 g of (RS)-2-(2-buten-1-yl)-5,6-difluoro-1-indanone in 125 ml of anhydrous dichloromethane and 25 ml of anhydrous methanol. Subsequently, the mixture was flushed with oxygen for 5 minutes and with argon for 10 minutes. After the addition of 2.64 ml of dimethyl sulfide, the mixture was stirred at room temperature for 16 hours. The reaction mixture was evaporated in a vacuum, the residue was treated with 60 ml of dichoromethane and, after the addition of 10 ml of water and 10 ml of trifluoroacetic acid, stirred at room temperature for 2 hours. The mixture was subsequently poured into 80 ml of water and neutralized by the spatula-wise addition of sodium hydrogen carbonate while stirring. An additional 40 ml of water were added, the phases were separated and the aqueous phase was extracted twice with 100 ml of dichloromethane each time. The combined organic phases were dried over magnesium sulfate and concentrated in a vacuum. There was obtained a yellow oil which was crystallized from diethyl ether/hexane. 3.82 g (76%) of (RS)-2-(2-oxoethyl)-5,6-difluoro-1-indanone were obtained as a white solid with m.p. 78°–81°.

c) A solution of 2.1 g of (RS)-2-(2-oxoethyl)-5,6-difluoro-1-indanone and 80 mg of p-toluenesulfonic acid in 70 ml of anhydrous toluene was heated on a water separator. A solution of 3.0 g of (R)-1-amino-2-propanol in 20 ml of anhydrous toluene was added dropwise to the boiling solution over a period of 5 minutes. Subsequently, the mixture was boiled for an additional 45 minutes, during which the solvent was reduced to a volume of 20 ml. The cooled reaction mixture was purified by column chromatography on silica gel (diethyl ether/hexane 7:3). 1.13 g (45%) of (R)-1-(6,7-difluoro-1,4-dihydro-indeno[1,2-b]pyrrol-1-yl)-propan-2-ol were obtained as a brown solid which was used without further recrystallization in the next reaction.

d) 0.7 ml of methanesulfonyl chloride was added dropwise while stirring to a solution, cooled to 0°, of 1.13 g of (R)-1-(6,7-difluoro-1,4-dihydro-indeno[1,2-b]pyrrol-1-yl)-propan-2-ol and 2.48 ml of triethylamine in 50 ml of dichloromethane and the mixture was stirred at this temperature for an additional 1.5 hours. The reaction mixture was subsequently diluted with 70 ml of dichloromethane, washed twice with 60 ml of saturated sodium hydrogen carbonate solution each time and the combined aqueous phases were extracted once with 60 ml of dichloromethane. The combined organic phases were washed with 90 ml of saturated sodium chloride solution, dried over magnesium sulfate and evaporated in a vacuum. The brown oil obtained was dissolved in 40 ml of anhydrous dimethylformamide, treated with 0.58 g of sodium azide and the reaction mixture was heated to 60° for 17 hours while stirring. After cooling, the solution was poured into 70 ml of water and extracted three times with 70 ml of ethyl acetate each time. The combined organic phases were washed once with 70 ml of water and once with 70 ml of saturated sodium chloride solution, dried over magnesium sulfate and the solution was concentrated in a vacuum. The brown oil obtained was purified by column chromatography on silica gel (hexane/ethyl acetate 4:1). 0.97 g (79%) of (S)-1-(2-azido-propyl)-6,7-difluoro-1,4-dihydro-indeno[1,2-b]pyrrole was obtained as a colorless oil.

e) 0.97 g of (S)-1-(2-azido-propyl)-6,7-difluoro-1,4-dihydro-indeno[1,2-b]pyrrole dissolved in 50 ml of anhydrous ethanol were hydrogenated on 100 mg of platinum oxide for 18 hours. The catalyst was subsequently filtered off, rinsed with ethanol and the solvent was drawn off in a vacuum. The colorless oil obtained was dissolved in 75 ml of anhydrous diethyl ether, filtered and treated while stirring with a solution of 406 mg of fumaric acid in 20 ml of methanol. The mixture was stirred at room temperature for 22 hours and the white crystals were subsequently filtered off. 0.78 g (61%) of (S)-2-(6,7-difluoro-1,4-dihydro-indeno[1,2-b]pyrrol-1-yl)-1-methyl-ethylamine fumarate (1:1) with m.p. 215°–217° was obtained.

EXAMPLE 26 a) A solution of 14.5 g of 5-chloro-6-methoxy-3,3-dimethyl-1-indanone, 13.3 ml of 3-buten-2-ol and 300 mg of p-toluenesulfonic acid in 150 ml of 2,2-dimethoxy-propane was boiled under reflux for 71 hours on a water separator filled with molecular sieve (0.4 nm 2 mm, pearl shaped). The reaction mixture was subsequently concentrated in a vacuum and purified by column chromatography on silica gel (hexane/diethyl ether 6:1). In addition to 2.25 g of educt, there were obtained 11.9 g (66%) of (RS)-2-(2-buten-1-yl)-5-chloro-6-methoxy-3,3-dimethyl-1-indanone as a pale yellow solid with m.p. 86°.

b) An ozone stream (3 g ozone/hour) was conducted for 50 minutes while stirring through a solution, cooled to −70°, of 11.9 g of (RS)-2-(2-buten-1-yl)-5-chloro-6-methoxy-3,3-dimethyl-1-indanone in 160 ml of anhydrous dichloromethane and 40 ml of anhydrous methanol. Subsequently, the mixture was flushed with oxygen for 5 minutes and with argon for 10 minutes. After the addition of 4.7 ml of dimethyl sulfide, the mixture was stirred at room temperature for 16 hours. The reaction mixture was evaporated in a vacuum, the residue was treated with 120 ml of dichoromethane and, after the addition of 20 ml of water and 20 ml of trifluoroacetic acid, stirred at room temperature for 2 hours. The mixture was subsequently poured into 150 ml of water and neutralized by the spatula-wise addition of sodium hydrogen carbonate while stirring. An additional 50 ml of water were added. The phases were separated and the aqueous phase was extracted twice with 100 ml of dichloromethane each time. The combined organic phases were dried over magnesium sulfate and concentrated in a vacuum. The oil obtained was crystallized from hexane/ethyl acetate. 10.3 g (90%) of (RS)-2-(2-oxoethyl)-5-chloro-6-methoxy-3,3-dimethyl-1-indanone were obtained as a light yellow solid with m.p. 102°–103°.

c) A solution of 6.67 g of (RS)-2-(2-oxoethyl)-5-chloro-6-methoxy-3,3-dimethyl-1-indanone and 150 mg of p-toluenesulfonic acid in 200 ml of anhydrous toluene was heated on a water separator. A solution of 7.51 g of (R)-1-amino-2-propanol in 40 ml of anhydrous toluene was added dropwise to the boiling solution over a period of 5 minutes. Subsequently, the mixture was boiled for an additional 45 minutes, during which the solvent was reduced to a volume of 40 ml. The cooled reaction mixture was purified by column chromatography on silica gel (ethyl acetate/hexane 1:1). 7.0 g (92%) of (R)-1-(6-chloro-7-methoxy-4,4-dimethyl-1,4-dihydro-indeno[1,2-b]pyrrol-1-yl)-propan-2-ol were obtained as a brown oil.

d) 0.93 ml of methanesulfonyl chloride were added dropwise while stirring to a solution, cooled to 0°, of 1.84 g of (R)-1-(6-chloro-7-methoxy-4,4-dimethyl-1,4-dihydro-indeno[1,2-b]pyrrol-1-yl)-propan-2-ol and 3.35 ml of triethylamine in 50 ml of dichloromethane and the mixture was stirred at this temperature for an additional 1.5 hours. The reaction mixture was subsequently diluted with 150 ml of dichloromethane, washed twice with 90 ml of saturated sodium hydrogen carbonate solution each time and the combined aqueous phases were extracted once with 70 ml of dichloromethane. The combined organic phases were washed with 90 ml of saturated sodium chloride solution, dried over magnesium sulfate and evaporated in a vacuum. The green oil obtained was dissolved in 50 ml of anhydrous dimethylformamide, treated with 0.78 g of sodium azide and the reaction mixture was heated to 60° for 17 hours while stirring. After cooling the solution was poured into 70 ml of water and extracted twice with 100 ml of ethyl acetate each time. The combined organic phases were washed once with 70 ml of water and once with 70 ml of saturated sodium chloride solution, dried over magnesium sulfate and the solution was concentrated in a vacuum. The brown oil obtained was purified by column chromatography on silica gel (hexane/ethyl acetate 3:1). 1.58 g (80%) of (S)-1-(2-azido-propyl)-6-chloro-7-methoxy-4,4-dimethyl-1,4-dihydro-indeno[1,2-b]pyrrole were obtained as a red oil.

e) 1.56 g of (S)-1-(2-azido-propyl)-6-chloro-7-methoxy-4,4-dimethyl-1,4-dihydro-indeno[1,2-b]pyrrole dissolved in 100 ml of anhydrous ethanol were hydrogenated on 160 mg of platinum oxide for 16 hours. The catalyst was subsequently filtered off, rinsed with ethanol and the solvent was drawn off in a vacuum. The light yellow oil obtained was dissolved in 125 ml of anhydrous diethyl ether, filtered and treated while stirring with a solution of 548 mg of fumaric acid in 15 ml of methanol. The mixture was stirred at room temperature for 19 hours and the white crystals were subsequently filtered off. 1.57 g (80%) of (S)-2-(6-chloro-7-methoxy-4,4-dimethyl-1,4-dihydro-indeno[1,2-b]pyrrol-1-yl)-1-methyl-ethylamine fumarate (1:1) with m.p. 186°–188° were obtained.

EXAMPLE 27 a) A solution of 1.92 g of (RS)-2-(2-oxoethyl)-6-fluoro-1-indanone and 80 mg of p-toluenesulfonic acid in 90 ml of anhydrous toluene was heated on a water separator. A solution of 3.0 g of (S)-1-amino-2-propanol in 20 ml of anhydrous toluene was added dropwise to the boiling solution over a period of 5 minutes. Subsequently, the mixture was boiled for an additional 30 minutes, during which the solvent was reduced to a volume of 20 ml. The cooled reaction mixture was purified by column chromatography on silica gel (ethyl acetate/toluene 2:3). 1.51 g (65%) of (S)-1-(7-fluoro-1,4-dihydro-indeno[1,2-b]pyrrol-1-yl)-propan-2-ol were obtained as a brown oil.

b) 0.51 ml of methanesulfonyl chloride was added dropwise while stirring to a solution, cooled to 0°, of 1.51 g of (S)-1-(7-fluoro-1,4-dihydro-indeno[1,2-b]pyrrol-1-yl)-propan-2-ol and 3.64 ml of triethylamine in 40 ml of dichloromethane and the mixture was stirred at this temperature for an additional 1.5 hours. The reaction mixture was subsequently diluted with 100 ml of dichloromethane, washed twice with 60 ml of saturated sodium hydrogen carbonate solution each time and the combined aqueous phases were extracted once with 70 ml of dichloromethane. The combined organic phases were washed with 70 ml of saturated sodium chloride solution, dried over magnesium sulfate and evaporated in a vacuum. The brown oil obtained was dissolved in 30 ml of anhydrous dimethylformamide, treated with 711 mg of sodium azide and the reaction mixture was heated to 50° for 16 hours while stirring. After cooling, the solution was poured into 110 ml of water and extracted twice with 110 ml of ethyl acetate each time. The combined organic phases were washed once with 90 ml of water and once with 90 ml of saturated sodium chloride solution, dried over magnesium sulfate and the solution was concentrated in a vacuum. The brown oil obtained was purified by column chromatography on silica gel (toluene). 631 mg (38%) of (R)-1-(2-azido-propyl)-7-fluoro-1,4-dihydro-indeno[1,2-b]pyrrole were obtained as an oil.

c) 620 mg of (R)-1-(2-azido-propyl)-7-fluoro-1,4-dihydro-indeno[1,2-b]pyrrole dissolved in 30 ml of anhydrous ethanol were hydrogenated on 62 mg of platinum oxide for 15 hours. The catalyst was subsequently filtered off, rinsed with ethanol and the solvent was drawn off in a vacuum. The colorless oil obtained was dissolved in 75 ml of anhydrous diethyl ether, filtered and treated while stirring with a solution of 140 mg of fumaric acid in 15 ml of methanol. The mixture was stirred at room temperature for 4.5 hours and the white crystals were subsequently filtered off. 409 mg (53%) of (R)-2-(7-fluoro-1,4-dihydro-indeno[1,2-b]pyrrol-1-yl)-1-methyl-ethylamine fumarate (1:1) with m.p. 174° were obtained.

EXAMPLE 28 a) A solution of 2 g of (RS)-2-(2-oxoethyl)-6-methoxy-1-indanone and 80 mg of p-toluenesulfonic acid in 70 ml of anhydrous toluene was heated on a water separator. A solution of 2.94 g of (S)-1-amino-2-propanol in 20 ml of anhydrous toluene was added dropwise to the boiling solution over a period of 5 minutes. Subsequently, the mixture was boiled for an additional 30 minutes, during which the solvent was reduced to a volume of 20 ml. The cooled reaction mixture was purified by column chromatography on silica gel (ethyl acetate/toluene 1:1). 1.5 g (63%) of (S)-1-(7-methoxy-1,4-dihydro-indeno[1,2-b]pyrrol-1-yl)-propan-2-ol were obtained as a solid with m.p. 74°.

b) 0.96 ml of methanesulfonyl chloride was added dropwise while stirring to a solution, cooled to 0°, of 1.5 g of (S)-1-(7-methoxy-1,4-dihydro-indeno[1,2-b]pyrrol1-yl)-propan-2-ol and 3.45 ml of triethylamine in 50 ml of dichloromethane and the mixture was stirred at this temperature for an additional 1.5 hours. The reaction mixture was subsequently diluted with 200 ml of diethyl ether, washed twice with 70 ml of saturated sodium hydrogen carbonate solution each time and the combined aqueous phases were extracted once with 70 ml of diethyl ether. The combined organic phases were washed with 70 ml of saturated sodium chloride solution, dried over magnesium sulfate and evaporated in a vacuum. The brown oil obtained was dissolved in 60 ml of anhydrous dimethylformamide, treated with 0.71 g of sodium azide and the reaction mixture was heated to 60° for 15 hours while stirring. After cooling the solution was poured into 140 ml of water and extracted twice with 140 ml of diethyl ether each time. The combined organic phases were washed once with 100 ml of water and with 100 ml of saturated sodium chloride solution, dried over magnesium sulfate and the solution was concentrated in a vacuum. The brown oil obtained was purified by column chromatography on silica gel (toluene). 1.0 g (60%) of (R)-1-(2-azido-propyl)-7-methoxy-1,4-dihydro-indeno[1,2-b]pyrrole was obtained as a colorless oil.

c) 1 g of (R)-1-(2-azido-propyl)-7-methoxy-1,4-dihydro-indeno[1,2-b]pyrrole dissolved in 50 ml of anhydrous ethanol was hydrogenated on 100 mg of platinum oxide for 4 hours. The catalyst was subsequently filtered off, rinsed with ethanol and the solvent was drawn off in a vacuum. The colorless oil obtained was dissolved in 100 ml of anhydrous diethyl ether, filtered and treated while stirring with a solution of 240 mg of fumaric acid dissolved in 20 ml of methanol. The mixture was stirred at room temperature for 18 hours and the white crystals were subsequently filtered off. 760 mg (68%) of (R)-2-(7-methoxy-1,4-dihydro-indeno[1,2-b]pyrrol-1-yl)-1-methyl-ethylamine fumarate (1:0.5) with m.p. 207° were obtained.

EXAMPLE 29 a) A solution of 2.5 g of (RS)-2-(2-oxoethyl)-6-chloro-1-indanone and 100 mg of p-toluenesulfonic acid in 120 ml in anhydrous toluene was heated on a water separator. A solution of 3.6 g of (S)-1-amino-2-propanol in 20 ml of anhydrous toluene was added dropwise to the boiling solution over a period of 5 minutes. Subsequently, the mixture was boiled for 30 minutes, during which the solvent was reduced to a volume of 20 ml. The cooled reaction mixture was purified by column chromatography on silica gel (ethyl acetate/toluene 1:1). 1.56 g (53%) of (S)-1-(7-chloro-1,4-dihydro-indeno[1,2-b]pyrrol-1-yl)-propan-2-ol were obtained as a brown oil which was used directly in the next reaction.

(b) 0.97 ml of methanesulfonyl chloride was added dropwise while stirring to a solution, cooled to 0°, of 1.55 g of (S)-1-(7-chloro-1,4-dihydro-indeno[1,2-b]pyrrol-1-yl)-propan-2-ol and 3.5 ml of triethyl-amine in 40 ml of diohloromethane and the mixture was stirred at this temperature for an additional 1.5 hours. The reaction mixture was subsequently diluted with 200 ml of dichloromethane, washed twice with 70 ml of saturated sodium hydrogen carbonate solution each time and the combined aqueous phases were extracted once with 70 ml of dichloromethane. The combined organic phases were washed to 70 ml of saturated sodium chloride solution, dried over magnesium sulfate and evaporated in a vacuum. The brown oil obtained was dissolved in 30 ml of anhydrous dimethylformamide, treated with 815 mg of sodium azide and the reaction mixture was heated to 60° for 17 hours while stirring. After cooling, the solution was poured into 140 ml of water and extracted twice with 140 ml of ethyl acetate each time. The combined organic phases were washed once with 140 ml of water and once with 140 ml of saturated sodium chloride solution, dried over magnesium sulfate and the solution was concentrated in a vacuum. The brown oil obtained was purified by column chromatography on silica gel (toluene). 833 mg (49%) of (R)-1-(2-azido-propyl)-7-chloro-1,4-dihydro-indeno[1,2-b]pyrrole were obtained as an oil.

c) 750 mg of (R)-1-(2-azido-propyl)-7-chloro-1,4-dihydro-indeno[1,2-b]pyrrole dissolved in 30 ml of anhydrous ethanol were hydrogenated on 75 mg of platinum oxide for 16 hours. Subsequently, the catalyst was filtered off under suction, rinsed with ethanol and the solvent was drawn off in a vacuum. The colorless oil obtained was dissolved in 70 ml of anhydrous diethyl ether, filtered and treated while stirring with a solution of 154 mg of fumaric acid in 15 ml of methanol. The mixture was stirred at room temperature for 6 hours and the white crystals were subsequently filtered off. 633 mg (76%) of (R)-2-(7-chloro-1,4-dihydro-indeno[1,2-b]pyrrol-1-yl)-1-methyl-ethylamine fumarate (1:0.5) with m.p. 195° were obtained.

EXAMPLE 30 a) A solution of 3 g of (RS)-2-(2-oxoethyl)-7-methoxy-1-tetralone and 150 mg of p-toluenesulfonic acid in 130 ml in anhydrous toluene was heated on a water separator. A solution of 4.16 g of (S)-1-amino-2-propanol in 20 ml of anhydrous toluene was added dropwise to the boiling solution over a period of 5 minutes. Subsequently, the mixture was boiled for an additional 30 minutes, during which the solvent was reduced to a volume of 25 ml. The cooled reaction mixture was purified by column chromatography on silica gel (ethyl acetate/toluene 1:1). 3.0 g (84%) of (S)-1-(4,5-dihydro-8-methoxy-1H-benz[g]indol-1-yl-propan-2-ol were obtained as a brown oil which was used directly in the next reaction.

(b) 1.8 ml of methanesulfonyl chloride were added dropwise while stirring to a solution, cooled to 0°, of 3 g of (S)-1-(4,5-dihydro-8-methoxy-1H-benz[g]indol-1-yl-propan-2-ol and 6.55 ml of triethyl-amine in 80 ml of dichloromethane and the mixture was stirred at this temperature for an additional 1.5 hours. The reaction mixture was subsequently diluted with 300 ml of diethyl ether, washed twice with 100 ml of saturated sodium hydrogen carbonate solution each time and the combined aqueous phases were extracted once with 100 ml of diethyl ether. The combined organic phases were washed with 100 ml of saturated sodium chloride solution, dried over magnesium sulfate and evaporated in a vacuum. The oil obtained was dissolved in 70 ml of anhydrous dimethylformamide, treated with 1.52 g of sodium azide and the reaction mixture was heated to 60° for 15 hours while stirring. After cooling, the solution was poured into 140 ml of water and extracted twice with 140 ml of diethyl ether each time. The combined organic phases were washed once with 100 ml of water and once with 100 ml of saturated sodium chloride solution, dried over magnesium sulfate and the solution was concentrated in a vacuum. The brown oil obtained was purified by column chromatography on silica gel (toluene). 1.9 g (58%) of (R)-1-(2-azido-propyl)-4,5-dihydro-8-methoxy-1H-benz[g]indole were obtained as a light yellow oil.

c) 1.9 g of (R)-1-(2-azido-propyl)-4,5-dihydro-8-methoxy-1H-benz[g]indole dissolved in 100 ml of anhydrous ethanol were hydrogenated on 190 mg of platinum oxide for 16 hours. The catalyst was subsequently filtered off, rinsed with ethonal and the solvent was drawn off in a vacuum. There were obtained 1.64 g (95%) of (R)-2-(4,5- dihydro-8-methoxy-1H-benz[g]indol-1-yl)-1-methyl-ethylamine as a colorless oil, of which 440 mg were dissolved in 70 ml of anhydrous ether, filtered and treated while stirring with a solution of 200 mg of fumaric acid in 20 ml of methanol the mixture was stirred at room temperature for 2 hours and the white crystals were subsequently filtered off. 450 mg (70%) of (R)-2-(4,5-dihydro-8-methoxy-1H-benz[g]indol-1-yl)-1-methyl-ethylamine fumarate (1:1) with m.p. 194° were obtained.

EXAMPLE 31 a) A solution of 1.2 g of (R)-2-(4,5-dihydro-8-methoxy-1H-benz[g]indol-1-yl)-1-methyl-ethylamine, 0.52 g of triethylamine and 0.83 g of ethyl trifluoroacetate in 50 ml of anhydrous methanol was stirred at room temperature for 27 hours. After the solvent had been drawn off in a vacuum, the residue was taken up with 70 ml of anhydrous dioxane, 1.8 g of DDQ were added and the mixture was boiled under reflux for 1.5 hours, Subsequently, the reaction mixture was concentrated in a vacuum and the residue was purified by column chromatography on silica gel (dichloromethane/acetone 4:1). 0.97 g (59%) of (R)-N-[2-(8-methoxy-1H-benz[g]indol-1-yl)-1-methyl-ethyl]-trifluoroacetamide was obtained as a pale brown solid which was used in the next reaction without additional recrystallization.

b) A mixture of 0.97 g of (R)-N-[2-(8-methoxy-1H-benz[g]indol-1-yl)-1-methyl-ethyl]-trifluoroacetamide, 1 g of potassium hydroxide, 2 ml of water and 40 ml of methanol was boiled under reflux for 15 hours. The reaction mixture was subsequently poured into 80 ml of 1N sodium hydroxide solution, extracted twice with 80 ml of diethyl ether each time and once with 80 ml of ethyl acetate and the combined organic phases were washed once with 120 ml and dried over magnesium sulfate. After concentration in a vacuum, the residue was dissolved in 100 ml of anhydrous diethyl ether, filtered and treated while stirring with a solution of 322 mg of fumaric acid in 30 ml of methanol. The mixture was stirred at room temperature for 3 hours and the white crystals were subsequently filtered off. 600 mg (69%) of (R)-2-(8-methoxy-1H-benz[g]indol-1-yl)-1-methyl-ethylamine fumarate (1:0.5) with m.p. 209° were obtained.

EXAMPLE 32 a) 254 mg of N-[2-(4,5-dihydro-8-methoxy-1H-benz[g]indol-1-yl)ethyl]-acetamide were dissolved in 10 ml of dioxane under argon, 238 mg of DDQ were added and the mixture was heated to reflux for 1 hour. Separated crystals were removed by filtration, the filtrate was evaporated and the residue was chromatographed on 50 g of silica gel with methylene chloride/acetone 9:1. 211 mg (83%) of N-[2-(8-methoxy-1H-benz[g]indol-1-yl)ethyl]-acetamide were obtained as a light yellowish solid. Tlc (silica gel): Rf=0.25 (methylene chloride/acetone 9:1).

b) 211 mg of N-[2-(8-methoxy-1H-benz[g]indol-1-yl)ethyl]-acetamide were heated to 140° for 9.5 hr. under argon in 3 ml of ethylene glycol/water 2:1 in the presence of 0.25 g of potassium hydroxide. The reaction mixture was left to cool and was poured into 20 ml of semi-concentrated sodium chloride solution. The mixture was extracted three times with diethyl ether and the combined extracts were washed once with saturated sodium chloride solution, dried over sodium sulfate, filtered and evaporated. The crude product was dissolved in 2 ml of methanol and 70 mg of fumaric acid were added. After the addition of 5 ml of diethyl ether, the crystals were filtered off and recrystallized from 8.5 ml of methanol/DMF 16:1. 142 mg (53%) of 2-(8-methoxy-1H-benz[g]indol-1-yl)-ethylamine fumarate (1:1) were obtained as white crystals with m.p. 200°–201°.

EXAMPLE 33 a) A solution of 20 g of 5,6-dimethoxy-1-indanone, 21.5 ml (0.25 mol) of 3-buten-2-ol and 200 mg of p-toluenesulfonic acid in 21.5 ml of 2,2-dimethoxypropane and 200 ml of anhydrous toluene was boiled under reflux for 24 hours. The reaction mixture was subsequently concentrated in a vacuum and purified by column chromatography on silica gel (hexane/ethyl acetate 3:2). 6.8 g (27%) of (RS)-2-(2-buten-1-yl)-5,6-dimethoxy-1-indanone were obtained as a yellow oil.

b) An ozone stream (3 g ozone/hour) was conducted while stirring for 30 minutes through a solution, cooled to −70°, of 6.8 g of (RS)-2-(2-buten-1-yl)-5,6-dimethoxy-1-indanone in 100 ml of anhydrous dichloromethane and 20 ml of anhydrous methanol. Subsequently, the solution was flushed with oxygen for 5 minutes and with argon for 10 minutes. After the addition of 4 ml of dimethyl sulfide, the mixture was stirred at room temperature for 15 hours. The reaction mixture was evaporated in a vacuum, the residue was treated with 250 ml of dichloromethane and, after the addition of 10 ml of water and 10 ml of trifluoroacetic acid, stirred at room temperature for 1.5 hours. The mixture was subsequently poured into 100 ml of water and neutralized while stirring by the spatula-wise addition of sodium hydrogen carbonate. An additional 70 ml of water were added, the phases were separated and the aqueous phase was extracted twice with 120 ml of dichloromethane each time. The combined organic phases were dried over magnesium sulfate, concentrated in a vacuum and the crude product obtained was crystallized from diethyl ether/hexane. 4.7 g (73%) of (RS)-2-(2-oxoethyl)-5,6-dimethoxy-1-indanone were obtained as a light yellow solid with m.p. 122°.

c) A solution of 2 g of (RS)-2-(2-oxoethyl)-5,6-dimethoxy-1-indanone and 80 mg of p-toluenesulfonic acid in 70 ml of anhydrous toluene was heated on a water separator. A solution of 2.56 g of (RS)-1-amino-2-propanol in 20 ml of anhydrous toluene was added dropwise to the boiling solution over a period of 5 minutes. Subsequently, the mixture was boiled for an additional 30 minutes, during which the solvent was reduced to a volume of 20 ml. The cooled reaction mixture was purified by column chromatography on silica gel (ethyl acetate/toluene 2:3). 0.91 g (40%) of (RS)-1-(1,4-dihydro-6,7-dimethoxy-indeno[1,2-b]pyrrol-1-yl)-propan-2-ol was obtained as an oil.

d) 0.52 ml of methanesulfonyl chloride was added dropwise while stirring to a solution, cooled to 0°, of 0.91 g of (RS)-1-(1,4-dihydro-6,7-dimethoxy-indeno[1,2-b]pyrrol-1-yl)-propan-2-ol and 1.86 ml of triethylamine in 25 ml of dichloromethane and the mixture was stirred at this temperature for an additional 1.5 hours. The reaction mixture was subsequently diluted with 140 ml of dichloromethane, washed twice with 70 ml of saturated sodium hydrogen carbonate solution each time and the combined aqueous phases were extracted once with 70 ml of dichloromethane. The combined organic phases were washed with 70 ml of saturated sodium chloride solution, dried over magnesium sulfate and evaporated in a vacuum. The brown oil obtained was dissolved in 40 ml of anhydrous dimethylformamide, treated with 0.43 g of sodium azide and the reaction mixture was heated to 60° for 15 hours while stirring. After cooling, the solution was poured into 140 ml of water and extracted twice with 140 ml of ethyl acetate each time. The combined organic phases were washed once with 100 ml of water and once with 100 ml of saturated sodium chloride solution, dried over magnesium sulfate and the solution was concentrated in a vacuum. The brown oil obtained was purified by column chromatography on silica gel (toluene/ethyl acetate 4:1). 400 mg (40%) of (RS)-1-(2-azido-propyl)-1,4-dihydro-6,7-dimethoxy-indeno[1,2-b]pyrrole were obtained as an oil which was used in the next reaction without further purification.

e) 0.4 g of (RS)-1-(2-azido-propyl)-1,4-dihydro-6,7-dimethoxy-indeno[1,2-b]pyrrole dissolved in 20 ml of anhydrous ethanol was hydrogenated on 40 mg of platinum oxide for 16 hours. The catalyst was subsequently filtered off, rinsed with ethanol and the solvent was drawn off in a vacuum. The colorless oil obtained was dissolved in 25 ml of anhydrous diethyl ether, filtered and treated while stirring with a solution of 62.2 mg of fumaric acid in 5 ml of methanol. The mixture was stirred at room temperature for 18 hours and the white crystals were subsequently filtered off. 314 mg (71%) of (RS)-2-(1,4-dihydro-6,7-dimethoxy-indeno[1,2-b]pyrrol-1-yl)-1-methyl-ethylamine fumarate with m.p. 203°–205° were obtained.

EXAMPLE 34 a) A solution of 48 g of 4-chromanone, 67 ml of 3-buten-2-ol and 500 mg of p-toluenesulfonic acid in 67 ml of 2,2-dimethoxypropane and 500 ml of anhydrous toluene was boiled under reflux for 46 hours. The reaction mixture was subsequently concentrated in a vacuum and purified by column chromatography on silica gel (hexane/diethyl ether 4:1). 24.7 g (38%) of (RS)-2-(2-buten-1-yl)-4-chromanone were obtained as a yellow oil.

b) An ozone stream (3.5 g ozone/hour) was conducted while stirring for 2 hours through a solution, cooled to –70°, of 24.6 g of (RS)-2-(2-buten-1-yl)-4-chromanone in 450 ml of anhydrous dichloromethane and 150 ml of anhydrous methanol. Subsequently, the solution was flushed with oxygen for 5 minutes and with argon for 15 minutes. After the addition of 13.4 ml of dimethyl sulfide, the mixture was stirred at room temperature for 20 hours. The reaction mixture was subsequently evaporated in a vacuum. The residue was treated with 250 ml of dichloromethane and, after the addition of 40 ml of water and 40 ml of trifluoroacetic acid, stirred at room temperature for 4 hours. The mixture was subsequently poured into 100 ml of water and neutralized by the spatula-wise addition of sodium hydrogen carbonate while stirring. An additional 70 ml of water were added, the phases were separated and the aqueous phase was extracted twice with 120 ml of dichloromethane each time. The combined organic phases were dried over magnesium sulfate and concentrated in a vacuum. 22.7 g (99%) of 2-(2-oxoethyl)-4-chromanone were obtained as a yellow oil which was used in the next reaction without additional purification.

c) A solution of 1.9 g of (RS)-2-(2-oxoethyl)-4-chromanone and 80 mg of p-toluenesulfonic acid in 70 ml of anhydrous toluene was heated on a water separator. A solution of 3.0 g of (RS)-1-amino-2-propanol in 20 ml of anhydrous toluene was added dropwise to the boiling solution over a period of 5 minutes. Subsequently, the mixture was boiled for an additional 35 minutes, during which the solvent was reduced to a volume of 20 ml. The cooled reaction mixture was purified by column chromatography on silica gel (ethyl acetate/toluene 2:3). 1.82 g (79%) of (RS)-1-(1,4-dihydro-[1]benzopyrano[4,3-b]pyrrol-1-yl)-propan-2-ol were obtained as a yellow oil.

d) 1.23 ml of methanesulfonyl chloride were added dropwise while stirring to a solution, cooled to 0°, of 1.82 g of (RS)-1-(1,4-dihydro-[1]benzopyrano[4,3-b]pyrrol-1-yl)-propan-2-ol and 4.4 ml of triethyl-amine in 50 ml of anhydrous dichloromethane and the mixture was stirred at this temperature for an additional 1.5 hours. The reaction mixture was subsequently diluted with 280 ml of diethyl ether, washed twice with 70 ml of saturated sodium hydrogen carbonate solution each time and the combined aqueous phases were extracted once with 70 ml of diethyl ether. The combined organic phases were washed with 140 ml of saturated sodium chloride solution, dried over magnesium sulfate and evaporated in a vacuum. The brown oil obtained was dissolved in 50 ml of anhydrous dimethylformamide treated with 1.03 g of sodium azide and the reaction mixture was heated to 60° for 17 hours while stirring. After cooling, the solution was poured into 140 ml of water and extracted twice with 140 ml of diethyl ether each time. The combined organic phases were washed once with 100 ml of water and once with 100 ml of saturated sodium chloride solution, dried over magnesium sulfate and the solution was concentrated in a vacuum. The brown oil obtained was purified by column chromatography on silica gel (toluene). 1.44 g (71%) of (RS)-1-(2-azido-propyl)-1,4-dihydro-[1]benzopyrano[4,3-b]pyrrole were obtained as a colorless oil.

e) 1.44 g of (RS)-1-(2-azido-propyl)-1,4-dihydro-[1]benzo-pyrano[4,3-b]pyrrole dissolved in 60 ml of anhydrous ethanol were hydrogenated on 150 mg of platinum oxide for 4 hours. The catalyst was subsequently filtered off, rinsed with ethanol and the solvent was drawn off in a vacuum. The colorless oil obtained was dissolved in 100 ml of anhydrous diethyl ether, filtered and treated while stirring with a solution of 329 mg of fumaric acid in 20 ml of methanol. The mixture was stirred at room temperature for 18 hours and the white crystals were subsequently filtered off. 1.42 g (88%) of (RS)-1-(1,4-dihydro-[1]benzopyrano-[4,3-b] pyrrol-1-yl)-1-methyl-ethylamine fumarate (1:0.5) with m.p. 208°–209° were obtained.

EXAMPLE 35 a) A lithium diisopropylamide solution, freshly prepared from 3.12 ml of diisopropylamine and 13.8 ml of 1.6N n-butyllithium in hexane, in 40 ml of anhydrous tetrahydrofuran was added dropwise while stirring to a solution, cooled to –70°, of 2.96 g of 6-methoxy-1-indanone in 300 ml of anhydrous tetrahydrofuran. The mixture was stirred at this temperature for an additional 30 minutes and a solution of 2.03 ml of 3-chloro-2-butenone dissolved in 40 ml of anhydrous tetrahydrofuran was subsequently added dropwise over 10 minutes. The reaction mixture was left to come to room temperature over 30 minutes and was stirred at this temperature for a further 30 minutes. Subsequently, the reaction mixture was poured on to 150 ml of ice, 150 ml of saturated sodium chloride were added and the organic phase was separated. The aqueous phase was extracted once with 400 ml of diethyl ether, the combined organic phases were washed once with 200 ml of saturated sodium chloride solution, dried over magnesium sulfate and concentrated in a vacuum. The red oil obtained was purified by column chromatography on silica gel (hexane/diethyl ether 3:2). In addition to 0.93 g of educt there were obtained 1.56 g (37%) of rac-6-methoxy-2-(3-oxo-2-butyl)-1-indanone as a yellow oil.

b) A solution of 1.5 g of rac-6-methoxy-2-(3-oxo-2-butyl)-1-indanone and 80 mg of p-toluenesulfonic acid in 70 ml of anhydrous toluene was heated on a water separator. A solution of 1.94 g of (R)-1-amino-2-propanol in 20 ml of anhydrous toluene was added dropwise to the boiling solution over a period of 5 minutes. Subsequently, the mixture was boiled for an additional 85 minutes, during which the solvent was reduced to a volume of 20 ml. The cooled reaction mixture was purified by column chromatography on silica gel (ethyl acetate/toluene 2:3). 1.23 g (70%) of (R)-1-(7-methoxy-2,3-dimethyl-1,4-dihydro-indeno[1,2-b]pyrrol-1-yl)-propan-2-ol were obtained as a yellow oil.

c) 0.7 ml of methanesulfonyl chloride was added dropwise while stirring to a solution, cooled to 0°, of 1.22 g of (R)-1-(7-methoxy-2,3-dimethyl-1,4-dihydro-indeno[1,2-b]pyrrol-1-yl)-propan-2-ol and 2.5 ml of triethylamine in 50 ml of dichloromethane and the mixture was stirred at this temperature for an additional 1.5 hours. The reaction mixture was subsequently diluted with 100 ml of dichloromethane, washed twice with 60 ml of saturated sodium hydrogen carbonate solution each time and the combined aqueous phases were extracted once with 60 ml of dichloromethane. The combined organic phases were washed with 70 ml of saturated sodium chloride solution, dried over magnesium sulfate and evaporated in a vacuum. The green oil obtained was dissolved in 40 ml of anhydrous dimethylformamide, treated with 0.58 g of sodium azide and the reaction mixture was heated to 80° for 18 hours while stirring. After cooling the solution was poured into 70 ml of water and extracted twice times with 100 ml of ethyl acetate each time. The combined organic phases were washed once with 70 ml of water and once with 70 ml of saturated sodium chloride solution, dried over magnesium sulfate and the solution was concentrated in a vacuum. The brown oil obtained was purified by column chromatography on silica gel (toluene). 0.64 g (48%) of (S)-1-(2-azido-propyl)-7-methoxy-2,3-dimethyl-1,4-dihydro-indeno[1,2-b]pyrrole were obtained as a light yellow oil.

d) 0.63 g of (S)-1-(2-azido-propyl)-7-methoxy-2,3-dimethyl-1,4-dihydro-indeno[1,2-b]pyrrole dissolved in 40 ml of anhydrous ethanol were hydrogenated on 63 mg of platinum oxide for 2.5 hours. The catalyst was subsequently filtered off, rinsed with ethanol and the solvent was drawn off in a vacuum. The colorless oil obtained was dissolved in 50 ml of anhydrous diethyl ether, filtered and treated while stirring with a solution of 123 mg of fumaric acid in 10 ml of methanol. The mixture was stirred at room temperature for 16 hours and the light yellow crystals were subsequently filtered off. 528 mg (76) of (S)-2-(7-methoxy-2,3-dimethyl-1,4-dihydro-indeno[1,2-b]pyrrol-1-yl)-1-methyl-ethylamine fumarate (1:05) with m.p. 197° were obtained.

EXAMPLE 36 a) A lithium diisopropylamide solution, freshly prepared from 3.12 ml of diisopropylamine and 13.8 ml of 1.6N n-butyllithium in hexane, in 40 ml of anhydrous tetrahydrofuran was added dropwise while stirring to a solution, cooled to −70°, of 2.96 g of 6-methoxy-1-indanone in 300 ml of anhydrous tetrahydrofuran. The mixture was stirred at this temperature for an additional 30 minutes and a solution of 1.62 ml of chloroacetone dissolved in 40 ml of anhydrous tetrahydrofuran was subsequently added dropwise over 10 minutes. The reaction mixture was left to come to room temperature over 90 minutes and was stirred at this temperature for an additional 45 minutes. Subsequently, the reaction mixture was poured on to 100 ml of ice, 100 ml of saturated sodium chloride were added and the organic phase was separated. The aqueous phase was extracted once with 300 ml of diethyl ether. The combined organic phases were washed once with 100 ml of saturated sodium chloride solution, dried over magnesium sulfate and concentrated in a vacuum. The red oil obtained was purified by column chromatography on silica gel (hexane/diethyl ether 3:2).

There were obtained 2.24 g (56%) of (RS)-6-methoxy-2-(2-oxopropyl)-1-indanone as a yellow solid which was used without further recrystallization in the next reaction.

b) A solution of 1.45 g of (RS)-6-methoxy-2-(2-oxopropyl)-1-indanone and 60 mg of p-toluenesulfonic acid in 70 ml of anhydrous toluene was heated on a water separator. A solution of 2.0 g of (R)-1-amino-2-propanol in 20 ml of anhydrous toluene was added dropwise to the boiling solution over a period of 5 minutes. Subsequently, the mixture was boiled for an additional 90 minutes, during which time the solvent was reduced to a volume of 20 ml. The cooled reaction mixture was purified by column chromatography on silica gel (ethyl acetate/toluene 2:3). 1.05 g (61%) of (R)-1-(7-methoxy-2-methyl-1,4-dihydro-indeno[1,2-b]pyrrol-1-yl)-propan-2-ol were obtained as a yellow solid with m.p. 110°.

c) 0.48 ml of methanesulfonyl chloride was added dropwise while stirring to a solution, cooled to 0°, of 0.8 g of (R)-1-(7-methoxy-2-methyl-1,4-dihydro-indeno[1,2-b]pyrrol-1-yl)-propan-2-ol and 1.73 ml of triethylamine in 40 ml of dichloromethane and the mixture was stirred at this temperature for an additional 1.5 hours. The reaction mixture was subsequently diluted with 100 ml of dichloromethane, washed twice with 70 ml of saturated sodium hydrogen carbonate solution each time and the combined aqueous phases were extracted once with 60 ml of dichloromethane. The combined organic phases were washed with 70 ml of saturated sodium chloride solution, dried over magnesium sulfate and evaporated in a vacuum. The brown oil obtained was dissolved in 25 ml of anhydrous dimethylformamide, treated with 0.40 g of sodium azide and the reaction mixture was heated to 60° for 16 hours while stirring. After cooling, the solution was poured into 70 ml of water and extracted twice with 100 ml of ethyl acetate each time. The combined organic phases were washed once with 70 ml of water and once with 70 ml of saturated sodium chloride solution, dried over magnesium sulfate and the solution was concentrated in a vacuum. The brown oil obtained was purified by column chromatography on silica gel (toluene). 0.44 g (50%) of (S)-1-(2-azido-propyl)-7-methoxy-2-methyl-1,4-dihydro-indeno[1,2-b]pyrrole was obtained as a light yellow oil.

d) 0.44 g of (S)-1-(2-azido-propyl)-7-methoxy-2-methyl-1,4-dihydro-indeno[1,2-b]pyrrole dissolved in 35 ml of anhydrous ethanol was hydrogenated on 45 mg of platinum oxide for 16 hours. The catalyst was subsequently filtered off, rinsed with ethanol and the solvent was drawn off in a vacuum. The light yellow oil obtained was dissolved in 35 ml of anhydrous diethyl ether, filtered and treated while stirring with a solution of 90 mg of fumaric acid in 7 ml of methanol. The mixture was stirred at room temperature for 18 hours and the light yellow crystals were subsequently filtered off. 414 mg (84%) of (S)-2-(7-methoxy-2-methyl-1,4-dihydro-indeno[1,2-b]pyrrol-1-yl)-1-methyl-ethylamine fumarate (1:0.5) with m.p. 199° were obtained.

EXAMPLE 37 a) A solution of 14.0 g of 4-chloro-1-indanone, 17.3 ml of 3-buten-2-ol and 140 mg of p-toluenesulfonic acid in 140 ml of 2,2-dimethoxy-propane was boiled under reflux for 64 hours on a water separator filled with molecular sieve (0.4 nm, 2 mm pearl shaped). The reaction mixture was subsequently concentrated in a vacuum and purified by column chromatography on silica gel (hexane/diethyl ether 6:1). 15.2 g (81%) of (RS)-2-(2-buten-1-yl)-4-chloro-1-indanone were obtained as a yellow oil.

b) An ozone stream (3 g ozone/hour) was conducted for 90 minutes while stirring through a solution, cooled to −70°, of 15.1 g of (RS)-2-(2-buten-1-yl)-4-chloro-1-indanone in 200 ml of anhydrous dichloromethane and 40 ml of anhydrous methanol. Subsequently, the solution was flushed with oxygen for 5 minutes and with argon for 10 minutes. After the addition of 7.55 ml of dimethyl sulfide the mixture was stirred at room temperature for 20 hours. The reaction mixture was evaporated in a vacuum. The residue was treated with 200 ml of dichoromethane and, after the addition of 25 ml of water and 25 ml of trifluoroacetic acid, stirred at room temperature for 2 hours. The mixture was subsequently poured into 200 ml of water and neutralized by the spatula-wise addition of sodium hydrogen carbonate while stirring. An additional 100 ml of water were added. The phases were separated and the aqueous phase was extracted twice with 120 ml of dichloromethane each time. The combined organic phases were dried over magnesium sulfate and concentrated in a vacuum. 13.9 g (97%) of (RS)-2-(2-oxoethyl)-4-chloro-1-indanone were obtained as a light yellow oil.

c) A solution of 2.08 g of (RS)-2-(2-oxoethyl)-4-chloro-1-indanone and 80 mg of p-toluenesulfonic acid in 70 ml of anhydrous toluene was heated on a water separator. A solution of 3.0 g of (RS)-1-amino-2-propanol in 20 ml of anhydrous toluene was added dropwise to the boiling solution over a period of 5 minutes. Subsequently, the mixture was boiled for an additional 45 minutes, during which the solvent was reduced to a volume of 20 ml. The cooled reaction mixture was purified by column chromatography on silica gel (ethyl acetate/hexane 1:2). 1.47 g (59%) of (RS)-1-(5-chloro-1,4-dihydro-indeno[1,2-b]pyrrol-1-yl)-propan-2-ol were obtained as a brown oil.

d) 0.92 ml of methanesulfonyl chloride was added dropwise while stirring to a solution, cooled to 0°, of 1.47 g of (RS)-1-(5-chloro-1,4-dihydro-indeno[1,2-b]pyrrol-1-yl)-propan-2-ol and 3.3 ml of triethyl-amine in 50 ml of dichloromethane and the mixture was stirred at this temperature for an additional 1.5 hours. The reaction mixture was subsequently diluted with 50 ml of dichloromethane, washed twice with 70 ml of saturated sodium hydrogen carbonate solution each time and the combined aqueous phases were extracted once with 70 ml of dichloromethane. The combined organic phases were washed with 70 ml of saturated sodium chloride solution, dried over magnesium sulfate and evaporated in a vacuum. The brown oil obtained was dissolved in 50 ml of anhydrous dimethylformamide, treated with 0.77 g of sodium azide and the reaction mixture was heated to 60° for 17 hours while stirring. After cooling, the solution was poured into 80 ml of water and extracted three times with 100 ml of ethyl acetate each time. The combined organic phases were washed once with 70 ml of water and once with 70 ml of saturated sodium chloride solution, dried over magnesium sulfate and the solution was concentrated in a vacuum. The brown oil obtained was purified by column chromatography on silica gel (hexane/ethyl acetate 4:1). 1.0 g (62%) of (RS)-1-(2-azido-propyl)-5-chloro-1,4-dihydro-indeno[1,2-b]pyrrole was obtained as a light yellow oil.

e) 1.0 g of (RS)-1-(2-azido-propyl)-5-chloro-1,4-dihydro-indeno[1,2-b]pyrrole dissolved in 50 ml of anhydrous ethanol was hydrogenated on 100 mg of platinum oxide for 5 hours. The catalyst was subsequently filtered off, rinsed with ethanol and the solvent was drawn off in a vacuum. The colorless oil obtained was dissolved in 80 ml of anhydrous diethyl ether, filtered and treated while stirring with a solution of 212 mg of fumaric acid in 16 ml of methanol. The mixture was stirred at room temperature for 18 hours and the white crystals were subsequently filtered off. 1.05 g (94%) of (RS)-2-(5-chloro-1,4-dihydro-indeno[1,2-b]pyrrol-1-yl)-1-methyl-ethylamine fumarate (1:0.5) with m.p. 182° were obtained.

EXAMPLE 38 a) A solution of 1.8 g of (RS)-6-methoxy-2-(2-oxoethyl)-1-indanone and 70 mg of p-toluenesulfonic acid in 70 ml of anhydrous toluene was heated on a water separator. A solution of 2.48 g of (RS)-1-amino-2-propanol in 20 ml of anhydrous toluene was added dropwise to the boiling solution over a period of 5 minutes. Subsequently, the mixture was boiled for an additional 90 minutes, during which the solvent was reduced to a volume of 20 ml. The cooled reaction mixture was purified by column chromatography on silica gel (diethyl ether/hexane 7:3). 1.37 g (65%) of (RS)-1-(7-methoxy-2-methyl-1,4-dihydro-indeno[1,2-b]pyrrol-1-yl)-propan-2-ol were obtained as a brown solid which was used directly in the next reaction.

b) 0.81 ml of methanesulfonyl chloride was added dropwise while stirring to a solution, cooled to 0°, of 1.35 g of (RS)-1-(7-methoxy-2-methyl-1,4-dihydro-indeno[1,2-b]pyrrol-1-yl)-propan-2-ol and 2.92 ml of triethylamine in 60 ml of dichloromethane and the mixture was stirred at this temperature for an additional 1.5 hours. The reaction mixture was subsequently diluted with 120 ml of dichloromethane, washed twice with 70 ml of saturated sodium hydrogen carbonate solution each time and the combined aqueous phases were extracted once with 70 ml of dichloromethane. The combined organic phases were washed with 90 ml of saturated sodium chloride solution, dried over magnesium sulfate and evaporated in a vacuum. The brown oil obtained was dissolved in 40 ml of anhydrous dimethylformamide, treated with 0.68 g of sodium azide and the reaction mixture was heated to 80° for 23 hours while stirring. After cooling, the solution was poured into 70 ml of water and extracted twice with 100 ml of ethyl acetate each time. The combined organic phases were washed once with 70 ml of water and once with 70 ml of saturated sodium chloride solution, dried over magnesium sulfate and the solution was concentrated in a vacuum. The brown oil obtained was purified by column chromatography on silica gel (toluene). 0.93 g (63%) of (RS)-1-(2-azido-propyl)-7-methoxy-2-methyl-1,4-dihydro-indeno[1,2-b]pyrrole was obtained as a light yellow oil.

c) 0.92 g of (RS)-1-(2-azido-propyl)-7-methoxy-2-methyl-1,4-dihydro-indeno[1,2-b]pyrrole dissolved in 70 ml of anhydrous ethanol was hydrogenated on 90 mg of platinum oxide for 16 hours. The catalyst was subsequently filtered off, rinsed with ethanol and the solvent was drawn off in a vacuum. The light yellow oil obtained was dissolved in 70 ml of anhydrous diethyl ether, filtered and treated while stirring with a solution of 189 mg of fumaric acid in 15 ml of methanol. The mixture was stirred at room temperature for 18 hours and the light yellow crystals were subsequently filtered off. 800 mg (78%) of (RS)-2-(7-methoxy-2-methyl-1,4-dihydro-indeno[1,2-b]pyrrol-1-yl)-1-methyl-ethylamine fumarate (1:0.5) with m.p. 187°–188° were obtained.

EXAMPLE 39 a) A solution of 11.2 g of 6-isopropyl-1-indanone, 13.3 ml of 3-buten-2-ol and 110 mg of p-toluenesulfonic acid in 110 ml of 2,2-dimethoxy-propane was boiled under reflux for 89 hours on a water separator filled with molecular sieve (0.4 nm, 2 mm pearl shaped). The reaction mixture was subsequently concentrated in a vacuum and purified by column chromatography on silica gel (hexane/diethyl ether 5:1). In addition to 6.6 g of educt, there were obtained 5.6 g (38%) of (RS)-2-(2-buten-1-yl)-6-isopropyl-1-indanone as a yellow oil.

b) An ozone stream (2 g ozone/hour) was conducted for 50 minutes while stirring through a solution, cooled to −70°, of 5.6 g of (RS)-2-(2-buten-1-yl)-6-isopropyl-1-indanone in 125 ml of anhydrous dichloromethane and 25 ml of anhydrous methanol. Subsequently, the solution was flushed with oxygen for 5 minutes and with argon for 10 minutes. After the addition of 2.7 ml of dimethyl sulfide, the mixture was stirred at room temperature for 15 hours. The reaction mixture was evaporated in a vacuum. The residue was treated with 60 ml of dichoromethane and, after the addition of 10 ml of water and 10 ml of trifluoroacetic acid, stirred at room temperature for 3 hours. The mixture was subsequently poured into 50 ml of water and neutralized by the spatula-wise addition of sodium hydrogen carbonate while stirring. An additional 50 ml of water were added, the phases were separated and the aqueous phase was extracted twice with 200 ml of dichloromethane each time. The combined organic phases were dried over magnesium sulfate and concentrated in a vacuum. 5.08 g (95%) of (RS)-2-(2-oxoethyl)-6-isopropyl-1-indanone were obtained as a yellow oil.

c) A solution of 2.16 g of (RS)-2-(2-oxoethyl)-6-isopropyl-1-indanone and 80 mg of p-toluenesulfonic acid in 60 ml of anhydrous toluene was heated on a water separator. A solution of 3.0 g of (RS)-1-amino-2-propanol in 20 ml of anhydrous toluene was added dropwise to the boiling solution over a period of 5 minutes. Subsequently, the mixture was boiled for an additional 45 minutes, during which the solvent was reduced to a volume of 20 ml. The cooled reaction mixture was purified by column chromatography on silica gel (diethyl ether/hexane 7:3). 1.4 g (55%) of (RS)-1-(7-isopropyl-1,4-dihydro-indeno[1,2-b]pyrrol-1-yl)-propan-2-ol were obtained as a brown oil.

d) 0.84 ml of methanesulfonyl chloride was added dropwise while stirring to a solution, cooled to 0°, of 1.38 g of (RS)-1-(7-isopropyl-1,4-dihydro-indeno[1,2-b]pyrrol-1-yl)-propan-2-ol and 3.01 ml of triethylamine in 50 ml of dichloromethane and the mixture was stirred at this temperature for an additional 1.5 hours. The reaction mixture was subsequently diluted with 150 ml of dichloromethane, washed twice with 70 ml of saturated sodium hydrogen carbonate solution each time and the combined aqueous phases were extracted once with 70 ml of dichloromethane. The combined organic phases were washed with 100 ml of saturated sodium chloride solution, dried over magnesium sulfate and evaporated in a vacuum. The brown oil obtained was dissolved in 50 ml of anhydrous dimethylformamide, treated with 0.7 g of sodium azide and the reaction mixture was heated to 60° for 17 hours while stirring. After cooling, the solution was poured into 70 ml of water and extracted twice with 100 ml of ethyl acetate each time. The combined organic phases were washed once with 70 ml of water and once with 70 ml of saturated sodium chloride solution, dried over magnesium sulfate and the solution was concentrated in a vacuum. The brown oil obtained was purified by column chromatography on silica gel (toluene). 1.08 g (72%) of (RS)-1-(2-azido-propyl)-7-isopropyl-1,4-dihydro-indeno[1,2-b]pyrrole was obtained as a light yellow oil.

e) 1.06 g of (RS)-1-(2-azido-propyl)-7-isopropyl-1,4-dihydro-indeno[1,2-b]pyrrole dissolved in 50 ml of anhydrous ethanol was hydrogenated on 110 mg of platinum oxide for 4 hours. The catalyst was subsequently filtered off, rinsed with ethanol and the solvent was drawn off in a vacuum. The colorless oil obtained was dissolved in 80 ml of anhydrous diethyl ether, filtered and treated while stirring with a solution of 219 mg of fumaric acid in 15 ml of methanol. The mixture was stirred at room temperature for 15 hours and the white crystals were subsequently filtered off. 918 mg (78%) of (RS)-2-(7-isopropyl-1,4-dihydro-indeno[1,2-b]pyrrol-1-yl)-1-methyl-ethylamine fumarate (1:0.5) with m.p. 203° were obtained.

EXAMPLE 40 a) A solution of 2.16 g of (RS)-2-(2-oxoethyl)-6-isopropyl-1-indanone and 80 mg of p-toluenesulfonic acid in 70 ml of anhydrous toluene was heated on a water separator. A solution of 3.0 g of (R)-1-amino-2-propanol in 20 ml of anhydrous toluene was added dropwise to the boiling solution over a period of 5 minutes. Subsequently, the mixture was boiled for an additional 45 minutes, during which time the solvent was reduced to a volume of 20 ml. The cooled reaction mixture was purified by column chromatography on silica gel (ethyl acetate/toluene 1:1). 1.78 g (70%) of (R)-1-(7-isopropyl-1,4-dihydro-indeno[1,2-b]pyrrol-1-yl)-propan-2-ol were obtained as a brown oil.

b) 1.08 ml of methanesulfonyl chloride were added dropwise while stirring to a solution, cooled to 0°, of 1.78 g of (R)-1-(7-isopropyl-1,4-dihydro-indeno[1,2-b]pyrrol-1-yl)-propan-2-ol and 3.86 ml of triethylamine in 50 ml of dichloromethane and the mixture was stirred at this temperature for an additional 1.5 hours. The reaction mixture was subsequently diluted with 70 ml of dichloromethane, washed twice with 70 ml of saturated sodium hydrogen carbonate solution each time and the combined aqueous phases were extracted once with 70 ml of dichloromethane. The combined organic phases were washed with 100 ml of saturated sodium chloride solution, dried over magnesium sulfate and evaporated in a vacuum. The brown oil obtained was dissolved in 50 ml of anhydrous dimethylformamide, treated with 0.91 g of sodium azide and the reaction mixture was heated to 60° for 16 hours while stirring. After cooling, the solution was poured into 150 ml of water and extracted twice with 200 ml of ethyl acetate each time. The combined organic phases were washed once with 100 ml of water and once with 100 ml of saturated sodium chloride solution, dried over magnesium sulfate and the solution was concentrated in a vacuum. The brown oil obtained was purified by column chromatography on silica gel (toluene). 1.12 g (57%) of (S)-1-(2-azido-propyl)-7-isopropyl-1,4-dihydro-indeno[1,2-b]pyrrole was obtained as a colorless oil.

c) 1.12 g of (S)-1-(2-azido-propyl)-7-isopropyl-1,4-dihydro-indeno[1,2-b]pyrrole dissolved in 100 ml of anhydrous ethanol were hydrogenated on 112 mg of platinum oxide for 3 hours. The catalyst was subsequently filtered off, rinsed with ethanol and the solvent was drawn off in a vacuum. The colorless oil obtained was dissolved in 100 ml of anhydrous diethyl ether, filtered and treated while stirring with a solution of 232 mg of fumaric acid in 10 ml of methanol. The mixture was stirred at room temperature for 5 hours and the white crystals were subsequently filtered off. 371 mg (29%) of (S)-2-(7-isopropyl-1,4-dihydro-indeno[1,2-b]pyrrol-1-yl)-1-methyl-ethylamine fumarate (1:0.57) with m.p. 179°–181° were obtained.

EXAMPLE 41 a) A solution of 11.0 g of 6-tert-butyl-1-indanone, 12.5 ml of 3-buten-2-ol and 110 mg of p-toluenesulfonic acid in 110 ml of 2,2-dimethoxy-propane was boiled under reflux for 41 hours on a water separator filled with molecular sieve (0.4 nm, 2 mm pearl shaped). The reaction mixture was subsequently concentrated in a vacuum and purified by column chromatography on silica gel (hexane/diethyl ether 6:1). 7.35 g (53%) of (RS)-2-(2-buten-1-yl)-6-tert-butyl-1-indanone was obtained as a yellow oil.

b) An ozone stream (3 g ozone/hour) was conducted for 35 minutes while stirring through a solution, cooled to −70°, of 7.35 g of (RS)-2-(2-buten-1-yl)-6-tert-butyl-1-indanone in 150 ml of anhydrous dichloromethane and 30 ml of anhydrous methanol. Subsequently, the solution was flushed with oxygen for 5 minutes and with argon for 10 minutes. After the addition of 3.36 ml of dimethyl sulfide, the mixture was stirred at room temperature for 17 hours. The reaction mixture was evaporated in a vacuum. The residue was treated with 100 ml of dichoromethane and, after the addition of 15 ml of water and 15 ml of trifluoroacetic acid, stirred at room temperature for 3 hours. The mixture was subsequently poured into 100 ml of water and neutralized by the spatula-wise addition of sodium hydrogen carbonate while stirring. An additional 50 ml of water were added. The phases were separated and the aqueous phase was extracted twice with 150 ml of dichloromethane each time. The combined organic phases were dried over magnesium sulfate and concentrated in a vacuum. 6.44 g (92%) of (RS)-2-(2-oxoethyl)-6-tert-butyl-1-indanone were obtained as a yellow oil.

c) A solution of 2.3 g of (RS)-2-(2-oxoethyl)-6-tert-butyl-1-indanone and 80 mg of p-toluenesulfonic acid in 70 ml of anhydrous toluene was heated on a water separator. A solution of 3.0 g of (R)-1-amino-2-propanol in 20 ml of anhydrous toluene was added dropwise to the boiling solution over a period of 5 minutes. Subsequently, the mixture was boiled for an additional 45 minutes, during which time the solvent was reduced to a volume of 20 ml. The cooled reaction mixture was purified by column chromatography on silica gel (ethyl acetate toluene 1:1). 1.9 g (70%) of (R)-1-(7-tert-butyl-1,4-dihydro-indeno[1,2-b]pyrrol-1-yl)-propan-2-ol were obtained as a brown oil.

d) 1.1 ml of methanesulfonyl chloride were added dropwise while stirring to a solution, cooled to 0°, of 1.9 g of (R)-1-(7-tert-butyl-1,4-dihydro-indeno[1,2-b]pyrrol-1-yl)-propan-2-ol and 3.9 ml of triethylamine in 55 ml of dichloromethane and the mixture was stirred at this temperature for an additional 1.5 hours. The reaction mixture was subsequently diluted with 150 ml of dichloromethane, washed twice with 70 ml of saturated sodium hydrogen carbonate solution each time and the combined aqueous phases were extracted once with 70 ml of dichloromethane. The combined organic phases were washed with 100 ml of saturated sodium chloride solution, dried over magnesium sulfate and evaporated in a vacuum. The brown oil obtained was dissolved in 50 ml of anhydrous dimethylformamide, treated with 0.83 g of sodium azide and the reaction mixture was heated to 60° for 16 hours while stirring. After cooling the solution was poured into 120 ml of water and extracted twice with 120 ml of ethyl acetate each time. The combined organic phases were washed once with 100 ml of water and once with 100 ml of saturated sodium chloride solution, dried over magnesium sulfate and the solution was concentrated in a vacuum. The brown oil obtained was purified by column chromatography on silica gel (toluene). 0.82 g (44%) of (S)-1-(2-azido-propyl)-7-tert-butyl-1,4-dihydro-indeno[1,2-b]pyrrole was obtained as a light brown oil.

e) 0.82 g of (S)-1-(2-azido-propyl)-7-tert-butyl-1,4-dihydro-indeno[1,2-b]pyrrole dissolved in 30 ml of anhydrous ethanol was hydrogenated on 80 mg of platinum oxide for 2 hours. The catalyst was subsequently filtered off, rinsed with ethanol and the solvent was drawn off in a vacuum. The colorless oil obtained was dissolved in 50 ml of anhydrous diethyl ether, filtered and treated while stirring with a solution of 163 mg of fumaric acid in 10 ml of methanol. The mixture was stirred at room temperature for 15 hours and the pale pink coloured crystals were subsequently filtered off. 0.33 g (36%) of (S)-2-(7-tert-butyl-1,4-dihydro-indeno[1,2-b]pyrrol-1-yl)-1-methyl-ethylamine fumarate (1:0.5) with m.p. 188°–190° were obtained.

EXAMPLE 42 a) A solution of 9.73 g of 5'-methoxy-2',3'-dihydro-spiro[cyclo-pentane-1,1'-[1H]indene]-3'-one, 9.3 ml of 3-buten-2-ol and 100 mg of p-toluenesulfonic acid in 100 ml of 2,2-dimethoxy-propane was boiled under reflux for 90 hours on a water separator filled with molecular sieve (0.4 nm, 2 mm pearl shaped). The reaction mixture was subsequently concentrated in a vacuum and purified by column chromatography on silica gel (hexane/ethyl acetate 7:1). In addition to 4.0 g of educt, there were obtained 6.24 g (51%) of (RS)-2'-(2-buten-1-yl)-5'-methoxy-2',3'-dihydro-spiro[cyclopentane-1,1'-[1H]indene]-3'-one as a yellow oil.

b) An ozone stream (2.5 g ozone/hour) was conducted for 50 minutes while stirring through a solution, cooled to −70°, of 6.2 g of (RS)-2'-(2-buten-1-yl)-5'-methoxy-2',3'-dihydro-spiro[cyclopentane-1,1'-[1H]indene]-3'-one in 80 ml of anhydrous dichloromethane and 20 ml of anhydrous methanol. Subsequently, the solution was flushed with oxygen for 5 minutes and with argon for 10 minutes. After the addition of 2.52 ml of dimethyl sulfide, the mixture was stirred at room temperature for 17 hours. The reaction mixture was evaporated in a vacuum. The residue was treated with 100 ml of dichoromethane and, after the addition of 15 ml of water and 15 ml of trifluoroacetic acid, stirred at room temperature for 2.5 hours. The mixture was subsequently poured into 150 ml of water and neutralized by the spatula-wise addition of sodium hydrogen carbonate while stirring. An additional 50 ml of water were added. The phases were separated and the aqueous phase was extracted twice with 100 ml of dichloro-methane each time. The combined organic phases were dried over magnesium sulfate and concentrated in a vacuum. 5.74 g (97%) of (RS)-2'-(2-oxoethyl)-5'-methoxy-2',3'-dihydro-spiro[cyclopentane-1,1'-[1H]indene]-3'-one were obtained as a light yellow oil.

c) A solution of 2.58 g of (RS)-2'-(2-oxoethyl)-5'-methoxy-2',3'-dihydro-spiro[cyclopentane-1,1'-[1H]indene]-3'-one and 80 mg of p-toluenesulfonic acid in 70 ml of anhydrous toluene was heated on a water separator. A solution of 3.0 g of (R)-1-amino-2-propanol in 20 ml of anhydrous toluene was added dropwise to the boiling solution over a period of 5 minutes. Subsequently, the mixture was boiled for an additional 45 minutes, during which the solvent was reduced to a volume of 20 ml. The cooled reaction mixture was purified by column chromatography on silica gel (ethyl acetate/hexane 1:1). 1.98 g (67%) of (R)-1-[7'-methoxy-1',4'-dihydro-spiro[cyclopentane-1,4'-indeno[1,2-b]pyrrole]-1'-yl]-propan-2-ol were obtained as a yellow oil.

d) 1.02 ml of methanesulfonyl chloride were added dropwise while stirring to a solution, cooled to 0°, of 1.95 g of (R)-1-[7'-methoxy-1',4'-dihydro-spiro[cyclopentane-1,4'-indeno[1,2-b]pyrrole]-1'-yl]-propan-2-ol and 3.65 ml of triethylamine in 50 ml of dichloromethane and the mixture was stirred at this temperature for an additional 1.5 hours. The reaction mixture was subsequently diluted with 100 ml of dichloromethane, washed twice with 70 ml of saturated sodium hydrogen carbonate solution each time and the combined aqueous phases were extracted once with 70 ml of dichloromethane. The combined organic phases were washed with 70 ml of saturated sodium chloride solution, dried over magnesium sulfate and evaporated in a vacuum. The green oil obtained was dissolved in 50 ml of anhydrous dimethylformamide, treated with 0.86 g of sodium azide and the reaction mixture was heated to 70° for 5 hours while stirring. After cooling, the solution was poured into 70 ml of water and extracted three times with 100 ml of ethyl acetate each time. The combined organic phases were washed once with 70 ml of water and once with 80 ml of saturated sodium chloride solution, dried over magnesium sulfate and the solution was concentrated in a vacuum. The brown oil obtained was purified by column chromatography on silica gel (hexane/ethyl acetate 4:1). 1.45 g (68%) of (S)-1'-(2-azido-propyl)-7'-methoxy-1',4'-dihydro-spiro[cyclopentane]-1,4'-indeno[1,2-b]pyrrole were obtained as a light yellow oil.

e) 1.45 g of (S)-1'-(2-azido-propyl)-7'-methoxy-1',4'-dihydro-spiro[cyclopentane]-1,4'-indeno[1,2-b]pyrrole dissolved in 60 ml of anhydrous ethanol were hydrogenated on 145 mg of platinum oxide for 14 hours. The catalyst was subsequently filtered off, rinsed with ethanol and the solvent was drawn off in a vacuum. The colorless oil obtained was dissolved in 100 ml of anhydrous diethyl ether, filtered and treated while stirring with a solution of 522 mg of fumaric acid in 10 ml of methanol. The mixture was stirred at room temperature for 5 hours and the white crystals were subsequently filtered off. 1.47 g (79%) of (S)-1-methyl-2-(7'-methoxy-1',4'-dihydro-spiro-[cyclopentane]-1,4'-indeno[1,2-b]pyrrol-1-yl)-ethylamine fumarate (1:1) with m.p. 183°–185° were obtained.

EXAMPLE 43 a) A solution of 2.50 g of 5'-methyl-2',3'-dihydro-spiro[cyclo-hexane-1,1'-[1H]indene]-3'-one, 24.1 ml (280 mol) of 3-buten-2-ol and 250 mg of p-toluenesulfonic acid in 250 ml of 2,2-dimethoxy-propane was boiled under reflux for 88 hours on a water separator filled with molecular sieve (0.4 nm, 2 mm pearl shaped). The reaction mixture was subsequently concentrated in a vacuum and purified by column chromatography on silica gel (hexane/ethyl acetate 6:1). In addition to 8.4 g of educt, there were obtained 18.4 g (59%) of (RS)-2'-(2-buten-1-yl)-5'-methyl-2',3'-dihydro-spiro[cyclohexane-1,1'-[1H]indene]-3'-one as a yellow oil.

b) An ozone stream (3 g ozone/hour) was conducted for 75 minutes while stirring through a solution, cooled to –70°, of 18.4 g of (RS)-2'-(2-buten-1-yl)-5'-methyl-2',3'-dihydro-spiro[cyclohexane-1,1'-[1H]indene]-3'-one in 300 ml of anhydrous dichloromethane and 60 ml of anhydrous methanol. Subsequently, the solution was flushed with oxygen for 5 minutes and with argon for 10 minutes. After the addition of 7.55 ml of dimethyl sulfide, the mixture was stirred at room temperature for 16 hours. The reaction mixture was evaporated in a vacuum, the residue was treated with 200 ml of dichoromethane and, after the addition of 30 ml of water and 30 ml of trifluoroacetic acid, stirred at room temperature for 3 hours. The mixture was subsequently poured into 200 ml of water and neutralized by the spatula-wise addition of sodium hydrogen carbonate while stirring. An additional 50 ml of water were added, the phases were separated and the aqueous phase was extracted twice with 150 ml of dichloromethane each time. The combined organic phases were dried over magnesium sulfate and concentrated in a vacuum. 17.0 g (97%) of (RS)-2'-(2-oxoethyl)-5'-methyl-2',3'-dihydro-spiro[cyclohexane-1,1'-[1H]indene]-3'-one were obtained as a yellow oil.

c) A solution of 2.56 g of (RS)-2'-(2-oxoethyl)-5'-methyl-2',3'-dihydro-spiro[cyclohexane-1,1'-[1H]indene]-3'-one and 80 mg of p-toluenesulfonic acid in 70 ml of anhydrous toluene was heated on a water separator. A solution of 3.0 g of (R)-1-amino-2-propanol in 20 ml of anhydrous toluene was added dropwise to the boiling solution over a period of 5 minutes. Subsequently, the mixture was boiled for an additional 45 minutes, during which the solvent was reduced to a volume of 20 ml. The cooled reaction mixture was purified by column chromatography on silica gel (ethyl acetate/hexane 2:3). 2.45 g (83%) of (R)-1-[7'-methyl-1',4'-dihydro-spiro[cyclohexane-1,4'-indeno[1,2-b]pyrrole]-1'-yl]-propan-2-ol were obtained as a brown oil.

d) 1.3 ml of methanesulfonyl chloride were added dropwise while stirring to a solution, cooled to 0°, of 2.45 g of (R)-1-[7'-methyl-1',4'-dihydro-spiro[cyclohexane-1,4'-indeno[1,2-b]pyrrole]-1'-yl]-propan-2-ol and 4.75 ml of triethylamine in 50 ml of dichloromethane and the mixture was stirred at this temperature for an additional 2.5 hours. The reaction mixture was subsequently diluted with 100 ml of dichloromethane, washed twice with 70 ml of saturated sodium hydrogen carbonate solution each time and the combined aqueous phases were extracted once with 70 ml of dichloromethane. The combined organic phases were washed with 70 ml of saturated sodium chloride solution, dried over magnesium sulfate and evaporated in a vacuum. The yellow oil obtained was dissolved in 75 ml of anhydrous dimethylformamide, treated with 1.08 g of sodium azide and the reaction mixture was heated to 60° for 16 hours while stirring. After cooling the solution was poured into 140 ml of water and extracted three times with 100 ml of ethyl acetate each time. The combined organic phases were washed once with 90 ml of water and once with 90 ml of saturated sodium chloride solution, dried over magnesium sulfate and the solution was concentrated in a vacuum. The brown oil obtained was purified by column chromatography on silica gel (hexane/ethyl acetate 4:1). 1.76 g (66%) of (S)-1'-(2-azido-propyl):7'-methyl-1',4'-dihydro-spiro[cyclohexane]-1,4'-indeno[1,2-b]pyrrole were obtained as a light red oil.

e) 1.76 g of (S)-1'-(2-azido-propyl)-7'-methyl-1',4'-dihydro-spiro-[cyclohexane]-1,4'-indeno[1,2-b]pyrrole dissolved in 100 ml of anhydrous ethanol was hydrogenated on 170 mg of platinum oxide for 4 hours. The catalyst was subsequently filtered off, rinsed with ethanol and the solvent was drawn off in a vacuum. The light brown oil obtained was dissolved in 100 ml of anhydrous diethyl ether, filtered and treated while stirring with a solution of 637 mg of fumaric acid in 10 ml of methanol. The mixture was stirred at room temperature for 22 hours and the white crystals were subsequently filtered off. 1.7 g (76%) of (S)-1-methyl-2-(7'-methyl-1',4'-dihydro-spiro[cyclohexane]-1,4'-indeno[1,2-b]pyrrol-1-yl)-ethylamine fumarate (1:1) with m.p. 195°–196° were obtained.

EXAMPLE 44 a) A solution of 17.0 g of 5'-methyl-2',3'-dihydro-spiro[cyclo-pentane-1,1'-[1H]indene]-3'-one, 17.5 ml of 3-buten-2-ol and 170 mg of p-toluenesulfonic acid in 170 ml of 2,2-dimethoxy-propane was boiled under reflux for 71 hours on a water separator filled with molecular sieve (0.4 nm, 2 mm pearl shaped). The reaction mixture was subsequently concentrated in a vacuum and purified by column chromatography on silica gel (hexane/diethyl ether 4:1). In addition to 4.0 g of educt, there were obtained 12.7 g (59%) of (RS)-2'-(2-buten-1-yl)-5'-methyl-2',3'-dihydro-spiro[cyclopentane-1,1'-[1H]indene]-3'-one as a yellow oil.

b) An ozone stream (3 g ozone/hour) was conducted for 60 minutes while stirring through a solution, cooled to −70°, of 12.7 g of (RS)-2'-(2-buten-1-yl)-5'-methyl-2',3'-dihydro-spiro[cyclopentane-1,1'-[1H]indene]-3'-one in 250 ml of anhydrous dichloromethane and 50 ml of anhydrous methanol. Subsequently, the solution was flushed with oxygen for 5 minutes and with argon for 10 minutes. After the addition of 5.54 ml of dimethyl sulfide, the mixture was stirred at room temperature for 17 hours. The reaction mixture was evaporated in a vacuum. The residue was treated with 160 ml of dichoromethane and, after the addition of 15 ml of water and 15 ml of trifluoroacetic acid, stirred at room temperature for 2.5 hours. The mixture was subsequently poured into 150 ml of water and neutralized by the spatula-wise addition of sodium hydrogen carbonate while stirring. An additional 50 ml of water were added. The phases were separated and the aqueous phase was extracted twice with 150 ml of dichloro-methane each time. The combined organic phases were dried over magnesium sulfate and concentrated in a vacuum. 12.0 g (99%) of (RS)-2'-(2-oxoethyl)-5'-methyl-2',3'-dihydro-spiro[cyclopentane-1,1'-[1H]indene]-3'-one were obtained as a light red oil.

c) A solution of 2.42 g of (RS)-2'-(2-oxoethyl)-5'-methyl-2',3'-dihydro-spiro[cyclopentane-1,1'-[1H]indene]-3'-one and 80 mg of p-toluenesulfonic acid in 70 ml of anhydrous toluene was heated on a water separator. A solution of 3.0 g of (R)-1-amino-2-propanol in 20 ml of anhydrous toluene was added dropwise to the boiling solution over a period of 5 minutes. Subsequently, the mixture was boiled for an additional 45 minutes, during which the solvent was reduced to a volume of 20 ml. The cooled reaction mixture was purified by column chromatography on silica gel (diethyl ether/hexane 3:2). 2.06 g (73%) of (R)-1-[7'-methyl-1',4'-dihydro-spiro[cyclopentane-1,4'-indeno[1,2-b]pyrrole]-1'-yl]-propan-2-ol were obtained as a red oil.

d) 1.15 ml of methanesulfonyl chloride were added dropwise while stirring to a solution, cooled to 0°, of 2.06 g of (R)-1-[7'-methyl-1',4'-dihydro-spiro[cyclopentane-1,4'-indeno[1,2-b]pyrrole]-1'-yl]-propan-2-ol and 4.03 ml of triethylamine in 50 ml of dichloromethane and the mixture was stirred at this temperature for an additional 1.5 hours. The reaction mixture was subsequently diluted with 100 ml of dichloromethane, washed twice with 70 ml of saturated sodium hydrogen carbonate solution each time and the combined aqueous phases were extracted once with 70 ml of dichloromethane. The combined organic phases were washed with 70 ml of saturated sodium chloride solution, dried over magnesium sulfate and evaporated in a vacuum. The green oil obtained was dissolved in 75 ml of anhydrous dimethylformamide, treated with 0.95 g of sodium azide and the reaction mixture was heated to 70° for 5 hours while stirring. After cooling the solution was poured into 100 ml of water and extracted three times with 100 ml of ethyl acetate each time. The combined organic phases were washed once with 70 ml of water and once with 70 ml of saturated sodium chloride solution, dried over magnesium sulfate and the solution was concentrated in a vacuum. The brown oil obtained was purified by column chromatography on silica gel (hexane/ethyl acetate 4:1). 1.34 g (66%) of (S)-1'-(2-azido-propyl)-7'-methyl-1',4'-dihydro-spiro[cyclopentane]-1,4'-indeno[1,2-b]pyrrole were obtained as a light red oil.

e) 1.34 g of (S)-1'-(2-azido-propyl)-7'-methyl-1',4'-dihydro-spiro-[cyclopentane]-1,4'-indeno[1,2-b]pyrrole dissolved in 75 ml of anhydrous ethanol was hydrogenated on 135 mg of platinum oxide for 4 hours. The catalyst was subsequently filtered off, rinsed with ethanol and the solvent was drawn off in a vacuum. The colorless oil obtained was dissolved in 80 ml of anhydrous diethyl ether, filtered and treated while stirring with a solution of 507 mg of fumaric acid in 10 ml of methanol. The mixture was stirred at room temperature for 15 hours and the white crystals were subsequently filtered off. 1.23 g (71%) of (S)-1-methyl-2-(7'-methyl-1',4'-dihydro-spiro[cyclopentane]-1,4'-indeno[1,2-b]pyrrol-1-yl)-ethylamine fumarate (1:1) with m.p. 192° were obtained.

EXAMPLE 45 a) A solution of 1.05 g of (RS)-1-(2-azido-propyl)-7-hydroxy-1,4-dihydro-indeno[1,2-b]pyrrole, 0.77 ml of isopropyl bromide and 1.14 g of potassium carbonate in 30 ml of N,N-dimethyl-formamide was heated to 50° for 48 hours. After cooling, the solution was poured into 150 ml of water and extracted twice with 150 ml of ethyl acetate each time. The combined organic phases were washed once with 70 ml of semi-saturated sodium chloride solution, dried over magnesium sulfate and the solution was concentrated in a vacuum. The crude product was purified by column chromatography on silica gel (toluene). 0.35 g (28%) of (RS)-1-(2-azido-propyl)-7-iso-propoxy-1,4-dihydro-indeno[1,2-b]pyrrole was obtained as an orange oil which was used directly in the next reaction.

b) 0.35 g of (RS)-1-(2-azido-propyl)-7-iso-propoxy-1,4-dihydro-indeno[1,2-b]pyrrole dissolved in 40 ml of anhydrous ethanol was hydrogenated on 40 mg of platinum oxide for 4 hours. The catalyst was subsequently filtered off, rinsed with ethanol and the solvent was drawn off in a vacuum. The colorless oil obtained was dissolved in 70 ml of anhydrous diethyl ether, filtered and treated while stirring with a solution of 68 mg of fumaric acid in 10 ml of methanol. The mixture was stirred at room temperature for 17 hours and the white crystals were subsequently filtered off. 0.22 mg (57%) of (RS)-2-(7-isopropoxy-1,4-dihydro-indeno[1,2-b]pyrrol-1-yl)-1-methyl-ethylamine fumarate (1:0.5) with m.p. 192° was obtained.

EXAMPLE 46 a) A solution of 8.0 g of 6-hydroxy-1-indanone, 6.3 ml of cyclopentyl bromide, 16.4 g of potassium carbonate and 10 ml of N,N-dimethylformamide in 100 ml of acetone was heated to 75° for 35 hours. After cooling, the solution was poured into 150 ml of water and extracted twice with 200 ml of ethyl acetate each time. The combined organic phases were washed once with 100 ml of water and once with 100 ml of saturated sodium chloride solution, dried over magnesium sulfate and the solution was concentrated in a vacuum. The crude product was purified by column chromatography on silica gel (hexane/ethyl acetate 3:1). 9.45 g (81%) of 6-cyclopentoxy-1-indanone were obtained as an orange oil which was used directly in the next reaction.

b) A solution of 9.45 g of 6-cyclopentoxy-1-indanone, 9.0 ml of 3-buten-2-ol and 100 mg of p-toluenesulfonic acid in 100 ml of 2,2-dimethoxy-propane was boiled under reflux for 63 hours on a water separator filled with molecular sieve (0.4 nm, 2 mm pearl shaped). The reaction mixture was subsequently concentrated in a vacuum and purified by column chromatography on silica gel (hexane/diethyl ether 6:1). There were obtained 8.1 g (69%) of (RS)-2-(2-buten-1-yl)-6-cyclopentoxy-1-indanone as a yellow oil.

c) An ozone stream (1.5 g ozone/hour) was conducted for 60 minutes while stirring through a solution, cooled to −70°, of 8.1 g of (RS)-2-(2-buten-1-yl)-6-cyclopentoxy-1-indanone in 150 ml of anhydrous dichloromethane and 30 ml of anhydrous methanol. Subsequently, the solution was flushed with oxygen for 5 minutes and with argon for 10 minutes. After the addition of 3.29 ml of dimethyl sulfide, the mixture was stirred at room temperature for 21 hours. The reaction mixture was evaporated in a vacuum. The residue was treated with 75 ml of dichoromethane and, after the addition of 12.5 ml of water and 12.5 ml of trifluoroacetic acid, stirred at room temperature for 5 hours. The mixture was subsequently poured into 150 ml of water and neutralized by the spatula-wise addition of sodium hydrogen carbonate while stirring. An additional 50 ml of water were added. The phases were separated and the aqueous phase was extracted twice with 150 ml of dichloromethane each time. The combined organic phases were dried over magnesium sulfate and concentrated in a vacuum. 5.63 g (73%) of (RS)-2-(2-oxoethyl)-6-cyclopentoxy-1-indanone were obtained as an orange oil.

d) A solution of 2.58 g of (RS)-2-(2-oxoethyl)-6-cyclopentoxy-1-indanone and 80 mg of p-toluenesulfonic acid in 70 ml of anhydrous toluene was heated on a water separator. A solution of 3.0 g of (RS)-1-amino-2-propanol in 20 ml of anhydrous toluene was added dropwise to the boiling solution over a period of 5 minutes. Subsequently, the mixture was boiled for an additional 45 minutes, during which the solvent was reduced to a volume of 20 ml. The cooled reaction mixture was purified by column chromatography on silica gel (diethyl ether/hexane 7:3). 1.44 g (48%) of (RS)-1-(7-cyclopentoxy-1,4-dihydro-indeno[1,2-b]pyrrol-1-yl)-propan-2-ol were obtained as a light yellow oil.

e) 0.75 ml of methanesulfonyl chloride was added dropwise while stirring to a solution, cooled to 0°, of 1.44 g of (RS)-1-(7-cyclopentoxy-1,4-dihydro-indeno[1,2-b]pyrrol-1-yl)-propan-2-ol and 2.66 ml of triethylamine in 55 ml of dichloromethane and the mixture was stirred at this temperature for an additional 1.5 hours. The reaction mixture was subsequently diluted with 100 ml of dichloromethane, washed twice with 70 ml of saturated sodium hydrogen carbonate solution each time and the combined aqueous phases were extracted once with 70 ml of dichloromethane. The combined organic phases were washed with 100 ml of saturated sodium chloride solution, dried over magnesium sulfate and evaporated in a vacuum. The green oil obtained was dissolved in 30 ml of anhydrous dimethylformamide, treated with 0.62 g of sodium azide and the reaction mixture was heated to 60° for 16 hours while stirring. After cooling, the solution was poured into 100 ml of water and extracted twice with 100 ml of ethyl acetate each time. The combined organic phases were washed once with 70 ml of water and once with 70 ml of saturated sodium chloride solution, dried over magnesium sulfate and the solution was concentrated in a vacuum. The brown oil obtained was purified by column chromatography on silica gel (ethyl acetate/hexane 1:4). 1.27 g (82%) of (RS)-1-(2-azido-propyl)-7-cyclopentoxy-1,4-dihydro-indeno[1,2-b]pyrrole were obtained as a light yellowish solid which was used directly in the next reaction.

f) 1.27 g of (RS)-1-(2-azido-propyl)-7-cyclopentoxy-1,4-dihydro-indeno[1,2-b]pyrrole dissolved in 75 ml of anhydrous ethanol was hydrogenated on 125 mg of platinum oxide for 16 hours. The catalyst was subsequently filtered off, rinsed with ethanol and the solvent was drawn off in a vacuum. The light red oil obtained was dissolved in 80 ml of anhydrous diethyl ether, filtered and treated while stirring with a solution of 198 mg of fumaric acid in 20 ml of methanol. The mixture was stirred at room temperature for 17 hours and the pale pink coloured crystals were subsequently filtered off. 926 mg (80%) of (RS)-2-(7-cyclopentoxy-1,4-dihydro-indeno[1,2-b]pyrrol-1-yl)-ethylamine fumarate (1:0.5) with m.p. 196°–198° were obtained.

EXAMPLE 47 a) 12.6 ml of methanesulfonyl chloride were added dropwise while stirring to a solution, cooled to 0°, of 12.0 g of 6-hydroxy-1-indanone and 45.2 ml of triethylamine in 350 ml of dichloro-methane and the solution was stirred at this temperature for an additional 1.5 hours. The reaction mixture was subsequently diluted with 200 ml of dichloromethane, washed twice with 150 ml of saturated sodium hydrogen carbonate solution each time an the combined aqueous phases were extracted once with 100 ml of dichloromethane. The combined organic phases were washed with 200 ml of saturated sodium chloride solution, dried over magnesium sulfate and evaporated in a vacuum. 18.3 g (99%) of 6-mesyloxy-1-indanone were obtained as a brown solid which was used directly in the next reaction.

b) A solution of 18.3 g of 6-mesyloxy-1-indanone, 16.7 ml of 3-buten-2-ol and 300 mg of p-toluenesulfonic acid in 400 ml of 2,2-dimethoxy-propane was boiled under reflux for 46 hours on a water separator filled with molecular sieve (0.4 nm, 2 mm pearl shaped). The reaction mixture was subsequently concentrated in a vacuum and purified by column chromatography on silica gel (hexane/ethyl acetate 4:1). In addition to 8.31 g of educt, there were obtained 11.3 g (50%) of (RS)-2-(2-buten-1-yl)-6-mesyloxy-1-indanone as a yellow oil.

c) An ozone stream (2 g ozone/hour) was conducted for 55 minutes while stirring through a solution, cooled to –70°, of 11.3 g of (RS)-2-(2-buten-1-yl)-6-mesyloxy-1-indanone in 300 ml of anhydrous dichloromethane and 60 ml of anhydrous methanol. Subsequently, the solution was flushed with oxygen for 5 minutes and with argon for 10 minutes. After the addition of 4.51 ml of dimethyl sulfide, the mixture was stirred at room temperature for 15 hours. The reaction mixture was evaporated in a vacuum. The residue was treated with 250 ml of dichoromethane and, after the addition of 25 ml of water and 25 ml of trifluoroacetic acid, stirred at room temperature for 4 hours. The mixture was subsequently poured into 200 ml of water and neutralized by the spatula-wise addition of sodium hydrogen carbonate while stirring. An additional 50 ml of water were added. The phases were separated and the aqueous phase was extracted twice with 200 ml of dichloromethane each time. The combined organic phases were dried over magnesium sulfate and concentrated in a vacuum. 9.38 g (85%) of (RS)-2-(2-oxoethyl)-6-mesyloxy-1-indanone were obtained as a light brown solid with m.p. 85°–87°.

d) A solution of 2.31 g of (RS)-2-(2-oxoethyl)-6-mesyloxy-1-indanone and 110 mg of p-toluenesulfonic acid in 70 ml of anhydrous toluene was heated on a water separator. A solution of 2.58 g of (RS)-1-amino-2-propanol in 20 ml of anhydrous toluene was added dropwise to the boiling solution over a period of 5 minutes. Subsequently, the mixture was boiled for an additional 45 minutes, during which time the solvent was reduced to a volume of 20 ml. The cooled reaction mixture was purified by column chromatography on silica gel (ethyl acetate/hexane 2:3). 0.74 g (28%) of (RS)-1-(7-mesyloxy-1,4-dihydro-indeno[1,2-b]pyrrol-1-yl)-propan-2-ol was obtained as a light brown solid which was used directly in the next reaction.

e) 0.37 ml of methanesulfonyl chloride was added dropwise while stirring to a solution, cooled to 0°, of 0.72 g of (RS)-1-(7-mesyloxy-1,4-dihydro-indeno[1,2-b]pyrrol-1-yl)-propan-2-ol and 1.33 ml of triethylamine in 30 ml of dichloromethane and the mixture was stirred at this temperature for an additional 1.5 hours. The reaction mixture was subsequently diluted with 100 ml of dichloromethane, washed twice with 70 ml of saturated sodium hydrogen carbonate solution each time and the combined aqueous phases were extracted once with 70 ml of dichloromethane. The combined organic phases were washed with 70 ml of saturated sodium chloride solution, dried over magnesium sulfate and evaporated in a vacuum. The green oil obtained was dissolved in 30 ml of anhydrous dimethylformamide, treated with 0.62 g of sodium azide and the reaction mixture was heated to 60° for 16 hours while stirring. After cooling, the solution was poured into 70 ml of water and extracted twice with 100 ml of ethyl acetate each time. The combined organic phases were washed once with 70 ml of water and once with 70 ml of saturated sodium chloride solution, dried over magnesium sulfate and the solution was concentrated in a vacuum. The brown oil obtained was purified by column chromatography on silica gel (ethyl acetate/hexane 1:4). 0.68 g (86%) of (RS)-1-(2-azido-propyl)-7-mesyloxy-1,4-dihydro-indeno[1,2-b]pyrrole was obtained as a light yellowish solid which was used directly in the next reaction.

f) 0.66 g of (S)-1-(2-azido-propyl)-7-mesyloxy-1,4-dihydro-indeno[1,2-b]pyrrole dissolved in 30 ml of anhydrous ethanol was hydrogenated on 66 mg of platinum oxide for 4 hours. The catalyst was subsequently filtered off, rinsed with ethanol and the solvent was drawn off in a vacuum. The light brown oil obtained was dissolved in 50 ml of anhydrous diethyl ether, filtered and treated while stirring with a solution of 116 mg of fumaric acid in 10 ml of methanol. The mixture was stirred at room temperature for 17 hours and the pale pink coloured crystals were subsequently filtered off. 400 mg (55%) of (RS)-2-(7-mesyloxy-1,4-dihydro-indeno[1,2-b]pyrrol-1-yl)-1-methyl-ethylamine fumarate (1:0.5) with m.p. 201° were obtained.

EXAMPLE 48 a) A lithium diisopropylamide solution, freshly prepared from 4.25 ml of diisopropylamine and 18.7 ml of 1.6N n-butyllithium in hexane, in 60 ml of anhydrous tetrahydrofuran was added dropwise while stirring to a solution, cooled to −70°, of 3.24 g of 5-methoxy-1-indanone in 350 ml of anhydrous tetrahydrofuran. The mixture was stirred at this temperature for an additional 30 minutes and a solution of 1.6 ml of chloroacetone dissolved in 60 ml of anhydrous tetrahydrofuran was subsequently added dropwise over 15 minutes. The reaction mixture was left to come to room temperature over 100 minutes and was stirred at this temperature for an additional 45 minutes. Subsequently, the reaction mixture was poured on to 150 ml of ice, 150 ml of saturated sodium chloride were added and the organic phase was separated. The aqueous phase was extracted once with 400 ml of diethyl ether. The combined organic phases were washed once with 100 ml of saturated sodium chloride solution, dried over magnesium sulfate and concentrated in a vacuum. The red oil obtained was purified by column chromatography on silica gel (hexane/diethyl ether 3:7). There were obtained 1.67 g of crude product which was crystallized from diethyl ether/hexane. The crystallization gave 1.21 g (56%) of (RS)-5-methoxy-2-(2-oxopropyl)-1-indanone as a light yellow solid with m.p. 73°.

b) A solution of 1.2 g of (RS)-5-methoxy-2-(2-oxopropyl)-1-indanone and 60 mg of p-toluenesulfonic acid in 70 ml of anhydrous toluene was heated on a water separator. A solution of 1.65 g of (RS)-1-amino-2-propanol in 20 ml of anhydrous toluene was added dropwise to the boiling solution over a period of 5 minutes. Subsequently, the mixture was boiled for an additional 90 minutes, during which the solvent was reduced to a volume of 20 ml. The cooled reaction mixture was purified by column chromatography on silica gel (diethyl ether/hexane 7:3). 1.17 g (82%) of (RS)-1-(6-methoxy-2-methyl-1,4-dihydro-indeno[1,2-b]pyrrol-1-yl)-propan-2-ol were obtained as a yellow solid which was used without further crystallization in the next reaction.

c) 0.7 ml of methanesulfonyl chloride was added dropwise while stirring to a solution, cooled to 0°, of 1.16 g of (RS)-1-(6-methoxy-2-methyl-1,4-dihydro-indeno[1,2-b]pyrrol-1-yl)-propan-2-ol and 2.5 ml of triethylamine in 50 ml of dichloromethane and the mixture was stirred at this temperature for an additional 1.5 hours. The reaction mixture was subsequently diluted with 100 ml of dichloromethane, washed twice with 60 ml of saturated sodium hydrogen carbonate solution each time and the combined aqueous phases were extracted once with 60 ml of dichloromethane. The combined organic phases were washed with 70 ml of saturated sodium chloride solution, dried over magnesium sulfate and evaporated in a vacuum. The brown oil obtained was dissolved in 40 ml of anhydrous dimethyl-formamide, treated with 0.58 g of sodium azide and the reaction mixture was heated to 80° for 16 hours while stirring. After cooling, the solution was poured into 70 ml of water and extracted twice with 100 ml of ethyl acetate each time. The combined organic phases were washed once with 70 ml of water and once with 70 ml of saturated sodium chloride solution, dried over magnesium sulfate and the solution was concentrated in a vacuum. The brown oil obtained was purified by column chromatography on silica gel (toluene). 0.86 g (68%) of (RS)-1-(2-azido-propyl)-6-methoxy-2-methyl-1,4-dihydro-indeno[1,2-b]pyrrole was obtained as a yellow oil.

d) 0.85 g of (S)-1-(2-azido-propyl)-6-methoxy-2-methyl-1,4-dihydro-indeno[1,2-b]pyrrole dissolved in 50 ml of anhydrous ethanol were hydrogenated on 85 mg of platinum oxide for 17 hours. The catalyst was subsequently filtered off, rinsed with ethanol and the solvent was drawn off in a vacuum. The light yellow oil obtained was dissolved in 70 ml of anhydrous diethyl ether, filtered and treated while stirring with a solution of 175 mg of fumaric acid in 15 ml of methanol. The mixture was stirred at room temperature for 19 hours and the slightly white crystals were subsequently filtered off. 779 mg (82%) of (S)-2-(6-methoxy-2-methyl-1,4-dihydro-indeno[1,2-b]pyrrol-1-yl)-1-methyl-ethylamine fumarate (1:0.5) with m.p. 218° were obtained.

EXAMPLE 49 a) A solution of 12.3 g of 5,6-dichloro-1-indanone, 12.6 ml of 3-buten-2-ol and 125 mg of p-toluenesulfonic acid in 125 ml of 2,2-dimethoxy-propane was boiled under reflux for 68 hours on a water separator filled with molecular sieve (0.4 nm, 2 mm pearl shaped). The reaction mixture was subsequently concentrated in a vacuum and purified by column chromatography on silica gel (hexane/diethyl ether 4:1). In addition to 4.3 g of educt, there were obtained 10.8 g (69%) of (RS)-2-(2-buten-1-yl)-5,6-dichloro-1-indanone as a yellow oil.

b) An ozone stream (3.5 g ozone/hour) was conducted for 45 minutes while stirring through a solution, cooled to −70°, of 10.8 g of (RS)-2-(2-buten-1-yl)-5,6-dichloro-1-indanone in 150 ml of anhydrous dichloromethane and 30 ml of anhydrous methanol. Subsequently, the solution was flushed with oxygen for 5 minutes and with argon for 10 minutes.

After the addition of 4.66 ml of dimethyl sulfide, the mixture was stirred at room temperature for 3 hours. The reaction mixture was evaporated in a vacuum. The residue was treated with 150 ml of dichoromethane and, after the addition of 20 ml of water and 20 ml of trifluoroacetic acid, stirred at room temperature for 3 hours. The mixture was subsequently poured into 100 ml of water and neutralized by the spatula-wise addition of sodium hydrogen carbonate while stirring. An additional 50 ml of water were added. The phases were separated and the aqueous phase was extracted twice with 100 ml of dichloromethane each time. The combined organic phases were dried over magnesium sulfate and concentrated in a vacuum. There were obtained 11.6 g of crude product which was crystallized from hexane/ethyl acetate. The crystallization gave 7.59 g (73%) of (RS)-2-(2-oxoethyl)-5,6-dichloro-1-indanone as a light yellow solid with m.p. 93°–96°.

c) A solution of 2.0 g of (RS)-2-(2-oxoethyl)-5,6-dichloro-1-indanone and 70 mg of p-toluenesulfonic acid in 70 ml of anhydrous toluene was heated on a water separator. A solution of 2.47 g of (RS)-1-amino-2-propanol in 20 ml of anhydrous toluene was added dropwise to the boiling solution over a period of 5 minutes. Subsequently, the mixture was boiled for an additional 45 minutes, during which time the solvent was reduced to a volume of 20 ml. The cooled reaction mixture was purified by column chromatography on silica gel (diethyl ether/hexane 4:1). 0.62 g (27%) of (RS)-1-(6,7-dichloro-1,4-dihydro-indeno[1,2-b]pyrrol-1-yl)-propan-2-ol was obtained as a brown oil.

d) 0.33 ml of methanesulfonyl chloride was added dropwise while stirring to a solution, cooled to 0°, of 0.6 g of (RS)-1-(6,7-dichloro-1,4-dihydro-indeno[1,2-b]pyrrol-1-yl)-propan-2-ol and 1.1 8 ml of triethylamine in 30 ml of dichloromethane and the mixture was stirred at this temperature for an additional 1.5 hours. The reaction mixture was subsequently diluted with 50 ml of dichloromethane, washed twice with 70 ml of saturated sodium hydrogen carbonate solution each time and the combined aqueous phases were extracted once with 70 ml of dichloromethane. The combined organic phases were washed with 70 ml of saturated sodium chloride solution, dried over magnesium sulfate and evaporated in a vacuum. The brown oil obtained was dissolved in 50 ml of anhydrous dimethylformamide, treated with 275 mg of sodium azide and the reaction mixture was heated to 60° for 17 hours while stirring. After cooling, the solution was poured into 60 ml of water and extracted three times with 90 ml of ethyl acetate each time. The combined organic phases were washed once with 70 ml of water and once with 70 ml of saturated sodium chloride solution, dried over magnesium sulfate and the solution was concentrated in a vacuum. The brown oil obtained was purified by column chromatography on silica gel (toluene). 0.45 g (69%) of (RS)-1-(2-azido-propyl)-6,7-dichloro-1,4-dihydro-indeno[1,2-b]pyrrole was obtained as a light colorless oil.

e) 0.44 g of (RS)-1-(2-azido-propyl)-6,7-dichloro-1,4-dihydro-indeno[1,2-b]pyrrole dissolved in 30 ml of anhydrous ethanol was hydrogenated on 45 mg of platinum oxide for 3 hours. The catalyst was subsequently filtered off, rinsed with ethanol and the solvent was drawn off in a vacuum. The colorless oil obtained was dissolved in 30 ml of anhydrous diethyl ether, filtered and treated while stirring with a solution of 83 mg of fumaric acid in 5 ml of methanol. The mixture was stirred at room temperature for 18 hours and the white crystals were subsequently filtered off. 395 mg (81%) of (RS)-2-(6,7-dichloro-1,4-dihydro-indeno[1,2-b]pyrrol-1-yl)-1-methyl-ethylamine fumarate (1:0.5) with m.p. 203° were obtained.

EXAMPLE 50 a) A solution of 13.0 g of 4-methyl-1-indanone, 19.2 ml of 3-buten-2-ol and 170 mg of p-toluenesulfonic acid in 170 ml of 2,2-dimethoxy-propane was boiled under reflux for 46 hours on a water separator filled with molecular sieve (0.4 nm, 2 mm pearl shaped). The reaction mixture was subsequently concentrated in a vacuum and purified by column chromatography on silica gel (hexane/diethyl ether 5:1). 12.0 g (67%) of (RS)-2-(2-buten-1-yl)-4-methyl-1-indanone were obtained as a yellow oil.

b) An ozone stream (3 g ozone/hour) was conducted for 90 minutes while stirring through a solution, cooled to –70°, of 12.0 g of (RS)-2-(2-buten-1-yl)-4-methyl-1-indanone in 220 ml of anhydrous dichloromethane and 45 ml of anhydrous methanol. Subsequently, the solution was flushed with oxygen for 5 minutes and with argon for 10 minutes. After the addition of 6.6 ml of dimethyl sulfide, the mixture was stirred at room temperature for 15 hours. The reaction mixture was evaporated in a vacuum, the residue was treated with 160 ml of dichoromethane and, after the addition of 20 ml of water and 20 ml of trifluoroacetic acid, stirred at room temperature for 2 hours. The mixture was subsequently poured into 200 ml of water and neutralized by the spatula-wise addition of sodium hydrogen carbonate while stirring. An additional 50 ml of water were added. The phases were separated and the aqueous phase was extracted twice with 200 ml of dichloromethane each time. The combined organic phases were dried over magnesium sulfate and concentrated in a vacuum. 10.6 g (94%) of (RS)-2-(2-oxoethyl)-4-methyl-1-indanone were obtained as a light yellow oil.

c) A solution of 1.9 g of (RS)-2-(2-oxoethyl)-4-methyl-1-indanone and 80 mg of p-toluenesulfonic acid in 70 ml of anhydrous toluene was heated on a water separator. A solution of 3.0 g of (RS)-1-amino-2-propanol in 20 ml of anhydrous toluene was added dropwise to the boiling solution over a period of 5 minutes. Subsequently, the mixture was boiled for an additional 45 minutes, during which the solvent was reduced to a volume of 20 ml. The cooled reaction mixture was purified by column chromatography on silica gel (diethyl ether/hexane 7:3). 0.63 g (28%) of (RS)-1-(5-methyl-1,4-dihydro-indeno[1,2-b]pyrrol-1-yl)-propan-2-ol was obtained as a white solid which was used directly in the next reaction.

d) 0.44 ml of methanesulfonyl chloride was added dropwise while stirring to a solution, cooled to 0°, of 0.63 g of (RS)-1-(5-methyl-1,4-dihydro-indeno[1,2-b]pyrrol-1-yl)-propan-2-ol and 1.6 ml of triethylamine in 25 ml of dichloromethane and the mixture was stirred at this temperature for an additional 1.5 hours. The reaction mixture was subsequently diluted with 50 ml of dichloromethane, washed twice with 70 ml of saturated sodium hydrogen carbonate solution each time and the combined aqueous phases were extracted once with 70 ml of dichloromethane. The combined organic phases were washed with 70 ml of saturated sodium chloride solution, dried over magnesium sulfate and evaporated in a vacuum. The green solid obtained was dissolved in 30 ml of anhydrous dimethylformamide, treated with 0.36 g of sodium azide and the reaction mixture was heated to 60° for 16 hours while stirring. After cooling, the solution was poured into 80 ml of water and extracted three times with 100 ml of ethyl acetate each time. The combined organic phases were washed once with 70 ml of water and once with 70 ml of saturated sodium chloride solution, dried over magnesium sulfate and the solution was concentrated in a vacuum. The brown oil obtained was purified by column chromatography on silica gel (toluene). 0.69 g (98%) of (RS)-1-(2-azido-propyl)-5-methyl-1,4-dihydro-indeno[1,2-b]pyrrole was obtained as a light yellow oil.

e) 0.69 g of (RS)-1-(2-azido-propyl)-5-methyl-1,4-dihydro-indeno[1,2-b]pyrrole dissolved in 30 ml of anhydrous ethanol was hydrogenated on 70 mg of platinum oxide for 3 hours. The catalyst was subsequently filtered off, rinsed with ethanol and the solvent was drawn off in a vacuum. The colorless oil obtained was dissolved in 80 ml of anhydrous diethyl ether, filtered and treated while stirring with a solution of 157 mg of fumaric acid in 15 ml of methanol. The mixture was stirred at room temperature for 18 hours and the white crystals were subsequently filtered off. 0.34 g (44%) of (RS)-2-(5-methyl-1,4-dihydro-indeno[1,2-b]pyrrol-1-yl)-1-methyl-ethylamine fumarate (1:0.5) with m.p. 214° were obtained.

EXAMPLE 51 a) An ozone stream (3 g ozone/hour) was conducted while stirring during 55 minutes through a solution, cooled to −70°, of 10.1 g of (RS)-2-(2-buten-1-yl)-4-chromanone) in 100 ml of anhydrous dichloromethane and 300 ml of anhydrous methanol. Subsequently, the solution was flushed with oxygen for 5 minutes and with argon for 15 minutes. After the addition of 5 ml of dimethyl sulfide, the mixture was stirred at room temperature for 16 hours. The reaction mixture was evaporated in a vacuum, the residue was dissolved with 5.62 g of N-acetylethylenediamine in 100 ml of concentrated acetic acid and boiled under reflux for 45 minutes. The reaction mixture was subsequently concentrated in a vacuum and the residue was purified by column chromatography on silica gel (ethyl acetate). There were obtained 5.7 g (45%) of N-[2-(1,4-dihydro[1]benzopyrano[4,3-b]pyrrol-1-yl)-ethyl]-acetamide as a brown solid which was used in the next reaction without additional recrystallization.

b) A mixture of 2.5 g of N-[2-(1,4-dihydro[1]benzopyrano[4,3-b]pyrrol-1-yl)-ethyl]-acetamide, 3.28 g of potassium hydroxide, 20 ml of water and 40 ml of ethylene glycol was heated to 110° while stirring for 23 hours. After cooling, the reaction mixture was poured into 100 ml of saturated sodium chloride solution and extracted three times with 200 ml of ethyl acetate each time. The organic phases were washed once with 200 ml of saturated sodium chloride solution, dried over magnesium sulfate and concentrated in a vacuum. The residue was purified by column chromatography on silica gel (dichloromethane/methanol/ammonia 200:10:1). The oil obtained was dissolved in 110 ml of anhydrous diethyl ether, filtered and treated with a solution of 436 mg of fumaric acid in 20 ml of anhydrous methanol. The mixture was stirred at room temperature for 18 hours and the white crystals were subsequently filtered off under suction. 812 mg (31%) of 2-(1,4-dihydro-[1]benzopyrano[4,3-b]pyrrol-1-yl)-ethylamine fumarate (1:0.5) with m.p. 180° were obtained.

EXAMPLE 52 a) A solution of 1.9 g of (RS)-2-(2-oxoethyl)-4-chromanone and 80 mg of p-toluenesulfonic acid in 70 ml of anhydrous toluene was heated on a water separator. A solution of 3.0 g of (R)-1-amino-2-propanol in 20 ml of anhydrous toluene was added dropwise to the boiling solution over a period of 5 minutes. Subsequently, the mixture was boiled for an additional 35 minutes, during which the solvent was reduced to a volume of 20 ml. The cooled reaction mixture was purified by column chromatography on silica gel (ethyl acetate/toluene 3). 1.9 g (83%) of (R)-1-(1,4-dihydro-[1]benzopyrano[4,3-b]pyrrol-1-yl)-propan-2-ol were obtained as a yellow oil.

b) 1.27 ml of methanesulfonyl chloride were added dropwise while stirring to a solution, cooled to 0°, of 1.88 g of (R)-1-(1,4-dihydro-[1]benzopyrano[4,3-b]pyrrol-1-yl)-propan-2-ol and 4.57 ml of triethylamine in 50 ml of anhydrous dichloromethane and the mixture was stirred at this temperature for an additional 1.5 hours. The reaction mixture was subsequently diluted with 280 ml of diethyl ether, washed twice with 70 ml of saturated sodium hydrogen carbonate solution each time and the combined aqueous phases were extracted once with 70 ml of diethyl ether. The combined organic phases were washed with 140 ml of saturated sodium chloride solution, dried over magnesium sulfate and evaporated in a vacuum. The brown solid obtained was dissolved in 50 ml of anhydrous dimethylformamide, treated with 1.0 g of sodium azide and the reaction mixture was heated to 60° for 18 hours while stirring. After cooling the solution was poured into 140 ml of water and extracted twice with 140 ml of diethyl ether each time. The combined organic phases were washed once with 100 ml of water and once with 100 ml of saturated sodium chloride solution, dried over magnesium sulfate and the solution was concentrated in a vacuum. The brown oil obtained was purified by column chromatography on silica gel (toluene). 1.67 g (80%) of (S)-1-(2-azido-propyl)-1,4-dihydro-[1]benzopyrano[4,3-b]-pyrrole were obtained as a colorless oil.

c) 1.65 g of (S)-1-(2-azido-propyl)-1,4-dihydro-[1]benzopyrano[4,3-b]-pyrrole dissolved in 60 ml of anhydrous ethanol were hydrogenated on 170 mg of platinum oxide for 4 hours. The catalyst was subsequently filtered off, rinsed with ethanol and the solvent was drawn off in a vacuum. The thus-obtained colorless oil was dissolved in 100 ml of anhydrous diethyl ether, filtered and treated while stirring with a solution of 309 mg of fumaric acid in 20 ml of methanol. The mixture was stirred at room temperature for 18 hours and the white crystals were subsequently filtered off. 1.35 g (73%) of (S)-1-(1,4-dihydro-[1]benzopyrano[4,3-b]pyrrol-1-yl)-1-methyl-ethylamine fumarate (1:0.5) with m.p. 194°–195° were obtained.

EXAMPLE 53 a) A solution of 25 g of 5-chloro-1-indanone, 31 ml of 3-buten-2-ol and 250 mg of p-toluenesulfonic acid in 31 ml of 2,2-dimethoxy-propane and 250 ml of anhydrous toluene was boiled under reflux for 17 hours. The reaction mixture was subsequently concentrated in a vacuum and purified by column chromatography on silica gel (hexane/diethyl ether 5:1). 11.9 g (36%) of (RS)-2-(2-buten-1-yl)-5-chloro-1-indanone were obtained as a yellow oil.

b) An ozone stream (3 g ozone/hour) was conducted while stirring during 60 minutes through a solution, cooled to −70°, of 11.9 g of (RS)-2-(2-buten-1-yl)-5-chloro-1-indanone in 200 ml of anhydrous dichlomethane and 100 ml of anhydrous methanol. Subsequently, the solution was flushed with oxygen for 5 minutes and with argon for 10 minutes. After the addition of 5.9 ml of dimethyl sulfide, the mixture was stirred at room temperature for 16 hours. The reaction mixture was evaporated in a vacuum. The residue was treated with 50 ml of dichloromethane and, after the addition of 12 ml of water and 12 ml of trifluoroacetic acid, stirred at room temperature for 3 hours. The mixture was subsequently poured into 100 ml of water and neutralized by the spatula-wise addition of sodium hydrogen carbonate while stirring. An additional 100 ml of water were added. The phases were separated and the aqueous phase was extracted twice with 150 ml of dichloromethane each time. The combined organic phases were dried over magnesium sulfate, concentrated in a vacuum and the crude product obtained was crystallized from ethyl acetate/hexane. 8.98 g (80%) of (RS)-2-(2-oxoethyl)-6-chlor-1-indanone were obtained as a white solid with m.p. 66°.

c) A solution of 2 g of (RS)-2-(2-oxoethyl)-6-chlor-1-indanone and 100 mg of p-toluenesulfonic acid in 90 ml of anhydrous toluene was heated on a water separator. A solution of 2.88 g of (RS)-1-amino-2-propanol in 20 ml of anhydrous toluene was added dropwise to the boiling solution over a period of 5 minutes. Subsequently, the mixture was boiled for an additional 35 minutes, during which the solvent was reduced to a volume of 30 ml. The cooled reaction mixture was purified by column chromatography on silica gel (ethyl acetate/toluene 1:1). There were obtained 1.9 g (80%) of (RS)-1-(6-chloro-1,4-dihydro-indeno[1,2-b]pyrrol-1-yl)-propan-2-ol as a brown oil which was used directly in the next reaction.

d) 1.2 ml of methanesulfonyl chloride were added dropwise while stirring to a solution, cooled to 0°, of 1.9 g of (RS)-1-(6-chloro-1,4-dihydro-indeno[1,2-b]pyrrol-1-yl)-propan-2-ol and 4.3 ml of triethyl-amine in 60 ml of dichloromethane and the mixture was stirred at this temperature for an additional 1.5 hours. The reaction mixture was subsequently diluted with 150 ml of dichloromethane, washed twice with 70 ml of saturated sodium hydrogen carbonate solution each time and the combined aqueous phases were extracted once with 70 ml of dichloromethane. The combined organic phases were washed with 70 ml of saturated sodium chloride solution, dried over magnesium sulfate and evaporated in a vacuum. The brown oil obtained was dissolved in 40 ml of anhydrous dimethylformamide, treated with 1.0 g of sodium azide and the reaction mixture was heated to 50° for 17 hours while stirring. After cooling, the solution was poured into 140 ml of water and extracted twice with 140 ml of diethyl ether each time and once with 140 ml of ethyl acetate. The combined organic phases were washed once with 140 ml of water and once with 140 ml of saturated sodium chloride solution, dried over magnesium sulfate and the solution was concentrated in a vacuum. The brown oil obtained was purified by column chromatography on silica gel (toluene). 0.8 g (38%) of (RS)-1-(2-azido-propyl)-6-chloro-1,4-dihydro-indeno[1,2-b]pyrrole was obtained as a yellowish oil.

e) 0.8 g of (RS)-1-(2-azido-propyl)-6-chloro-1,4-dihydro-indeno[1,2-b]pyrrole dissolved in 80 ml of anhydrous ethanol were hydrogenated on 80 mg of platinum oxide for 3 hours. The catalyst was subsequently filtered off, rinsed with ethanol and the solvent was drawn off in a vacuum. The colorless oil obtained was dissolved in 150 ml of anhydrous diethyl ether, filtered and treated while stirring with a solution of 170 mg of fumaric acid in 15 ml of methanol. The mixture was stirred at room temperature for 4 hours and the white crystals were subsequently filtered off. 780 mg (87%) of (RS)-2-(6-chloro-1,4-dihydro-indeno[1,2-b]pyrrol-1-yl)-1-methyl-ethylamine fumarate (1:0.5) with m.p. 212° were obtained.

EXAMPLE 54 a) A solution 11.9 g of 7-methoxy-4-chromanone, 13.8 ml of 3-buten-2-ol and 120 mg of p-toluenesulfonic acid in 14 ml of 2,2-dimethoxypropane and 120 ml of anhydrous toluene was boiled under reflux for 24 hours. The reaction mixture was subsequently concentrated in a vacuum and purified by column chromatography on silica gel (hexane/diethyl ether 4:1). 6.3 g (41%) of (RS)-2-(2-buten-1-yl)-7-methoxy-4-chromanone were obtained as a yellow oil.

b) An ozone stream (3 g ozone/hour) was conducted while stirring for 1 hour through a solution, cooled to −70°, of 6.25 g of (RS)-2-(2-buten-1-yl)-7-methoxy-4-chromanone in 90 ml of anhydrous dichloromethane and 30 ml of anhydrous methanol. Subsequently, the solution was flushed with oxygen for 5 minutes and with argon for 15 minutes. After the addition of 3 ml of dimethyl sulfide, the mixture was stirred at room temperature for 16 hours. The reaction mixture was subsequently evaporated in a vacuum. The residue was treated with 60 ml of dichloromethane and, after the addition of 15 ml of water and 15 ml of trifluoroacetic acid, stirred at room temperature for 3 hours. The mixture was subsequently poured into 100 ml of water and neutralized while stirring by the spatula-wise addition of sodium hydrogen carbonate. An additional 70 ml of water were added. The phases were separated and the aqueous phase was extracted twice with 100 ml of dichloromethane each time. The combined organic phases were dried over magnesium sulfate and concentrated in a vacuum. 2.9 g (49%) of 2-(2-oxoethyl)-7-methoxy-4-chromanone were obtained as a yellow oil.

c) A solution of 2.38 g of (RS)-2-(2-oxoethyl)-7-methoxy-4-chromanone and 80 mg of p-toluenesulfonic acid in 90 ml of anhydrous toluene was heated on a water separator. A solution of 3.25 g of (RS)-1-amino-2-propanol in 20 ml of anhydrous toluene was added dropwise to the boiling solution over a period of 5 minutes. Subsequently, the mixture was boiled for an additional 35 minutes, during which the solvent was reduced to a volume of 20 ml. The cooled reaction mixture was purified by column chromatography on silica gel (ethyl acetate/toluene 2:3). 1.95 g (70%) of (RS)-1-(1,4-dihydro-8-methoxy[1]-benzopyrano[4,3-b]pyrrol-1-yl)-propan-2-ol were obtained as a brown oil.

d) 1.15 ml of methanesulfonyl chloride were added dropwise while stirring to a solution, cooled to 0°, of 1.92 g of (RS)-1-(1,4-dihydro-8-methoxy[1]benzopyrano[4,3-b]pyrrol-1-yl)-propan-2-ol and 4.13 ml of triethylamine in 50 ml of anhydrous dichloromethane and the mixture was stirred at this temperature for an additional 1.5 hours. The reaction mixture was subsequently diluted with 280 ml of diethyl ether, washed twice with 70 ml of saturated sodium hydrogen carbonate solution each time and the combined aqueous phases were extracted once with 70 ml of diethyl ether. The combined organic phases were washed with 140 ml of saturated sodium chloride solution, dried over magnesium sulfate and evaporated in a vacuum. The brown oil obtained was dissolved in 50 ml of anhydrous dimethylformamide, treated with 0.96 g of sodium azide and the reaction mixture was heated to 60° while stirring for 18 hours. After cooling, the solution was poured into 140 ml of water and extracted twice with 140 ml of diethyl ether each time. The combined organic phases were washed once with 100 ml of water and once with 100 ml of saturated sodium chloride solution, dried over magnesium sulfate and the solution was concentrated in a vacuum. The brown oil obtained was purified by column chromatography on silica gel (toluene). 1.58 g (75%) of (RS)-1-(2-azido-propyl)-1,4-dihydro-8-methoxy-[1]benzopyrano[4,3-b]pyrrole were obtained as a colorless oil.

e) 1.57 g of (RS)-1-(2-azido-propyl)-1,4-dihydro-8-methoxy-[1]benzopyrano[4,3-b]pyrrole dissolved in 60 ml of anhydrous ethanol were hydrogenated on 160 mg of platinum oxide for 17 hours. The catalyst was subsequently filtered off, rinsed with ethanol and the solvent was drawn off in a vacuum. The colorless oil obtained was dissolved in 100 ml of anhydrous diethyl ether, filtered and treated while stirring with a solution of 281 mg of fumaric acid in 20 ml of methanol. The mixture was stirred at room temperature for 18 hours and the white crystals were subsequently filtered off. 1.42 g (86%) of (RS)-1-(1,4-dihydro-[1]benzopyrano-[4,3-b]pyrrol-1-yl)-1-methyl-ethylamine fumarate (1:0.5) with m.p. 197°–198° were obtained.

EXAMPLE 55 a) A solution of 50.0 g of 5-methoxy-1-indanone, 80 ml of 3-buten-2-ol, 132 ml of 2,2-dimethoxypropane and 600 mg of p-toluenesulfonic acid in 500 ml of toluene was brought to boiling. The resulting methanol/acetone mixture was distilled off and the reaction solution was subsequently boiled under reflux for an additional 48 hours. After cooling, the solution was evaporated in a vacuum. Purification on silica gel (hexane/diethyl ether 5:1) yielded 19.2 g (31%) of (RS)-2-(2-buten-1-yl)-5-methoxy-1-indanone as a pale yellow oil.

b) Ozone (3 g ozone/hour) was conducted while stirring for 85 minutes through a solution, cooled to −70°, of 19.2 g of (RS)-2-(2-buten-1-yl)-5-methoxy-1-indanone in 600 ml of anhydrous methanol. Subsequently, the solution was flushed with oxygen and then 9.1 ml of dimethyl sulfide were added to the cold solution. The solution came to room temperature overnight and was evaporated in a vacuum. The residue was chromatographed (dichloromethane) over a column with oxalic acid solution adsorbed on silica gel (600 g silica gel; 100 ml 10% oxalic acid solution). 14.1 g (78%) of (RS)-2-(2-oxoethyl)-5-methoxy-1-indanone were obtained as a yellow oil.

c) An ozone stream (3 g ozone/hour) was conducted while stirring during 60 minutes through a solution, cooled to −70°, of 13.3 g of (RS)-2-(2-oxoethyl)-5-methoxy-1-indanone in 200 ml of anhydrous dichloromethane and 100 ml of anhydrous methanol. Subsequently, the solution was flushed with oxygen for 5 minutes and with argon for 10 minutes. After the addition of 6.82 ml of dimethyl sulfide, the mixture was stirred at room temperature for 16 hours. The reaction mixture was evaporated in a vacuum. The residue was treated with 200 ml of dichloromethane and, after the addition of 25 ml of water and 25 ml of trifluoroacetic acid, stirred at room temperature for 3 hours. The mixture was subsequently poured into 100 ml of water and neutralized while stirring by the spatula-wise addition of sodium hydrogen carbonate. An additional 100 ml of water were added. The phases were separated and the aqueous phase was extracted twice with 150 ml of dichloromethane each time. The combined organic phases were dried over magnesium sulfate and concentrated in a vacuum. There were obtained 11.6 g (92%) of (RS)-2-(2-oxoethyl)-5-methoxy-1-indanone as a yellow oil which was used in the next reaction without additional purification.

d) A solution of 2 g of (RS)-2-(2-oxoethyl)-5-methoxy-1-indanone and 80 mg of p-toluenesulfonic acid in 90 ml of anhydrous toluene was heated on a water separator. A solution of 2.94 g of (RS)-1-amino-2-propanol in 20 ml of anhydrous toluene was added dropwise to the boiling solution over a period of 5 minutes. Subsequently, the mixture was boiled for an additional 35 minutes, during which the solvent was reduced to a volume of 25 ml. The cooled reaction mixture was purified by column chromatography on silica gel (ethyl acetate/toluene 1:1). There were obtained 1.6 g (67%) of (RS)-1-(6-methoxy-1,4-dihydro-indeno[1,2-b]pyrrol-1-yl)-propan-2-ol as a brown oil which was used directly in the next reaction.

e) 1.9 ml of methanesulfonyl chloride were added dropwise while stirring to a solution, cooled to 0°, of 1.41 g of (RS)-1-(6-methoxy-1,4-dihydro-indeno[1,2-b]pyrrol-1-yl)-propan-2-ol and 3.24 ml of triethylamine in 50 ml of dichloromethane and the mixture was stirred at this temperature for an additional 1.5 hours. The reaction mixture was subsequently diluted with 150 ml of diethyl ether, washed twice with 70 ml of saturated sodium hydrogen carbonate solution each time and the combined aqueous phases were extracted once with 70 ml of diethyl ether. The combined organic phases were washed with 70 ml of saturated sodium chloride solution, dried over magnesium sulfate and evaporated in a vacuum. The brown oil obtained was dissolved in 40 ml of anhydrous dimethylformamide, treated with 558 mg of sodium azide and the reaction mixture was heated to 60° while stirring for 7 hours. After cooling the solution was poured into 140 ml of water and extracted twice with 140 ml of diethyl ether each time. The combined organic phases were washed once with 140 ml of water and once with 140 ml of saturated sodium chloride solution, dried over magnesium sulfate and the solution was concentrated in a vacuum. The brown oil obtained was purified by column chromatography on silica gel (toluene). 0.75 g (48%) of (RS)-1-(2-azido-propyl)-6-methoxy-1,4-dihydro-indeno[1,2-b]pyrrole was obtained as a colorless oil.

f) 0.75 g of (RS)-1-(2-azido-propyl)-6-methoxy-1,4-dihydro-indeno[1,2-b]pyrrole dissolved in 30 ml of anhydrous ethanol was hydrogenated on 60 mg of platinum oxide for 16 hours. The catalyst was subsequently filtered off, rinsed with ethanol and the solvent was drawn off in a vacuum. The colorless oil obtained was dissolved in 50 ml of anhydrous diethyl ether, filtered and treated while stirring with a solution of 324 mg of fumaric acid in 50 ml of methanol. The mixture was stirred at room temperature for 16 hours and the white crystals were subsequently filtered off. 530 mg (63%) of (RS)-2-(6-methoxy-1,4-dihydro-indeno[1,2-b]pyrrol-1-yl)-1-methyl-ethylamine fumarate (1:0.5) with m.p. 189° were obtained.

EXAMPLE 56 a) A solution of 1.9 g of (RS)-2-(2-oxoethyl)-4-chromanone and 80 mg of p-toluenesulfonic acid in 70 ml of anhydrous toluene was heated on a water separator. A solution of 3.0 g of (S)-1-amino-2-propanol in 20 ml of anhydrous toluene was added dropwise to the boiling solution over a period of 5 minutes. Subsequently, the mixture was boiled for an additional 35 minutes, during which the solvent was reduced to a volume of 20 ml. The cooled reaction mixture was purified by column chromatography on silica gel (ethyl acetate/toluene 2:3). 1.73 g (76%) of (S)-1-(1,4-dihydro-[1]benzopyrano[4,3-b]pyrrol-1-yl)-propan-2-ol were obtained as a yellow oil.

b) 1.15 ml of methanesulfonyl chloride were added dropwise while stirring to a solution, cooled to 0°, of 1.7 g of (S)-1-(1,4-dihydro-[1]benzopyrano[4,3-b]pyrrol-1-yl)-propan-2-ol and 4.13 ml of triethylamine in 50 ml of anhydrous dichloromethane and the mixture was stirred at this temperature for an additional 1.5 hours. The reaction mixture was subsequently diluted with 200 ml of diethyl ether, washed twice with 70 ml of saturated sodium hydrogen carbonate solution each time and the combined aqueous phases were extracted once with 70 ml of diethyl ether. The combined organic phases were washed with 140 ml of saturated sodium chloride solution, dried over magnesium sulfate and evaporated in a vacuum. The brown solid obtained was dissolved in 50 ml of anhydrous dimethylformamide, treated with 0.88 g of sodium azide and the reaction mixture was heated to 60° while stirring for 18 hours. After cooling, the solution was poured into 140 ml of water and extracted twice with 140 ml of diethyl ether each time. The combined organic phases were washed once with 100 ml of water and once with 100 ml of saturated sodium chloride solution, dried over magnesium sulfate and the solution was concentrated in a vacuum. The brown oil obtained was purified by column chromatography on silica gel (toluene). 1.49 g (79%) of (R)-1-(2-azido-propyl)-1,4-dihydro-[1]benzopyrano[4,3-b]-pyrrole were obtained as a colorless oil.

c) 1.47 g of (R)-1-(2-azido-propyl)-1,4-dihydro-[1]benzo-pyrano[4,3-b]-pyrrole dissolved in 60 ml of anhydrous ethanol were hydrogenated on 150 mg of platinum oxide for 18 hours. The catalyst was subsequently filtered off, rinsed with ethanol and the solvent was drawn off in a vacuum. The colorless oil obtained was dissolved in 100 ml of anhydrous diethyl ether, filtered and treated while stirring with a solution of 294 mg of fumaric acid in 20 ml of methanol. The mixture was stirred at room temperature for 18 hours and the white crystals were subsequently filtered off. 1.3 g (79%) of (R)-1-(1,4-dihydro-[1]benzopyrano[4,3-b]pyrrol-1-yl)-1-methyl-ethylamine fumarate (1:0.5) m.p. 194°–195° were obtained.

EXAMPLE 57 a) 0.5 g of N-[2-(4,5-dihydro-7-methoxy-1H-benz[g]indol-1-yl)ethyl]-acetamide were heated to 140° for 23 hours under argon in 21 ml of ethylene glycol/water 2:1 in the presence of 0.60 g of potassium hydroxide. The reaction mixture was left to cool and poured into 100 ml of semi-concentrated sodium chloride solution. The mixture was extracted three times with diethyl ether. The combined extracts were washed once with saturated sodium chloride solution, dried over sodium sulfate, filtered and evaporated. The crude product was dissolved in 20 ml of diethyl ether and added dropwise to a solution of 245 mg of fumaric acid in 20 ml of methanol. The mixture was left to stir for one hour. and the yellowish crystals were filtered off under suction. 241 mg (38%) of 2-(4,5-dihydro-7-methoxy-1H-benz[g]indol-1-yl)-ethylamine fumarate (1:0.8) with m.p. 195° were obtained.

EXAMPLE 58 a) 35.25 g of 5-methoxy-1-tetralone and 61 ml of N,N-dimethylhydrazine were heated to about 80° under argon for 5 hours. The mixture was left to cool, 200 ml of 10% sodium chloride solution were added and the mixture was extracted several times with diethyl ether. The mixture was dried over sodium sulfate, filtered and evaporated. The oily residue was distilled over a 10 cm Vigreux column. At 85°–95°/0.1 mbar there were obtained 36.4 g (83%) of 5-methoxy-1-tetralone N,N-dimethylhydrazone as a yellow oil.

b) 3.12 g of 5-methoxy-1-tetralone N,N-dimethylhydrazone and 4.15 ml of DMPU were dissolved in 70 ml of absolute THF under argon and cooled to –75°. 10.7 ml of a 1.6M solution of n-butyllithium in hexane were added dropwise. The mixture was stirred at –75° for 1 hour and thereupon treated slowly with 2.0 ml of bromoacetaldehyde dimethyl acetal. The mixture was left to warm to room temperature and stirred for 26 hours. 20 ml of water were added at about 0° and the mixture was extracted three times with ethyl acetate. After drying over sodium sulfate, the mixture was filtered, evaporated and the residue was chromatographed on silica gel with toluene, then with toluene/ethyl acetate 9:1. 1.62 g (37%) of 2-(2,2-dimethoxy-1-ethyl)-5-methoxy-1-tetralone N,N-dimethylhydrazone were obtained as an oil.

c) 280 mg of 2-(2,2-dimethoxy-1-ethyl)-5-methoxy-1-tetralone N,N-dimethylhydrazone were dissolved in 12.5 ml of THF and added to 5 ml of phosphate buffer (prepared from 2 ml of 1/15M potassium dihydrogen phosphate and 3 ml of 1/15M disodium hydrogen phosphate) as well as 156 mg of copper (II) chloride dihydrate. After stirring at room temperature for 3.5 hours, the reaction had finished. The mixture was treated with 10 ml of 20% ammonium chloride solution and 0.8 ml of conc ammonia. Then, the mixture was extracted several times with ethyl acetate, dried over sodium sulfate, filtered and evaporated. The residue was chromatographed on silica gel firstly with toluene, then with toluene/ethyl acetate 9:1. 180 mg (80%) of 2-(2-oxoethyl)-5-methoxy-1-tetralone were obtained as a yellowish oil (Rf= 0.31, silica gel (toluene/ethyl acetate 9:1)).

d) 175 mg of 2-(2-oxoethyl)-5-methoxy-1-tetralone and 144 mg of N-acetylethylenediamine were heated to reflux under argon in 4 ml of acetic acid for 1.5 hours. The solvent was removed in a vacuum. The residue was taken up in 25 ml of water and extracted several times with dichloromethane. Chromatography on 20 g of silica gel with ethyl acetate gave a greenish coloured oil. This was crystallized from toluene for purification. 91 mg (46%) of N-[2-(4,5-dihydro-6-methoxy-1H-benz[g]indol-1-yl)ethyl]-acetamide with m.p. 133° were obtained.

e) 3.34 g of N-[2-(4,5-dihydro-6-methoxy-1H-benz[g]indol-1-yl)ethyl]-acetamide were heated to 140° for 23 hours. under argon in 5 ml of ethylene glycol/water 2:1 in the presence of 3.93 g of potassium hydroxide. The reaction mixture was left to cool and was poured into 300 ml of semi-concentrated sodium chloride solution. The mixture was extracted three times with diethyl ether, dried over sodium sulfate, filtered and evaporated. The crude product was dissolved in 30 ml of methanol and treated with 1.61 g of fumaric acid. The separated crystals were recrystallized from a total of 140 ml of methanol. 3.8 g (90%) of 2-(4,5-dihydro-6-methoxy-1H-benz[g]indol-1-yl)-ethylamine fumarate (1:1) were obtained as yellowish crystals with m.p. 198°.

EXAMPLE 59 a) 6.30 g of N-[2-(4,5-dihydro-8-methoxy-1H-benz[g]indol-1-yl)ethyl]-acetamide were heated to 140° for 21 hours under argon in 64 ml of ethylene glycol/water 2:1 in the presence of 7.40 g of potassium hydroxide. The reaction mixture was left to cool and was poured into 250 ml of semi-concentrated sodium chloride solution. The mixture was extracted three times with diethyl ether. The combined extracts were washed once with saturated sodium chloride solution, dried over sodium sulfate, filtered and evaporated. The crude product was dissolved in 100 ml of methanol and treated with 2.6 g of fumaric acid. The separated crystals were recrystallized from a total of 340 ml of methanol. 3.8 g (49%) of 2-(4,5-dihydro-8-methoxy-1H-benz[g]indol-1-yl)-ethylamine fumarate (1:1) were obtained as yellowish crystals with m.p. 183°–185°.

EXAMPLE 60 a) 8.85 g of 8-chloro-1-tetralone were dissolved in 90 ml of tetrachloromethane under argon and added to 21.0 ml of 3-buten-2-ol and 190 mg of p-toluenesulfonic acid. The reaction solution was heated to reflux on a water separator for 9 days. The solvent was removed in a vacuum and the residue was chromatographed on 200 g of silica gel firstly with hexane/ethyl acetate 9:1 and then with hexane/ethyl acetate 4:1. In addition to large amounts of unreacted educt (8.3 g), there were obtained 4.1 g (35%) of 2-(2-buten-1-yl)-8-chloro-1-tetralone as a yellow oil.

b) 7.7 g of 2-(2-buten-1-yl)-8-chloro-1-tetralone were dissolved in a mixture of 220 ml of dichloromethane and 60 ml of methanol, cooled to −75° and the double bond was ozonized in the usual manner. After flushing the reaction mixture with oxygen and argon, 4.8 ml of dimethyl sulfide were added dropwise. The mixture was left to warm slowly to room temperature and was stirred for an additional 15 hours. The crude product (10.8 g) was dissolved in about 100 ml of dichloromethane and added to a mixture of 12 ml of 10% aqueous oxalic acid, 120 g of silica gel and 300 ml of dichloromethane. The mixture was stirred at room temperature for 2 hours. 6.4 g (83%) of 8-chloro-2-(2-oxoethyl)-1-tetralone were obtained as a pale brown oil by extraction with dichloromethane.

c) 325 mg of 8-chloro-2-(2-oxoethyl)-1-tetralone and 290 mg of N-acetylethylenediamine were heated to reflux in 14ml of acetic acid under argon for 1 hour. The solvent was removed in a vacuum and the residue was taken up in 10 ml of water and extracted several times with ethyl acetate. Chromatography on 20 g of silica gel with hexane/ethyl acetate 1:1 and then with ethyl acetate gave 190 mg (45%) of N-[2-(9-chloro-4,5-dihydro-1H-benz[g]indol-1-yl)ethyl]-acetamide as yellowish crystals with m.p. 146°–147°.

d) 1.55 g of N-[2-(9-chloro-4,5-dihydro-1H-benz[g]indol-1-yl)ethyl]-acetamide were heated to 140° for 21 hours under argon in 23 ml of ethylene glycol/water 2:1 in the presence of 1.80 g of potassium hydroxide. The reaction mixture was left to cool and was poured into 60 ml of semi-concentrated sodium chloride solution. The mixture was extracted three times with diethyl ether, the combined extracts were washed once with saturated sodium chloride solution, dried over sodium sulfate, filtered and evaporated. The crude product was dissolved in 10 ml of methanol and treated with 0.62 g of fumaric acid. The separated crystals were recrystallized from a total of 20 ml of methanol. 1.26 g (65%) of 2-(9-chloro-4,5-dihydro-1H-benz[g]indol-1-yl)-ethylamine fumarate were obtained as yellowish crystals with m.p. 181°–183°.

EXAMPLE 61

1.80 g of N-[6-chloro-2-(4,5-dihydro-1H-benz[g]indol-1-yl)ethyl]-acetamide were heated to 140° for 20 hours under argon in 17 ml of ethylene glycol/water 12:5 in the presence of 0.9 g of potassium hydroxide. The mixture was left to cool and was treated with 140 ml of semi-saturated sodium chloride solution. The mixture was extracted three times with diethyl ether. The combined extracts were washed once with saturated sodium chloride solution, dried over sodium sulfate, filtered and evaporated. The brown oil was chromatographed on 50 g of silica gel with dichloromethane/methanol (19:1, then 9:1). The crude product was dissolved in 7 ml of diethyl ether and 0.98 g of fumaric acid was added. The solvent was removed in a vacuum and the residue was recrystallized from 50 ml of chloroform/ethanol 4:1. 1.41 g (62%) of 2-(6-chloro-4,5-dihydro-1H-benz[g]indol-1-yl)-ethylamine fumarate (1:1) with m.p. 187°–188° were obtained.

EXAMPLE 62

0.5 g of N-[7-chloro-2-(4,5-dihydro-1H-benz[g]indol-1-yl)ethyl]-acetamide was heated to 140° for 22 hours under argon in 4.5 ml of ethylene glycol/water 2:1 in the presence of 0.25 g of potassium hydroxide. The mixture was left to cool and was treated with 40 ml of water and 10 ml of saturated sodium chloride solution. The mixture was extracted three times with diethyl ether. The combined extracts were washed once with saturated sodium chloride solution, dried over sodium sulfate, filtered and evaporated. The crude product was dissolved in 30 ml of diethyl ether and added dropwise to a suspension of 208 mg of fumaric acid in 30 ml of diethyl ether. The solvent was removed in a vacuum and the residue was recrystallized from 75 ml of ethanol/ethyl acetate 3:2. 355 mg (58%) of 2-(7-chloro-4,5-dihydro-1H-benz[g]indol-1-yl)-ethylamine fumarate (1:1) with m.p. 176°–177° were obtained as white crystals.

EXAMPLE 63

1.0 g g of N-[8-chloro-2-(4,5-dihydro-1H-benz[g]indol-1-yl)ethyl]-acetamide was heated to 140° for 24 hours under argon in 7.5 ml of ethylene glycol/water 2:1 in the presence of 0.50 g of potassium hydroxide. The mixture was left to cool and was poured into 75 ml of ice-water. After the addition of 25 ml of saturated sodium chloride solution, the mixture was extracted three times with diethyl ether. The combined extracts were washed once with saturated sodium chloride solution, dried over sodium sulfate, filtered and evaporated. The crude product was dissolved in 20 ml of diethyl ether and added dropwise to a suspension of 406 mg of fumaric acid in 80 ml of diethyl ether. The solvent was removed in a vacuum and the residue was recrystallized from 90 ml of ethanol/ethyl acetate 5:4. 556 mg (45%) of 2-(8-chloro-4,5-dihydro-1H-benz[g]indol-1-yl)-ethylamine fumarate (1:1) with m.p. 179°–180° were obtained as white crystals.

EXAMPLE 64 a) A solution of 23.9 g of 4-thiochromanone, 30 ml of 3-buten-2-ol and 240 mg of p-toluenesulfonic acid in 30 ml of 2,2-dimethoxy-propane and 240 ml of anhydrous toluene was boiled under reflux for 20 hours. The reaction mixture was subsequently concentrated in a vacuum and purified by column chromatography on silica gel (hexane/diethyl ether 5:1). 15.3 g (48%) of (RS)-2-(2-buten-1-yl)-4-thiochromanone were obtained as a yellow oil.

b) An ozone stream (3 g ozone/hour) was conducted while stirring for 15 minutes through a solution, cooled to −70°, of 3 g of (RS)-2-(2-buten-1-yl)-4-thiochromanone in 100 ml of anhydrous dichloro-methane and 30 ml of anhydrous methanol. Subsequently, the solution was flushed with oxygen for 5 minutes and with argon for 10 minutes. After the addition of 2 ml of dimethyl sulfide, the mixture was stirred at room temperature for 16 hours. The reaction mixture was subsequently evaporated in a vacuum. The residue was treated with 50 ml of dichloromethane and, after the addition of 5 ml of water and 5 ml of trifluoroacetic acid, stirred at room temperature for 1 hour. The mixture was subsequently poured into 50 ml of water and neutralized by the spatula-wise addition of sodium hydrogen carbonate while stirring. An additional 50 ml of water were added, the phases were separated and the aqueous phase was extracted twice with 80 ml of dichloromethane each time. The combined organic phases were dried over magnesium sulfate and concentrated in a vacuum. There were obtained 2.8 g (99%) of 2-(2-oxoethyl)-4-thiochromanone as a yellow oil which was used in the next reaction without further recrystallization.

c) A solution of 2 g of 2-(2-oxoethyl)-4-thiochromanone and 120 mg of p-toluenesulfonic acid in 100 ml of anhydrous toluene was heated on a water separator. A solution of 2.9 g of (RS)-1-amino-2-propanol in 20 ml of anhydrous toluene was added dropwise to the boiling solution over a period of 5 minutes. Subsequently, the mixture was boiled for an additional 35 minutes, during which the solvent was reduced to a volume of 20 ml. The cooled reaction mixture was purified by column chromatography on silica gel (ethyl acetate/toluene 1:1). There were obtained 1.8 g (76%) of (RS)-1-(1,4-dihydro-[1]benzothiopyrano[4,3-b]pyrrol-1-yl)-propan-2-ol as a pale brown solid which was used in the next reaction without further recrystallization.

d) 1.15 ml of methanesulfonyl chloride were added dropwise while stirring to a solution, cooled to 0°, of 1.8 g of (RS)-1-(1,4-dihydro-[1]benzothiopyrano[4,3-b]pyrrol-1-yl)-propan-2-ol and 4.1 ml of triethylamine in 50 ml of anhydrous dichloromethane and the mixture was stirred at this temperature for an additional 1.5 hours. The reaction mixture was subsequently diluted with 180 ml of diethyl ether, washed twice with 70 ml of saturated sodium hydrogen carbonate solution each time and the combined aqueous phases were extracted once with 70 ml of diethyl ether. The combined organic phases were washed with 140 ml of saturated sodium chloride solution, dried over magnesium sulfate and evaporated in a vacuum. The brown oil obtained was dissolved in 50 ml of anhydrous dimethylformamide, treated with 0.96 g of sodium azide and the reaction mixture was heated to 600 while stirring for 17 hours. After cooling, the solution was poured into 100 ml of water and extracted twice with 120 ml of diethyl ether each time. The combined organic phases were washed once with 100 ml of water and once with 100 ml of saturated sodium chloride solution, dried over magnesium sulfate and the solution was concentrated in a vacuum. The brown oil obtained was purified by column chromatography on silica gel (toluene). 1.17 g (59%) of (RS)-1-(2-azido-propyl)-1,4-dihydro-[1]benzothiopyrano[4,3-b]pyrrole were obtained as a light yellow oil.

e) 1.17 g of (RS)-1-(2-azido-propyl)-1,4-dihydro-[1]benzo-thiopyrano[4,3-b]pyrrole dissolved in 30 ml of anhydrous tetra-hydrofuran were added dropwise while stirring to a suspension of 247 mg of lithium aluminum hydride in 30 ml of anhydrous tetrahydrofuran. The mixture was subsequently boiled under reflux for 2 hours. Hydrolysis was effected with 20% aqueous tetrahydrofuran. The liquid phase was separated and the residue was boiled with 50 ml of 20% aqueous tetrahydrofuran for an additional 15 minutes. The combined solutions were treated with 100 ml of diethyl ether. The organic phase was separated and the aqueous phase was extracted twice with 50 ml of diethyl ether each time. The combined organic phases were washed with 100 ml of saturated sodium chloride solution, dried over magnesium sulfate and concentrated in a vacuum. There were obtained 970 mg (92%) of a colorless oil which was dissolved in 100 ml of anhydrous diethyl ether, filtered and treated while stirring with a solution of 461 mg of fumaric acid in 20 ml of methanol. The mixture was stirred at room temperature for 3 hours and the light yellow crystals were subsequently filtered off. 1.2 g (77%) of (RS)-1-(1,4-dihydro-[1]benzothiopyrano[4,3-b]pyrrol-1-yl)-1-methyl-ethylamine fumarate (1:1) with m.p. 201° were obtained.

EXAMPLE 65 a) A solution of 29.5 g of 1-indanone, 73.5 ml 3-buten-2-ol, 77.0 ml of 2,2-dimethoxypropane and 400 mg of p-toluenesulfonic acid in 400 ml of toluene was boiled under reflux for 24 hours. After cooling, the solution was washed with 100 ml of saturated sodium hydrogen carbonate solution. The aqueous washing was extracted with 150 ml of ethyl acetate and the organic phases were combined, dried with magnesium sulfate and evaporated in a vacuum. Purification on silica gel (hexane/diethyl ether 7:1) yielded 19.8 g (48%) of (RS)-2-(2-buten-1-yl)-1-indanone as a pale yellow oil.

b) Ozone (3 g ozone/hour) was conducted while stirring for 120 minutes through a solution, cooled to −70°, of 19.8 g of (RS)-2-(2-buten-1-yl)-1-indanone in 700 ml of anhydrous dichloromethane and 200 ml of anhydrous methanol. Subsequently, the solution was flushed with oxygen and then 11.0 ml of dimethyl sulfide were added to the cold solution. The solution came to room temperature overnight and was evaporated in a vacuum. The residue was purified on silica gel (ethyl acetate). 10.1 g (43%) of (RS)-2-(2,2-dimethoxyethyl)-1-indanone were obtained as a yellow oil.

c) A solution of 1.7 g of (RS)-2-(2,2-dimethoxyethyl)-1-indanone, 25 g of N-acetylethylenediamine and 30 ml of trifluoroacetic acid in 500 ml of ethanol was boiled under reflux for 96 hours. After cooling and adding 21.5 g of sodium hydroxide in 100 ml of water, the mixture was evaporated to about 100 ml. The mixture was treated with 200 ml of ethyl acetate and washed in succession with 100 ml of saturated sodium chloride solution, 1N hydrochloric acid (4×100 ml), 2N sodium hydroxide solution (4×100 ml) and 100 ml of water. The aqueous washings were extracted with 100 ml of ethyl acetate and the organic phases were combined, dried with magnesium sulfate and evaporated in a vacuum. The residue was purified on basic aluminum oxide (III, dichloromethane) and then on silica gel (ethyl acetate). 0.4 g (22%) of N-[2-(1,4-dihydro-indeno[1,2-b]pyrrol-1-yl)-ethyl]-acetamide was obtained as a colorless solid.

d) 385 mg of N-[2-(1,4-dihydro-indeno[1,2-b]pyrrol-1-yl)-ethyl]-acetamide were heated to 140° for 22 hours under argon in 6 ml of ethylene glycol/water 2:1 in the presence of 540 mg of potassium hydroxide. The mixture was left to cool and was treated with 20 ml of semi-saturated sodium chloride solution. The mixture was extracted three times with diethyl ether and the combined extracts were dried over sodium sulfate, filtered and evaporated. The brown oil was dissolved in 5 ml of methanol and treated with 185 mg of fumaric acid, whereby pale brown crystals separated. These were dissolved in 50 ml of warm methanol. After cooling to room temperature, the product was crystallized by the slow addition of 50 ml of diethyl ether. The product obtained was heated in 15 ml of tert.-butyl methyl ether for 1 hour, filtered off under suction and dried in a vacuum. 220 mg (53%) of 2-(1,4-dihydro-indeno[1,2-b]pyrrol-1-yl)-ethylamine fumarate with m.p. 201°–202° were obtained.

EXAMPLE 66 a) A solution of 29.6 g of benzosuberone and 60.9 ml of N,N-dimethylhydrazine in 150 ml of anhydrous ethanol was boiled under reflux for 3 days. Ethanol and excess N,N-dimethylhydrazine were removed in a vacuum and the residue was taken up in dichloro-methane and dried with magnesium sulfate. Distillation over a 10 cm Vigreaux column yielded 32.9 g (83%) of benzosuberone N',N'-dimethylhydrazone as a yellow oil. B.p.: 78°–81° C./0.2 mbar.

b) A solution of 33.6 g of benzosuberone N',N'-dimethylhydrazone and 29.9 ml of N,N,N',N-tetramethylethylenediamine in 400 ml of absolute tetrahydrofuran was cooled to −70° under argon and 106 ml of a 1.6M solution of n-butyllithium in hexane was added dropwise within 15 minutes. The mixture was then stirred at −70° for 30 minutes, left to warm to −30° and treated dropwise at this temperature with 23.4 ml of bromoacetaldehyde dimethyl acetal. After stirring at −30° for 1.5 hours, the mixture was left to warm to room temperature overnight and the solution was treated with 500 ml of water. The mixture was extracted with ethyl acetate (1×500, 2×100 ml) and the organic phases were combined, dried with magnesium sulfate and evaporated in a vacuum. After column chromatography on silica gel (hexane/ethyl acetate 10:1–3:1), 37.7 g (78%) of (RS)-2-(2,2-dimethoxyethyl)-benzosuberone N',N'-dimethylhydrazone were obtained as an orange-yellow oil.

c) A suspension of 37.7 g of (RS)-2-(2,2-dimethoxyethyl)-benzosuberone N',N'-dimethylhydrazone, 30.2 g of sodium acetate and 78.8 g of sodium periodate in 2000 ml of tetrahydrofuran was treated with 300 ml of acetic acid and stirred at 50° overnight. The mixture was cooled, poured into 300 ml of water and extracted with dichloro-methane (1×3000, 2×1000 ml). The organic phases were combined, dried with magnesium sulfate and concentrated in a vacuum. Column chromatography on silica gel (hexane/ethyl acetate 2:1) yielded 8.2 g (25%) of (RS)-2-(2,2-dimethoxyethyl)-benzosuberone as a red oil in addition to 9.7 g (26%) of starting material.

d) 8.2 g of (RS)-2-(2,2-dimethoxyethyl)-benzosuberone were chromatographed over a column of oxalic acid solution adsorbed on silica gel (180 g of silica gel/20 ml of 10% oxalic acid solution). 6.2 g (90%) of (RS)-2-(2-oxoethyl)-benzosuberone were obtained as a red oil.

e) A solution of 6.2 g of (RS)-2-(2-oxoethyl)-benzosuberone and 3.3 g of N-acetylethylenediamine in 50 ml of anhydrous dichloro-methane was treated with 50 g of molecular sieve 4 Å and boiled under reflux overnight. After cooling, the mixture was filtered over Celite, evaporated in a vacuum and the residue was recrystallized from hexane/ethyl acetate 2:1. 4.0 g (50%) of N-[2-(1,4,5,6-tetrahydro-benzo[6,7]cyclohepta[1,2-b]pyrrol-1-yl)-ethyl]-acetamide were obtained as a colorless solid.

f) 1.80 g of N-[2-(1,4,5,6-tetrahydro-benzo[6,7]cyclohepta[1,2-b]pyrrol-1-yl)-ethyl]-acetamide were heated to 140° for 24 hours under argon in 18 ml of ethylene glycol/water 2:1 in the presence of 1.0 g of potassium hydroxide. The reaction mixture was left to cool and was poured into 140 ml of semi-concentrated sodium chloride solution. The mixture was extracted three times with diethyl ether and the combined extracts were washed once with saturated sodium chloride solution, dried over sodium sulfate, filtered and evaporated. The thus-obtained oil was chromatographed on 60 g of silica gel with methylene chloride/methanol 19:1. The crude product was dissolved in 5 ml of diethyl ether and treated with 505 mg of fumaric acid in 10 ml of diethyl ether. The crystals were filtered off and recrystallized from 50 ml of ethyl acetate/ethanol 2:1. 1.65 g (72%) of 2-(1,4,5,6-tetrahydro-benzo[6,7]cyclohepta[1,2-b]pyrrol-1-yl)-ethylamine fumarate (1:1) were obtained as white crystals with m.p. 175°–176°.

EXAMPLE 67 a) A solution of 26.4 g of 7-methoxy-1-indanone, 33.6 ml of 3-buten-2-ol and 265 mg of p-toluenesulfonic acid in 33.6 ml of 2,2-dimethoxypropane and 265 ml of anhydrous toluene was boiled under reflux for 17 hours. The reaction mixture was subsequently concentrated in a vacuum and purified by column chromatography on silica gel (hexane/diethyl ether 5:1). 9.9 g (28%) of (RS)-2-(2-buten-1-yl)-7-methoxy-1-indanone were obtained as a yellow oil.

b) An ozone stream (3 g ozone/hour) was conducted while stirring for 45 minutes through a solution, cooled to −70°, of 9.9 g of (RS)-2-(2-buten-1-yl)-7-methoxy-1-indanone in 200 ml of anhydrous dichloromethane and 100 ml of anhydrous methanol. Subsequently, the solution was flushed with oxygen for 5 minutes and with argon for 10 minutes. After the addition of 5 ml of dimethyl sulfide, the mixture was stirred at room temperature for 16 hours. The reaction mixture was evaporated in a vacuum. The residue was treated with 200 ml of dichloromethane and, after the addition of 20 ml of water and 20 ml of trifluoroacetic acid, stirred at room temperature for 3 hours. The mixture was subsequently poured into 100 ml of water and neutralized by the spatula-wise addition of sodium hydrogen carbonate while stirring. An additional 100 ml of water were added. The phases were separated and the aqueous phase was extracted twice with 150 ml of dichloromethane each time. The combined organic phases were dried over magnesium sulfate, concentrated in a vacuum and the crude product obtained was cystallized from ethyl acetate/hexane. 6.6 g (71%) of (RS)-2-(2-oxoethyl)-7-methoxy-1-indanone were obtained as a white solid with m.p. 102°.

c) A solution of 2.04 g of (RS)-2-(2-oxoethyl)-7-methoxy-1-indanone and 80 mg of p-toluenesulfonic acid in 90 ml of anhydrous toluene was heated on a water separator. A solution of 3.0 g of (RS)-1-amino-2-propanol in 20 ml of anhydrous toluene was added dropwise to the boiling solution over a period of 5 minutes. Subsequently, the mixture was boiled for an additional 35 minutes, during which the solvent was reduced to a volume of 25 ml. The cooled reaction mixture was purified by column chromatography on silica gel (ethyl acetate/toluene 2:3). There was obtained 1.1 g (45%) of (RS)-1-(8-methoxy-1,4-dihydro-indeno[1,2-b]pyrrol-1-yl)-propan-2-ol as a brown oil which was used directly in the next reaction.

d) 0.7 ml of methanesulfonyl chloride was added dropwise while stirring to a solution, cooled to 0°, of 1.1 g of (RS)-1-(8-methoxy-1,4-dihydro-indeno[1,2-b]pyrrol-1-yl)-propan-2-ol and 2.5 ml of triethylamine in 25 ml of dichloromethane and the mixture was stirred at this temperature for an additional 1.5 hours. The reaction mixture was subsequently diluted with 200 ml of diethyl ether, washed twice with 70 ml of saturated sodium hydrogen carbonate solution each time and the combined aqueous phases were extracted once with 140 ml of diethyl ether. The combined organic phases were washed with 70 ml of saturated sodium chloride solution, dried over magnesium sulfate and evaporated in a vacuum. The brown oil obtained was dissolved in 40 ml of anhydrous dimethylformamide, treated with 526 mg of sodium azide and the reaction mixture was heated to 60° while stirring for 29 hours. After cooling, the solution was poured into 140 ml of water and extracted twice with 140 ml of diethyl ether each time. The combined organic phases were washed once with 140 ml of water and once with 140 ml of saturated sodium chloride solution, dried over magnesium sulfate and the solution was concentrated in a vacuum. The brown oil obtained was purified by column chromatography on silica gel (toluene). 0.68 g (56%) of (RS)-1-(2-azido-propyl)-8-methoxy-1,4-dihydro-indeno[1,2-b]-pyrrole was obtained as a colorless oil.

e) 0.67 g of (RS)-1-(2-azido-propyl)-8-methoxy-1,4-dihydro-indeno[1,2-b]-pyrrole dissolved in 25 ml of anhydrous ethanol was hydrogenated on 67 mg of platinum oxide for 5 hours. The catalyst was subsequently filtered off, rinsed with ethanol and the solvent was drawn off in a vacuum. The colorless oil obtained was dissolved in 70 ml of anhydrous diethyl ether, filtered and treated while stirring with a solution of 273 mg of fumaric acid in 10 ml of methanol. The mixture was stirred at room temperature for 22 hours and the white crystals were subsequently filtered off. 559 mg (74%) of (RS)-2-(8-methoxy-1,4-dihydro-indeno[1,2-b]pyrrol-1-yl)-1-methyl-ethylamine fumarate (1:0.5) with m.p. 193° were obtained.

EXAMPLE 68 a) A solution of 23.3 g of (RS)-3-phenyl-1-tetralone, 21.6 ml of 3-buten-2-ol and 230 mg of p-toluenesulfonic acid in 21.6 ml of 2,2-dimethoxypropane and 230 ml of anhydrous toluene was boiled under reflux for 30 hours. The reaction mixture was subsequently concentrated in a vacuum and purified by column chromatography on silica gel (hexane/diethyl ether 4:1). 11.8 g (41%) of (2RS/3RS)-2-(2-buten-1-yl)-3-phenyl-1-tetralone were obtained as a red oil.

b) An ozone stream (3 g ozone/hour) was conducted while stirring for 40 minutes through a solution, cooled to −70°, of 11.8 g of (2RS/3RS)-2-(2-buten-1-yl)-3-phenyl-1-tetralone in 300 ml of anhydrous dichloromethane and 100 ml of anhydrous methanol. Subsequently, the solution was flushed with oxygen for 5 minutes and with argon for 10 minutes. After the addition of 4.45 ml of dimethyl sulfide, the mixture was stirred for 17 hours at room temperature. The reaction mixture was evaporated in a vacuum and the residue was treated with 300 ml of dichloromethane and, after the addition of 30 ml of water and 30 ml of trifluoroacetic acid, stirred at room temperature for 2 hours. The mixture was subsequently poured into 100 ml of water and neutralized by the spatula-wise addition of sodium hydrogen carbonate while stirring. An additional 100 ml of water were added, the phases were separated and the aqueous phase was extracted twice with 150 ml of dichloromethane each time. The combined organic phases were dried over magnesium sulfate, concentrated in a vacuum and the crude product obtained was purified by column chromatography on silica gel (toluene/ethyl acetate 9:1). 9.7 g (86%) of (2RS/3RS)-2-(2-oxoethyl)-3-phenyl-1-tetralone were obtained as a yellow oil.

c) A solution of 2 g of (2RS/3RS)-2-(2-oxoethyl)-3-phenyl-1-tetralone and 80 mg of p-toluenesulfonic acid in 70 ml of anhydrous toluene was heated on a water separator. A solution of 2.18 g of (RS)-1-amino-2-propanol in 20 ml of anhydrous toluene was added dropwise to the boiling solution over a period of 5 minutes. Subsequently, the mixture was boiled for an additional 30 minutes, during which the solvent was reduced to a volume of 25 ml. The cooled reaction mixture was purified by column chromatography on silica gel (ethyl acetate/toluene 1:9). There were obtained 1.04 g (45%) of (2RS/4RS)-1-(4,5-dihydro-4-phenyl-1-H-benz[g]indol-1-yl)-propan-2-ol as a brown oil which was used directly in the next reaction.

d) 0.53 ml of methanesulfonyl chloride was added dropwise while stirring to a solution, cooled to 0°, of 1.04 g of (2RS/4RS)-1-(4,5-dihydro-4-phenyl-1-H-benz[g]indol-1-yl)-propan-2-ol and 1.9 ml of triethylamine in 30 ml of dichloromethane and the mixture was stirred at this temperature for an additional 1.5 hours. The reaction mixture was subsequently diluted with 200 ml of diethyl ether, washed twice with 70 ml of saturated sodium hydrogen carbonate solution each time and the combined aqueous phases were extracted once with 130 ml of diethyl ether. The combined organic phases were washed with 100 ml of saturated sodium chloride solution, dried over magnesium sulfate and evaporated in a vacuum. The brown oil obtained was dissolved in 25 ml of anhydrous dimethylformamide, treated with 0.45 g of sodium azide and the reaction mixture was heated to 60° while stirring for 6 hours. After cooling, the solution was poured into 140 ml of water and extracted twice with 140 ml of diethyl ether each time. The combined organic phases were washed once with 100 ml of water and once with 70 ml of saturated sodium chloride solution, dried over magnesium sulfate and the solution was concentrated in a vacuum. The brown oil obtained was purified by column chromatography on silica gel (toluene). 473 mg (42%) of (2RS/4RS)-1-(2-azido-propyl)-4,5-dihydro-4-phenyl-1H-benz[g]indole were obtained as a colorless oil.

e) 473 mg of (2RS/4RS)-1-(2-azido-propyl)-4,5-dihydro-4-phenyl-1H-benz[g]indole dissolved in 20 ml of anhydrous ethanol were hydrogenated on 50 mg of platinum oxide for 5 hours. The catalyst was subsequently filtered off, rinsed with ethanol and the solvent was drawn off in a vacuum. The colorless oil obtained was dissolved in 40 ml of anhydrous diethyl ether, filtered and treated while stirring with a solution of 148 mg of fumaric acid in 5 ml of methanol. The mixture was stirred at room temperature for 7 hours and the white crystals were subsequently filtered off. 446 mg (74%) of (2RS/4RS)-2-(4,5-dihydro-4-phenyl-1H-benz[g]indol-1-yl)-1-methyl-ethylamine fumarate (1:1) with m.p. 187° were obtained.

EXAMPLE 69 a) A solution of 20 g of (RS)-3-phenyl-1-indanone, 20 ml of 3-buten-2-ol and 200 mg of p-toluenesulfonic acid in 20 ml of 2,2-dimethoxypropane and 200 ml of anhydrous toluene was boiled under reflux for 22 hours. The reaction mixture was subsequently concentrated in a vacuum and purified by column chromatography on silica gel (hexane/ethyl acetate 5:1). 10 g (40%) of (2RS/3RS)-2-(2-buten-1-yl)-3-phenyl-1-indanone were obtained as a yellow oil.

b) An ozone stream (3 g ozone/hour) was conducted while stirring for 40 minutes through a solution, cooled to −70°, of 10 g of (2RS/3RS)-2-(2-buten-1-yl)-3-phenyl-1-indanone in 200 ml of anhydrous dichloromethane and 70 ml of anhydrous methanol. Subsequently, the solution was flushed was oxygen for 5 minutes and with argon for 10 minutes. After the addition of 4.3 ml of dimethyl sulfide, the mixture was stirred at room temperature for 16 hours. The reaction mixture was evaporated in a vacuum. The residue was treated with 150 ml of dichloromethane and, after the addition of 20 ml of water and 20 ml of trifluoroacetic acid, stirred at room temperature for 1 hour. The mixture was subsequently poured into 100 ml of water and neutralized by the spatula-wise addition of sodium hydrogen carbonate while stirring. An additional 100 ml of water were added. The phases were separated and the aqueous phase was extracted twice with 150 ml of dichloromethane each time. The combined organic phases were dried over magnesium sulfate and concentrated in a vacuum. There were obtained 9.5 g (99%) of (2RS/3RS)-2-(2-oxoethyl)-3-phenyl-1-indanone as an oil which was used in the next reaction without additional purification.

c) A solution of 3.0 g of (2RS/3RS)-2-(2-oxoethyl)-3-phenyl-1-indanone and 100 mg of p-toluenesulfonic acid in 100 ml of anhydrous toluene was heated on a water separator. A solution of 3.6 g of (RS)-1-amino-2-propanol in 20 ml of anhydrous toluene was added dropwise to the boiling solution over a period of 5 minutes. Subsequently, the mixture was boiled for an additional 35 minutes, during which the solvent was reduced to a volume of 25 ml. The cooled reaction mixture was purified by column chromatography on silica gel (ethyl acetate/toluene 1:1). There were obtained 2.4 g (69%) of (2RS/4RS)-1-(4-phenyl-1,4-dihydro-indeno[1,2-b]pyrrol-1-yl)-propan-2-ol as an oil which was used directly in the next reaction.

d) 1.24 ml of methanesulfonyl chloride were added dropwise while stirring to a solution, cooled to 0°, of 2.3 g of (2RS/4RS)-1-(4-phenyl-1,4-dihydro-indeno[1,2-b]pyrrol-1-yl)-propan-2-ol and 4.46 ml of triethylamine in 60 ml of dichloromethane and the mixture was stirred at this temperature for an additional 1.5 hours. The reaction mixture was subsequently diluted with 200 ml of diethyl ether, washed twice with 70 ml of saturated sodium hydrogen carbonate solution each time and the combined aqueous phases were extracted once with 140 ml of diethyl ether. The combined organic phases were washed with 70 ml of saturated sodium chloride solution, dried over magnesium sulfate and evaporated in a vacuum. The brown oil obtained was dissolved in 60 ml of anhydrous dimethylformamide, treated with 884 mg of sodium azide and the reaction mixture was heated to 60° while stirring for 16 hours. After cooling, the solution was poured into 140 ml of water and extracted twice with 140 ml of diethyl ether each time. The combined organic phases were washed once with 140 ml of water and with 140 ml of saturated sodium chloride solution, dried over magnesium sulfate and the solution was concentrated in a vacuum. The brown oil obtained was purified by column chromatography on silica gel (toluene). 1.22 g (49%) of (2RS/4RS)-1-(2-azido-propyl)-4-phenyl-1,4-dihydro-indeno[1,2-b]-pyrrole were obtained as a light brown oil.

e) 1.2 g of (2RS/4RS)-1-(2-azido-propyl)-4-phenyl-1,4-dihydro-indeno[1,2-b]-pyrrole dissolved in 50 ml of anhydrous ethanol were hydrogenated on 120 mg of platinum oxide for 5 hours. The catalyst was subsequently filtered off, rinsed with ethanol and the solvent was drawn off in a vacuum. The colorless oil obtained was dissolved in 100 ml of anhydrous diethyl ether, filtered and treated while stirring with a solution of 480 mg of fumaric acid in 20 ml of methanol. The mixture was stirred at room temperature for 16 hours and the crystals were subsequently filtered off. 1.04 g (65%) of (2RS/4RS)-2-(4-phenyl-1,4-dihydro-indeno[1,2-b]pyrrol-1-yl)-1-methyl-ethylamine fumarate (1:0.86) with m.p. 191° were obtained.

EXAMPLE 70 a) 13.7 g of 8-methoxy-1-tetralone were dissolved in 140 ml of toluene under argon and added to 13.3 ml of 3-buten-2-ol, 14.2 ml of 2,2-dimethoxypropane and 300 mg of p-toluenesulfonic acid. The reaction solution was heated to reflux for 90 hours. The solvent was removed in a vacuum and the residue was chromatographed on 500 g of silica gel firstly with hexane/ethyl acetate 9:1, then with hexane/ethyl acetate 4:1 and finally with hexane/ethyl acetate 1:1. In addition to large amounts of unreacted educt (8.3 g) there were obtained 3.95 g (22%) of 2-(2-buten-1-yl)-8-methoxy-1-tetralone as a yellow oil.

b) 11.4 g of 2-(2-buten-1-yl)-8-methoxy-1-tetralone were dissolved in a mixture of 340 ml of dichloromethane and 100 ml of methanol, cooled to −75° and the double bond was ozonized in the usual manner. After flushing the reaction mixture with oxygen and argon, 7.2 ml of dimethyl sulfide were added dropwise. The mixture was left to warm slowly to room temperature and was stirred for an additional 17 hours. The solvent was removed in a vacuum and the residue was taken up in 200 ml of diethyl ether and washed with water. Drying with sodium sulfate, filtration and evaporation gave 10.6 g of a mixture of dimethyl acetal and aldehyde. 7.0 g of this mixture were dissolved in 70 ml of methylene chloride and added to a mixture of 8.4 ml of 10% aqueous oxalic acid, 80 g of silica gel and 210 ml of dichloromethane. The mixture was stirred at room temperature for 2 hours. 5.6 g of 8-methoxy-2-(2-oxoethyl)-1-tetralone were obtained as a pale brown oil by extraction with dichloromethane/diethyl ether 9:1.

c) 400 mg of 8-methoxy-2-(2-oxoethyl)-1-tetralone were heated to reflux for 15 minutes under argon with 205 mg of N-acetyl-ethylenediamine in 8 ml of toluene. The solvent was removed in a vacuum and the residue was chromatographed on 40 g of silica gel with hexane/ethyl acetate 1:1 and then with ethyl acetate. 280 mg (54%) of N-[2-(4,5-dihydro-9-methoxy-1H-benz[g]indol-1-yl)ethyl]-acetamide were obtained as yellowish crystals with m.p. 132°–133°.

d) 2.3 g of N-[2-(4,5-dihydro-9-methoxy-1H-benz[g]indol-1-yl)ethyl]-acetamide were heated to 140° for 16 hours under argon in 23 ml of ethylene glycol/water 2:1 in the presence of 2.70 g of potassium hydroxide. The reaction mixture was left to cool and was poured into 200 ml of semi-concentrated sodium chloride solution. The mixture was extracted three times with diethyl ether and the combined extracts were washed once with saturated sodium chloride solution, dried over sodium sulfate, filtered and evaporated. The crude product was dissolved in 20 ml of methanol and treated with 0.93 g of fumaric acid. The separated crystals were recrystallized from a total of 70 ml of methanol. 1.76 g (61%) of 2-(4,5-dihydro-9-methoxy-1H-benz[g]indol-1-yl)-ethylamine fumarate (1:1) were obtained as yellowish crystals with m.p. 184°–185°.

EXAMPLE 71 a) A solution of 21.5 g of 4-methoxy-1-indanone, 27.4 ml of 3-buten-2-ol and 210 mg of p-toluenesulfonic acid in 27.4 ml of 2,2-dimethoxypropane and 210 ml of anhydrous toluene was boiled under reflux for 16 hours. The reaction mixture was subsequently concentrated in a vacuum and purified by column chromatography on silica gel (hexane/ethyl acetate 9:1). 6.42 g (23%) of (RS)-2-(2-buten-1-yl)-4-methoxy-1-indanone were obtained as a yellow oil.

b) An ozone stream (3 g ozone/hour) was conducted while stirring for 35 minutes through a solution, cooled to −70°, of 6.42 g of (RS)-2-(2-buten-1-yl)-4-methoxy-1-indanone in 180 ml of anhydrous dichloromethane and 60 ml of anhydrous methanol. Subsequently, the solution was flushed with oxygen for 5 minutes and with argon for 10 minutes. After the addition of 3.3 ml of dimethyl sulfide, the mixture was stirred at room temperature for 16 hours. The reaction mixture was evaporated in a vacuum, the residue was treated with 200 ml of dichloromethane and, after the addition of 20 ml of water and 20 ml of trifluoroacetic acid, stirred at room temperature for 2 hours. The mixture was subsequently poured into 100 ml of water and neutralized by the spatulawise addition of sodium hydrogen carbonate while stirring. An additional 100 ml of water were added, the phases were separated and the aqueous phase was extracted twice with 150 ml of dichloromethane each time. The combined organic phases were dried over magnesium sulfate, concentrated in a vacuum and the crude product obtained was crystallized from ethyl acetate/hexane. 5.1 g (84%) of (RS)-2-(2-oxoethyl)-4-methoxy-1-indanone were obtained as a white solid with m.p. 71°.

c) A solution of 2.04 g of (RS)-2-(2-oxoethyl)-4-methoxy-1-indanone and 80 mg of p-toluenesulfonic acid in 90 ml of anhydrous toluene was heated on a water separator. A solution of 3.13 g of (RS)-1-amino-2-propanol in 20 ml of anhydrous toluene was added dropwise to the boiling solution over a period of 5 minutes. Subsequently, the mixture was boiled for an additional 35 minutes, during which the solvent was reduced to a volume of 25 ml. The cooled reaction mixture was purified by column chromatography on silica gel (ethyl acetate/toluene 1:4). There was obtained 0.7 g (29%) of (RS)-1-(5-methoxy-1,4-dihydro-indeno[1,2-b]pyrrol-1-yl)-propan-2-ol as a brown oil which was used directly in the next reaction.

d) 0.45 ml of methanesulfonyl chloride was added dropwise while stirring to a solution, cooled to 0°, of 0.7 g of (RS)-1-(5-methoxy-1,4-dihydro-indeno[1,2-b]pyrrol-1-yl)-propan-2-ol and 1.6 ml of triethylamine in 20 ml of dichloromethane and the mixture was stirred at this temperature for an additional 1.5 hours. The reaction mixture was subsequently diluted with 200 ml of diethyl ether, washed twice with 70 ml of saturated sodium hydrogen carbonate solution each time and the combined aqueous phases were extracted once with 140 ml of diethyl ether. The combined organic phases were washed with 70 ml of saturated sodium chloride solution, dried over magnesium sulfate and evaporated in a vacuum. The brown oil obtained was dissolved in 20 ml of anhydrous dimethylformamide, treated with 366 mg of sodium azide and the reaction mixture was heated to 60° while stirring for 18 hours. After cooling, the solution was poured into 140 ml of water and extracted twice with 140 ml of diethyl ether each time. The combined organic phases were washed once with 140 ml of water and once with 140 ml of saturated sodium chloride solution, dried over magnesium sulfate and the solution was concentrated in a vacuum. The brown oil obtained was purified by column chromatography on silica gel (toluene). 0.55 g (73%) of (RS)-1-(2-azido-propyl)-5-methoxy-1,4-dihydro-indeno[1,2-b]-pyrrole was obtained as a colorless oil.

e) 0.54 g of (RS)-1-(2-azido-propyl)-5-methoxy-1,4-dihydro-indeno[1,2-b]-pyrrole dissolved in 20 ml of anhydrous ethanol was hydrogenated on 54 mg of platinum oxide for 17 hours. The catalyst was subsequently filtered off, rinsed with ethanol and the solvent was drawn off in a vacuum. The colorless oil obtained was dissolved in 50 ml of anhydrous diethyl ether, filtered and treated while stirring with a solution of 110 mg of fumaric acid in 10 ml of methanol. The mixture was stirred at room temperature for 22 hours and the white crystals were subsequently filtered off. 500 mg (83%) of (RS)-2-(5-methoxy-1,4-dihydro-indeno[1,2-b]pyrrol-1-yl)-1-methyl-ethylamine fumarate (1:0.5) with m.p. 194° were obtained.

EXAMPLE 72 a) A solution of 0.95 g of (2RS/4RS)-2-(4,5-dihydro-4-phenyl-1-H-benz[g]indol-1-yl)-1-methyl-ethylamine in 15 ml of anhydrous pyridine was treated with 15 ml of acetic anhydride and heated to 50° for 30 minutes while stirring. The reaction mixture was subsequently poured on to ice and treated with 70 ml of saturated sodium hydrogen carbonate solution. The mixture was extracted twice with 100 ml of dichloromethane each time and the combined organic phases were washed once with cold 3N sulphuric acid and once with cold saturated sodium hydrogen carbonate solution. After drying the solution over magnesium sulfate, the solvent was drawn off in a vacuum and the residue was taken up with 40 ml of anhydrous dioxane. 729 mg of DDQ were added and the mixture was boiled under reflux for 1 hour. Subsequently, the reaction mixture was concentrated in a vacuum and the residue was purified by column chromatography on silica gel (dichloromethane/methanol 20:1). There was obtained 0.69 g (64%) of (RS)-N-[2-(4-phenyl-1-H-benz[g]indol-1-yl)-1-methyl-ethyl]-acetamide as a pale brown solid which was used in the next reaction without further recrystallization.

b) A mixture of 670 mg of (RS)-N-[2-(4-phenyl-1-H-benz[g]indol-1-yl)-1-methyl-ethyl]-acetamide, 1.32 g of potassium hydroxide in 15 ml of water and 30 ml of ethylene glycol was boiled under reflux for 46 hours. The reaction mixture was subsequently poured into 80 ml of saturated sodium chloride solution and extracted twice with 80 ml of ethyl acetate each time. The combined organic phases were washed once with 100 ml of saturated sodium chloride solution and dried over magnesium sulfate. After concentration in a vacuum, the residue was purified by column chromatography on silica gel (dichloromethane/methanol 9:1) and the resulting oil [308 mg] was dissolved in 30 ml of anhydrous diethyl ether, filtered and treated while stirring with a solution of 119 mg of fumaric acid in 6 ml of methanol. The mixture was stirred at room temperature for 20 hours and the white crystals were subsequently filtered off. 308 mg (41%) of (RS)-2-(4-phenyl-1-H-benz[g]indol-1-yl)-1-methyl-ethylamine fumarate (1:0.7) with m.p. >230° were obtained.

EXAMPLE 73 a) A solution of LDA, prepared at 0° from 3.12 ml of diisopropyl-amine and 13.8 ml of n-butyllithium (1.6N in hexane), in 40 ml of anhydrous tetrahydrofuran was added dropwise while stirring during 10 minutes to a solution, cooled to −70°, of 2.96 g of 6-methoxy-1-indanone in 300 ml of anhydrous tetrahydrofuran. After 15 minutes, a solution of 1.62 ml of chloroacetone in 40 ml of anhydrous tetrahydrofuran was added dropwise to the solution during 5 minutes and the mixture was subsequently stirred at room temperature for 2 hours. The reaction mixture was poured on to 150 ml of ice Thereafter 150 ml of saturated sodium chloride solution were added and the mixture was extracted twice with 300 ml of diethyl ether each time. The combined organic phases were washed once with 200 ml of saturated sodium chloride solution, dried over magnesium sulfate and concentrated in a vacuum. The crude product obtained was purified by column chromatography on silica gel (hexane/diethyl ether 3:2, then 2:3). 1.8 g (45%) of (RS)-6-methoxy-2-(2-oxopropyl)-1-indanone were obtained as a red oil.

b) A solution of 1.8 g of (RS)-6-methoxy-2-(2-oxopropyl)-1-indanone and 70 mg of p-toluenesulfonic acid in 70 ml of anhydrous toluene was heated on a water separator. A solution of 2.48 g of (RS)-1-amino-2-propanol in 20 ml of anhydrous toluene were added dropwise to the boiling solution over a period of 5 minutes. Subsequently, the mixture was boiled for an additional 3 hours, during which the solvent was reduced to a volume of 30 ml. The cooled reaction mixture was purified by column chromatography on silica gel (diethyl ether/hexane 7:3). 1.37 g (65%) of (RS)-1-(7-methoxy-2-methyl-1,4-dihydro-indeno[1,2-b]pyrrol-1-yl)-propan-2-ol were obtained as a solid with m.p. 110°.

c) 0.81 ml of methanesulfonyl chloride was added dropwise while is stirring to a solution, cooled to 0°, of 1.35 g of (RS)-1-(7-methoxy-2-methyl-1,4-dihydro-indeno[1,2-b]pyrrol-1-yl)-propan-2-ol and 2.9 ml of triethylamine in 40 ml of dichloromethane. The reaction mixture was subsequently added to 70 ml of water, extracted twice with 100 ml of dichloromethane each time and the combined organic phases were washed once with 70 ml of saturated sodium hydrogen carbonate solution and once with 70 ml of saturated sodium chloride solution, dried over magnesium sulfate and evaporated in a vacuum. The brown oil obtained was dissolved in 40 ml of anhydrous dimethylformamide, treated with 0.68 g of sodium azide and the reaction mixture was heated to 80° while stirring for 23 hours. After cooling the solution was poured into 70 ml of water and extracted twice with 100 ml of ethyl acetate each time. The combined organic phases were washed once with 70 ml of water and once with 70 ml of saturated sodium chloride solution, dried over magnesium sulfate and the solution was concentrated in a vacuum. The brown oil obtained was purified by column chromatography on silica gel (toluene). 0.93 g (62%) of (RS)-1-(2-azido-propyl)-7-methoxy-2-methyl-1,4-dihydro-indeno[1,2-b]pyrrole was obtained as a colorless oil.

d) 0.92 g of (RS)-1-(2-azido-propyl)-7-methoxy-2-methyl-1,4-dihydro-indeno[1,2-b]pyrrole dissolved in 70 ml of anhydrous ethanol was hydrogenated on 90 mg of platinum oxide for 16 hours. The catalyst was subsequently filtered off, rinsed with ethanol and the solvent was drawn off in a vacuum. The colorless oil obtained was dissolved in 70 ml of anhydrous diethyl ether, filtered and treated while stirring with a solution of 160 mg of fumaric acid in 15 ml of methanol. The mixture was stirred at room temperature for 17 hours and the white crystals were subsequently filtered off. 800 mg (78%) of (RS)-2-(7-methoxy-2-methyl-1,4-dihydro-indeno[1,2-b]pyrrol-1-yl)-1-methyl-ethylamine fumarate (1:0.5) with m.p. 187°–188° were obtained.

EXAMPLE 74 a) A solution of LDA, prepared at 0° from 4.25 ml of diisopropyl-amine and 18.8 ml of N-butyllithium (1.6N in hexane), in 60 ml of anhydrous tetrahydrofuran, was added dropwise while stirring during 15 minutes to a solution, cooled to −70°, of 3.24 g of 5-methoxy-1-indanone in 350 ml of anhydrous tetrahydrofuran. After 45 minutes, a solution of 1.6 ml of chloroacetone in 60 ml of anhydrous tetra-hydrofuran was added dropwise to the solution during 15 minutes and the mixture was subsequently stirred at room temperature for 2 hours. The reaction mixture was poured on to 150 ml of ice, 150 ml of saturated sodium chloride solution were added and the mixture was extracted twice with 300 ml of diethyl ether each time. The combined organic phases were washed once with 200 ml of saturated sodium chloride solution, dried over magnesium sulfate and concentrated in a vacuum. The crude product obtained was purified by column chromatography on silica gel (hexane/diethyl ether 3:7). 1.4 g (32%) of (RS)-5-methoxy-2-(2-oxopropyl)-1-indanone were obtained as a solid with m.p. 73°.

b) A solution of 1.2 g of (RS)-5-methoxy-2-(2-oxopropyl)-1-indanone and 60 mg of p-toluenesulfonic acid in 70 ml of anhydrous toluene was heated on a water separator. A solution of 1.65 g of (RS)-1-amino-2-propanol in 20 ml of anhydrous toluene was added dropwise to the boiling solution over a period of 5 minutes. Subsequently, the mixture was boiled for an additional 3 hours, during which the solvent was reduced to a volume of 30 ml. The cold reaction mixture was purified by column chromatography on silica gel (diethyl ether/hexane 7:3). 1.17 g (82%) of (RS)-1-(6-methoxy-2-methyl-1,4-dihydro-indeno[1,2-b]pyrrol-1-yl)-propan-2-ol were obtained as an oil.

c) 0.7 ml of methanesulfonyl chloride was added dropwise while stirring to a solution, cooled to 0°, of 1.16 g of (RS)-1-(6-methoxy-2-methyl-1,4-dihydro-indeno[1,2-b]pyrrol-1-yl)-propan-2-ol and 2.5 ml of triethylamine in 50 ml of dichloromethane and the solution was stirred at this temperature for an additional 1.5 hours. The reaction mixture was subsequently added to 70 ml of water, extracted twice with 100 ml of dichloromethane each time and the combined organic phases were washed once with 70 ml of saturated sodium hydrogen carbonate solution and once with 70 ml of saturated sodium chloride solution, dried over magnesium sulfate and evaporated in a vacuum. The brown oil obtained was dissolved in 40 ml of anhydrous dimethylformamide, treated with 0.58 g of sodium azide and the reaction mixture was heated to 80° while stirring for 16 hours. After cooling the solution was poured into 70 ml of water and extracted twice with 100 ml of ethyl acetate each time. The combined organic phases were washed once with 70 ml of water and once with 70 ml of saturated sodium chloride solution, dried over magnesium sulfate and the solution was concentrated in a vacuum. The brown oil obtained was purified by column chromatography on silica gel (toluene). 0.86 g (55%) of (RS)-1-(2-azido-propyl)-6-methoxy-2-methyl-1,4-dihydro-indeno[1,2-b]pyrrole was obtained as a colorless oil.

d) 0.85 g of (RS)-1-(2-azido-propyl)-6-methoxy-2-methyl-1,4-dihydro-indeno[1,2-b]pyrrole dissolved in 50 ml of anhydrous ethanol was hydrogenated on 85 mg of platinum oxide for 17 hours. The catalyst was subsequently filtered off, rinsed with ethanol and the solvent was drawn off in a vacuum. The colorless oil obtained was dissolved in 70 ml of anhydrous diethyl ether, filtered and treated while stirring with a solution of 155 mg of fumaric acid in 15 ml of methanol. The mixture was stirred at room temperature for 19 hours and the white crystals were subsequently filtered off. 780 mg (83%) of (RS)-2-(6-methoxy-2-methyl-1,4-dihydro-indeno[1,2-b]pyrrol-1-yl)-1-methyl-ethylamine fumarate (1:0.5) with m.p. 215° were obtained.

EXAMPLE A

Tablets of the following composition were prepared in a conventional manner:

|  | mg/tablet |
|---|---|
| Active substance | 100 |
| Powd. lactose | 95 |
| White corn starch | 35 |
| Polyvinylpyrrolidone | 8 |
| Na carboxymethylstarch | 10 |
| Magnesium stearate | 2 |
| Table weight | 250 |

EXAMPLE B

Tablets of the following composition are prepared in the usual manner:

|  | mg/tablet |
|---|---|
| Active substance | 200 |
| Powd. lactose | 100 |
| White corn starch | 64 |
| Polyvinylpyrrolidone | 12 |
| Na carboxymethylstarch | 20 |
| Magnesium stearate | 4 |
| Table weight | 400 |

EXAMPLE C

Capsules of the following composition are prepared in the usual manner:

|                         | mg/capsule |
|-------------------------|-----------|
| Active substance        | 50        |
| Cryst. lactose          | 60        |
| Microcrystalline cellulose | 34     |
| Talc                    | 5         |
| Magnesium stearate      | 1         |
| Capsule fill weight     | 400       |

The active substance having a suitable partical size, the crystalline lactose and the microcrystalline cellulose are homogeneously mixed with one another, sieved and thereafter talc and magnesium stearate are admixed. The finished mixture is filled into hard gelatin capsules of suitable size.

What is claimed is:

1. A compound of the formula

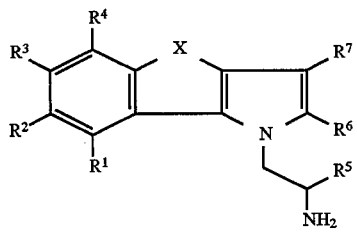

wherein

R$^1$ to R$^4$ are, independently, hydrogen, halogen, lower alkyl, phenyl, cycloalkyl or lower alkoxy and R$^2$ additionally is lower alkoxycarbonyl, acyloxy or mesyloxy;

R$^5$ to R$^7$ are, independently, hydrogen or lower alkyl;

X is —CH$_2$CH(C$_6$H$_5$)—, —CH=C(C$_6$H$_5$)—, —YCH$_2$—, —CH=CH— or —(CR$^{11}$R$^{12}$)$_n$;

R$^{11}$ and R$^{12}$ are, independently, hydrogen, phenyl, lower alkyl or halogen;

n is 1 to 3 and

Y is O or S, or a pharmaceutically acceptable salt of a basic compound of formula I with an acid.

2. A compound according to claim 1, wherein R$^5$ is hydrogen or lower alkyl.

3. A compound according to claim 2, wherein R$^5$ is methyl.

4. A compound according to claim 3, wherein R$^1$, R$^3$ and R$^4$ are hydrogen and R$^2$ is halogen, lower alkyl or methoxy.

5. A compound according to claim 1 (S)-2-(4,4,7-Trimethyl-1,4-dihydro-indeno[1,2-b]pyrrol-1-yl)-1-methyl-ethylamine.

6. A compound according to claim 1 (S)-2-(7-Methoxy-4,4-dimethyl-1,4-dihydro-indeno[1,2-b]pyrrol-1-yl)-1-methyl-ethylamine.

7. A compound according to claim 1 (S)-2-(7-Ethyl-4,4-dimethyl-1,4-dihydro-indeno[1,2-b]pyrrol-1-yl)-1-methyl-ethylamine.

8. A compound according to claim 1 (S)-2-(7-Methyl-1,4-dihydro-indeno[1,2-b]pyrrol-1-yl)-1-methyl-ethylamine.

9. A compound according to claim 1 (S)-2-(7-Brom-1,4-dihydro-indeno[1,2-b]pyrrol-1-yl)-1-methyl-ethylamine.

10. A compound according to claim 1 (S)-2-(7-Methoxy-1,4-dihydro-indeno[1,2-b]pyrrol-1-yl)-1-methyl-ethylamine.

11. A compound according to claim 1 (S)-2-(7-Chloro-1,4-dihydro-indeno[1,2-b]pyrrol-1-yl)-1-methyl-ethylamine.

12. A compound according to claim 1 (S)-2-(8-Methoxy-1H-benz[g]indol-1-yl)-1-methyl-ethylamine.

13. A compound of the formula

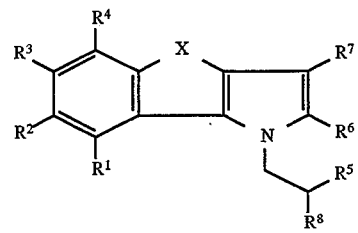

wherein

R$^1$ to R$^4$ are, independently, hydrogen, halogen, lower alkyl, phenyl, cycloalkyl or lower alkoxy and R$^2$ additionally is lower alkoxycarbonyl, acyloxy or mesyloxy;

R$^5$ to R$^7$ are, independently, hydrogen or lower alkyl;

R$^8$ is an azido group, an acetylamino group, a protected amino group or a hydroxy group;

X is —CH$_2$CH(C$_6$H$_5$)—, —CH=C(C$_6$H$_5$)—, —YCH$_2$—, —CH=CH— or —(CR$^{11}$R$^{12}$)$_n$;

R$^{11}$ and R$^{12}$ are, independently, hydrogen, phenyl, lower alkyl or halogen;

n is 1 to 3 and

Y is O or S, or a pharmaceutically acceptable salt of a basic compound of formula I with an acid.

14. A compound according to claim 13, wherein R$^5$ is hydrogen or lower alkyl.

15. A compound according to claim 13, wherein R$^5$ is methyl.

16. A pharmaceutical composition comprising an effective amount of a compound of the formula

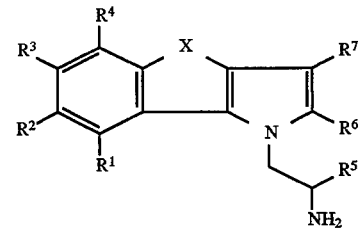

wherein

R$^1$ to R$^4$ are, independently, hydrogen, halogen, lower alkyl, phenyl, cycloalkyl or lower alkoxy and R$^2$ additionally is lower alkoxycarbonyl, acyloxy or mesyloxy;

R$^5$ to R$^7$ are, independently, hydrogen or lower alkyl;

X is —CH$_2$CH(C$_6$H$_5$)—, —CH=C(C$_6$H$_5$)—, —YCH$_2$—, —CH=CH— or —(CR$^{11}$R$^{12}$)$_n$;

R$^{11}$ and R$^{12}$ are, independently, hydrogen, phenyl, lower alkyl or halogen;

n is 1 to 3 and

Y is O or S, or a pharmaceutically acceptable salt of a basic compound of formula I with an acid and an inert carrier material.

17. A pharmaceutical composition according to claim 16, wherein R$^5$ is hydrogen or lower alkyl.

18. A pharmaceutical composition according to claim 16, wherein R$^5$ is methyl.

19. A pharmaceutical composition according to claim 16, wherein R$^1$, R$^3$ and R$^4$ are hydrogen and R$^2$ is halogen, lower alkyl or methoxy.

20. A pharmaceutical composition according to claim 16, wherein the compound of formula I is selected from the group consisting of (S)-2-(4,4,7-Trimethyl-1,4-dihydro-indeno[1,2-b]pyrrol-1-yl)-1-methyl-ethylamine, (S)-2-(7-Methoxy-4,4-dimethyl-1,4-dihydro-indeno[1,2-b]pyrrol-1-yl)-1-methyl-ethylamine, (S)-2-(7-Ethyl-4,4-dimethyl-1,4-dihydro-indeno[1,2-b]pyrrol-1-yl)-1-methyl-ethylamine, (S)-2-(7-Methyl-1,4-dihydro-indeno[1,2-b]pyrrol-1-yl)-1-methyl-ethylamine, (S)-2-(7-Brom-1,4-dihydro-indeno[1,2-b]pyrrol-1-yl)-1-methyl-ethylamine, (S)-2-(7-Methoxy-1,4-dihydro-indeno[1,2-b]pyrrol-1-yl)-1-methyl-ethylamine, (S)-2-(7-Chloro-1,4-dihydro-indeno[1,2-b]pyrrol-1-yl)-1-methyl-ethylamine, (S)-2-(8-Methoxy-1H-benz[g]indol-1-yl)-1-methyl-ethylamine.

21. A method for blocking serotonin receptors in a host requiring such treatment which comprises administering an effective amount of a compound of the formula

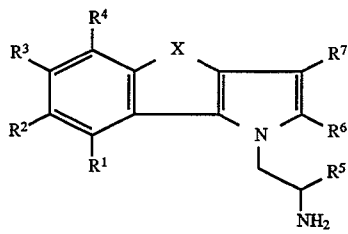

wherein $R^1$ to $R^4$ are, independently, hydrogen, halogen, lower alkyl, phenyl, cycloalkyl or lower alkoxy and $R^2$ additionally is lower alkoxycarbonyl, acyloxy or mesyloxy;

$R^5$ to $R^7$ are, independently, hydrogen or lower alkyl;

X is —$CH_2CH(C_6H_5)$—, —$CH$=$C(C_6H_5)$—, —$YCH_2$—, —$CH$=$CH$— or —$(CR^{11}R^{12})_n$—;

$R^{11}$ and $R^{12}$ are, independently, hydrogen, phenyl, lower alkyl or halogen;

n is 1 to 3 and

Y is O or S, or a pharmaceutically acceptable salt of a basic compound of formula I with an acid and an inert carrier material.

22. A method according to claim 21, wherein $R^5$ is hydrogen or lower alkyl.

23. A method according to claim 21, wherein $R^5$ is methyl.

24. A method according to claim 21, wherein $R^1$, $R^3$ and $R^4$ are hydrogen and $R^2$ is halogen, lower alkyl or methoxy.

25. A method according to claim 21, wherein the compound of formula I is selected from the group consisting of (S)-2-(4,4,7-Trimethyl-1,4-dihydro-indeno[1,2-b]pyrrol-1-yl)-1-methyl-ethylamine, (S)-2-(7-Methoxy-4,4-dimethyl-1,4-dihydro-indeno[1,2-b]pyrrol-1-yl)-1-methyl-ethylamine, (S)-2-(7-Ethyl-4,4-dimethyl-1,4-dihydro-indeno[1,2-b]pyrrol-1-yl)-1-methyl-ethylamine, (S)-2-(7-Methyl-1,4-dihydro-indeno[1,2-b]pyrrol-1-yl)-1-methyl-ethylamine, (S)-2-(7-Brom-1,4-dihydro-indeno[1,2-b]pyrrol-1-yl)-1-methyl-ethylamine, (S)-2-(7-Methoxy-1,4-dihydro-indeno[1,2-b]pyrrol-1-yl)-1-methyl-ethylamine, (S)-2-(7-Chloro-1,4-dihydro-indeno[1,2-b]pyrrol-1-yl)-1-methyl-ethylamine, (S)-2-(8-Methoxy-1H-benz[g]indol-1-yl)-1-methyl-ethylamine.

* * * * *